US010029007B2

(12) United States Patent
Drew et al.

(10) Patent No.: US 10,029,007 B2
(45) Date of Patent: Jul. 24, 2018

(54) STABILISATION OF POLYPEPTIDES

(71) Applicant: Stabilitech Biopharma Ltd, West Sussex (GB)

(72) Inventors: Jeffrey Drew, West Sussex (GB); David Thomas Woodward, West Sussex (GB); Stephen Ward, West Sussex (GB)

(73) Assignee: Stabilitech Biopharma Ltd, Burgess Hill (GB)

( * ) Notice: Subject to any disclaimer, the term of this patent is extended or adjusted under 35 U.S.C. 154(b) by 0 days.

(21) Appl. No.: 14/349,481

(22) PCT Filed: Oct. 5, 2012

(86) PCT No.: PCT/GB2012/052477
§ 371 (c)(1),
(2) Date: Apr. 3, 2014

(87) PCT Pub. No.: WO2013/050780
PCT Pub. Date: Apr. 11, 2013

(65) Prior Publication Data
US 2014/0294757 A1    Oct. 2, 2014

(30) Foreign Application Priority Data
Oct. 5, 2011 (GB) .................................. 1117233.5

(51) Int. Cl.
| A61K 39/39 | (2006.01) |
| A61K 47/26 | (2006.01) |
| C12N 9/96 | (2006.01) |
| A61K 9/19 | (2006.01) |
| A61K 47/18 | (2017.01) |
| A61K 47/20 | (2006.01) |
| A61K 47/22 | (2006.01) |

(52) U.S. Cl.
CPC ............... *A61K 39/39* (2013.01); *A61K 9/19* (2013.01); *A61K 47/183* (2013.01); *A61K 47/20* (2013.01); *A61K 47/22* (2013.01); *A61K 47/26* (2013.01); *C12N 9/96* (2013.01); *A61K 2800/84* (2013.01)

(58) Field of Classification Search
CPC ...... A61K 31/74; A61K 47/183; A61K 31/10; A61K 2039/552; A61K 2039/542; A61K 2039/55505; A61K 31/137; A61K 9/0019; A61K 9/0056; A61K 9/1694; A61K 9/2095; A61K 39/39; A61K 47/22; A61K 47/26; A61K 47/20; G01N 33/68; G01N 33/566
See application file for complete search history.

(56) References Cited
U.S. PATENT DOCUMENTS

| 3,927,208 A | 12/1975 | Zygraich et al. |
| 4,631,189 A * | 12/1986 | Kendall ............... A61K 31/195 424/278.1 |
| 4,639,339 A | 1/1987 | Murashige et al. |
| 4,808,700 A | 2/1989 | Anderson et al. |
| 4,816,568 A * | 3/1989 | Hamilton et al. ............ 530/399 |
| 4,950,596 A | 8/1990 | Cheng et al. |
| 5,109,026 A | 4/1992 | Hoskinson et al. |
| 5,169,758 A | 12/1992 | Fischer et al. |
| 5,240,843 A | 8/1993 | Gibson et al. |
| 5,580,856 A * | 12/1996 | Prestrelski ......... A61K 38/1825 514/1.1 |
| 5,618,539 A | 4/1997 | Dorval et al. |
| 5,691,163 A | 11/1997 | Cameron et al. |
| 6,037,116 A | 3/2000 | Wiggins et al. |
| 6,127,181 A | 10/2000 | Kadkade |
| 6,194,136 B1 | 2/2001 | Livesey et al. |
| 6,248,588 B1 | 6/2001 | Crespo et al. |
| 6,689,600 B1 | 2/2004 | Wu et al. |
| 7,235,391 B2 | 6/2007 | Wu et al. |
| 9,101,607 B2 | 8/2015 | Drew et al. |
| 2004/0110267 A1 | 6/2004 | Sundar |
| 2004/0253574 A1 | 12/2004 | Schuler et al. |
| 2005/0048058 A1* | 3/2005 | Yamazaki .............. C07K 16/22 424/155.1 |
| 2005/0239705 A1 | 10/2005 | Dake et al. |
| 2006/0073182 A1 | 4/2006 | Wong et al. |
| 2006/0154858 A1 | 7/2006 | Mattson et al. |
| 2006/0228334 A1 | 10/2006 | Rosa-Calatrava et al. |
| 2006/0247167 A1 | 11/2006 | Schlein et al. |

(Continued)

FOREIGN PATENT DOCUMENTS

| CA | 2083407 A1 | 5/1993 |
| CN | 101670104 A | 3/2010 |

(Continued)

OTHER PUBLICATIONS

Davidson et al. Effect of sucrose/raffinose mass ratios on the stability of co-lyophilized protein during storage above the Tg. Pharm Res. Apr. 2001;18(4):474-9.*
Izutsu et al. Stabilization of Protein Structure in Freeze-Dried Amorphous Organic Acid Buffer Salts. Chem. Pharm. Bull. 2009:57(11):1231-1236.*
Pikal et al. The effects of formulation variables on the stability of freeze-dried human growth hormone. Pharm Res. Apr. 1991;8(4):427-36.*
Michaelis et al. Dimethylglycine Buffer. J. Biol. Chem. 1936, 115:221-222.*
Santoro et al. Increased thermal stability of proteins in the presence of naturally occurring osmolytes. Biochemistry 1992, 31, 5278-5283.*
Publication by Lymphomation.org. http://www.lymphomation.org/side-effect-HAMA.htm[Dec. 2, 2017 3:41:16 PM].*
Suzuki et al. Mammalian lactoferrin receptors: structure and function. Cell. Mol. Life Sci. 62 (2005) 2560-2575.*

(Continued)

*Primary Examiner* — Marcela M Cordero Garcia
*Assistant Examiner* — Jia-Hai Lee
(74) *Attorney, Agent, or Firm* — Clark & Elbing LLP; Susan M. Michaud

(57) ABSTRACT

A method for preserving a polypeptide comprising: (a) providing an aqueous solution of (i) the polypeptide, (ii) one or more sugars, and (iii) a compound of formula (I) or a physiologically acceptable salt or ester thereof and/or a compound of formula (II) or a physiologically acceptable salt or ester thereof; and (b) drying the solution to form a composition incorporating the polypeptide.

11 Claims, 19 Drawing Sheets

(56) References Cited

U.S. PATENT DOCUMENTS

| | | | |
|---|---|---|---|
| 2007/0253941 A1* | 11/2007 | Naidu | A61K 31/12 424/94.1 |
| 2008/0107631 A1 | 5/2008 | Wu et al. | |
| 2008/0299168 A1 | 12/2008 | Dadey et al. | |
| 2009/0123436 A1 | 5/2009 | Opperman | |
| 2010/0029569 A1* | 2/2010 | Bjorn et al. | 514/12 |
| 2010/0260796 A1 | 10/2010 | Belin-Poput et al. | |
| 2011/0081363 A1* | 4/2011 | Whitney et al. | 424/184.1 |
| 2013/0071431 A1 | 3/2013 | Drew et al. | |
| 2013/0129685 A1 | 5/2013 | Drew et al. | |
| 2013/0156797 A1 | 6/2013 | Drew et al. | |
| 2013/0164296 A1 | 6/2013 | Drew et al. | |
| 2014/0294757 A1 | 10/2014 | Drew et al. | |
| 2017/0021008 A1 | 1/2017 | Drew | |

FOREIGN PATENT DOCUMENTS

| | | | |
|---|---|---|---|
| EP | 0130619 A2 | 1/1985 | |
| EP | 0156242 A2 | 10/1985 | |
| EP | 0312114 A2 | 4/1989 | |
| EP | 0376361 A2 | 7/1990 | |
| EP | 0890362 A1 | 1/1999 | |
| EP | 1946776 A1 | 7/2008 | |
| EP | 1961761 A1 | 8/2008 | |
| EP | 1133316 B1 | 1/2009 | |
| JP | 60-193925 | 10/1985 | |
| JP | 61189228 A | 8/1986 | |
| JP | H2-422 A | 1/1990 | |
| JP | H6-153926 A | 6/1994 | |
| JP | H8-505286 A | 6/1996 | |
| JP | 2003095956 A | 4/2003 | |
| JP | 2003-261591 A | 9/2003 | |
| JP | 2006-514538 A | 5/2006 | |
| JP | 2007509977 A | 4/2007 | |
| JP | 2007-524592 A | 8/2007 | |
| JP | 2008-5846 A | 1/2008 | |
| JP | 2008513438 A | 5/2008 | |
| JP | 2009510136 A | 3/2009 | |
| JP | 2009526856 A | 7/2009 | |
| JP | 2011-516608 A | 5/2011 | |
| WO | WO1989011297 * | 11/1989 | A61K 39/395 |
| WO | WO-90/05182 A1 | 5/1990 | |
| WO | WO-93/00807 A1 | 1/1993 | |
| WO | WO-94/04174 A1 | 3/1994 | |
| WO | WO-95/10605 A1 | 4/1995 | |
| WO | WO-95/11700 A1 | 5/1995 | |
| WO | WO-97/04801 A1 | 2/1997 | |
| WO | WO-97/15331 A1 | 5/1997 | |
| WO | WO-99/27071 A1 | 6/1999 | |
| WO | WO-00/29024 A1 | 5/2000 | |
| WO | WO-01/29198 A1 | 4/2001 | |
| WO | WO-01/93829 A2 | 12/2001 | |
| WO | WO-02/101412 A2 | 12/2002 | |
| WO | WO-03/035827 A2 | 5/2003 | |
| WO | WO-2004/002534 A1 | 1/2004 | |
| WO | WO-2004/007537 A2 | 1/2004 | |
| WO | WO-2004/035818 A1 | 4/2004 | |
| WO | WO-2004/105790 A1 | 12/2004 | |
| WO | WO-2004/108753 A1 | 12/2004 | |
| WO | WO-2005/042029 A2 | 5/2005 | |
| WO | WO-2005/056808 A2 | 6/2005 | |
| WO | WO-2005/062709 A2 | 7/2005 | |
| WO | WO-2006/081587 A2 | 8/2006 | |
| WO | WO-2006/085082 A1 | 8/2006 | |
| WO | WO-2006/092668 A2 | 9/2006 | |
| WO | WO-2006/094974 A2 | 9/2006 | |
| WO | WO-2006/127150 A2 | 11/2006 | |
| WO | WO-2007/035455 A2 | 3/2007 | |
| WO | WO-2007/038926 A1 | 4/2007 | |
| WO | WO2007038926 A1 * | 4/2007 | A61K 39/35 |
| WO | WO-2007/056847 A1 | 5/2007 | |
| WO | WO-2007/095337 A2 | 8/2007 | |
| WO | WO-2007/138135 A1 | 12/2007 | |
| WO | WO2007149287 A2 * | 12/2007 | C12P 21/08 |
| WO | WO-2008/051245 A2 | 5/2008 | |
| WO | WO-2008/058035 A1 | 5/2008 | |
| WO | WO-2008/114021 A1 | 9/2008 | |
| WO | WO-2008/118691 A2 | 10/2008 | |
| WO | WO-2008/150479 A2 | 12/2008 | |
| WO | WO-2009/006097 A1 | 1/2009 | |
| WO | WO-2009/015343 A2 | 1/2009 | |
| WO | WO-2009/129101 A1 | 10/2009 | |
| WO | WO-2010/035001 A1 | 4/2010 | |
| WO | WO-2010/146598 A2 | 12/2010 | |
| WO | WO2011109415 A2 * | 9/2011 | A61K 47/18 |
| WO | WO-2011/121301 A1 | 10/2011 | |
| WO | WO-2011/121305 A2 | 10/2011 | |
| WO | WO-2011/121306 A1 | 10/2011 | |

OTHER PUBLICATIONS

Arakawa et al., "Factors affecting short-term and long-term stabilities of proteins," Adv Drug Deliv Rev. 46(1-3):307-26 (2001).

Carpenter et al., "The mechanism of cryoprotection of proteins by solutes," Cryobiology. 25(3):244-55 (1988).

Chang et al., "Mechanisms of protein stabilization in the solid state," J Pharm Sci. 98(9):2886-908 (2009).

Chen et al., "Stabilization of recombinant human keratinocyte growth factor by osmolytes and salts," J Pharm Sci. 85(4):419-22 (1996).

Kim et al., "Counteracting effects of renal solutes on amyloid fibril formation by immunoglobulin light chains," J Biol Chem. 276(2):1626-33 (2001).

Lever et al., "Using high-performance liquid chromatography to measure the effects of protein-stabilizing cosolvents on a model protein and fluorescent probes," Anal Biochem. 367(1):122-33 (2007).

Maltesen et al., "Drying methods for protein pharmaceuticals," Drug Disc Today Technol. 5(2-3):e81-8 (2008).

Popova et al., "Cryoprotective effect of glycine betaine and glycerol is not based on a single mechanism," Cryo Letters. 22(5):293-8 (2001).

Roy et al., "Freeze-drying of proteins: some emerging concerns," Biotechnol Appl Biochem. 39(Pt 2):165-77 (2004).

Singh et al., "The osmoprotectants glycine and its methyl derivatives prevent the thermal inactivation of protective antigen of Bacillus anthracis," Biochem Biophys Res Commun. 316(2):559-64 (2004).
Tang et al., “Measurement of the kinetics of protein unfolding in viscous systems and implications for protein stability in freeze-drying,” Pharm Res. 22(7):1176-85 (2005).
Tang et al., “The effect of stabilizers and denaturants on the cold denaturation temperatures of proteins and implications for freeze-drying,” Pharm Res. 22(7):1167-75 (2005).
Burke et al., “Formulation, stability, and delivery of live attenuated vaccines for human use,” Crit Rev Ther Drug Carrier Syst. 16(1):1-83 (1999).
Communication pursuant to Article 94(3) EPC for European Application No. 12772389.8, dated Oct. 21, 2015 (7 pages).
Santoro et al., “Increased thermal stability of proteins in the presence of naturally occurring osmolytes,” Biochemistry. 31(23):5278-83 (1992).
Schiefner et al., “Structural basis for the binding of compatible solutes by ProX from the hyperthermophilic archaeon Archaeoglobus fulgidus,” J Biol Chem. 279(46):48270-81 (2004).
U.S. Appl. No. 13/637,828, Drew et al.
U.S. Appl. No. 13/637,913, Drew et al.
U.S. Appl. No. 14/349,481, Drew et al.
“Composition of Medium 199,” XP002596423 (2009). Retrieved from the Internet: <URL:http://www.fishersci.com/wps/downloads/segment/Scientific/pdf/cmbrex_medium_ 199.pdf>.
“Renaturation (Molecular Biology),” <http://what-when-how.com/molecular-biology/renaturation-molecular-biology/>, retrieved on Nov. 15, 2015 (2 pages).
Andersson et al., “Protein stabilising effect of polyethyleneimine” J Biotech. 72(1-2):21-31 (1999).

(56) References Cited

OTHER PUBLICATIONS

Andersson et al., "Stabilizing effect of chemical additives against oxidation of lactate dehydrogenase," Biotechnol Appl Biochem. 32:145-53 (2000).
Arakawa et al., "Factors affecting short-term and long-term stabilities of proteins ," Adv Drug Deliv Rev. 10:1-28 (1993).
Berge et al., "Preservation of enteroviruses by freeze-drying," Appl Microbiol. 22(5):850-3 (1971).
Braun et al., "Development of a freeze-stable formulation for vaccines containing aluminum salt adjuvants," Vaccine. 27(1):72-9 (2009).
Brown et al., "Assembly of hybrid bacteriophage Qbeta virus-like particles," Biochemistry. 48(47):11155-7 (2009).
Bryjak et al., "Storage stabilization and purification of enzyme by water-soluble synthetic polymers," Enzyme Microb Technol. 16:616-21 (1994).
Bryjak, "Storage stabilization of enzyme activity by poly(ethyleneimine)," Bioprocess Eng. 13:177-81 (1995).
Cleland et al., "Glycine betaine as a cryoprotectant for prokaryotes," J Microbiol Methods. 58(1):31-8 (2004).
Cosquer et al., "Nanomolar levels of dimethylsulfoniopropionate, dimethylsulfonioacetate, and glycine betaine are sufficient to confer osmoprotection to *Escherichia coli*," Appl Environ Microbiol. 65(8):3304-11 (1999).
Costantino et al., "Effect of excipients on the stability and structure of lyophilized recombinant human growth hormone," J Pharma Sci. 87(11):1412-20 (1998).
Drew et al., "Stable vaccine technology," displayed in Vienna 3 to Oct. 5, 2010.
Foreman et al., "Effects of charged water-soluble polymers on the stability and activity of yeast alcohol dehydrogenase and subtilisin Carlsberg," Biotechnol Bioeng. 76(3):241-6 (2001).
Greiff et al., "Effects of freezing, storage at low temperatures, and drying by sublimation in vacuo on the activities of measles virus," Nature. 202:624-5 (1964).
Gupta et al., "Stabilization of respiratory syncytial virus (RSV) against thermal inactivation and freeze-thaw cycles for development and control of RSV vaccines and immune globulin," Vaccine. 14(15):1417-20 (1996).
Holtmann et al., "Thermoprotection of Bacillus subtilis by exogenously provided glycine betaine and structurally related compatible solutes: involvement of Opu transporters," J Bacteriol. 186(6):1683-93 (2004).
Hubálek, "Protectants used in the cryopreservation of microorganisms," Cryobiology. 46(3):205-29 (2003).
Izutsu, "Stabilization of therapeutic proteins by chemical and physical methods" in *Therapeutic Proteins, Smales and James ed.* Humana Press ISBN 1-58829-390-4, 287-292 (2005).
Land et al., "The Challenges of Antimicrobial Preservation of a Sugar-free Liquid Risedronate Sodium Formulation for US and EMEA Pediatric Use," Post No. M1187. Procter & Gamble Pharmaceuticals, 2009 AAPS Natual Meeting and Exposition, Los Angeles, CA (2009).
Larski et al., "Stabilization of Newcastle disease virus by dimethyl sulfoxide," Acta Virol. 16(4):349-52 (1972).
Liao et al., "Influence of the active pharmaceutical ingredient concentration on the physical state of mannitol—implications in freeze-drying," Pharm Res. 22(11):1978-85 (2005). Abstract provided.
Liao et al., "Protective mechanism of stabilizing excipients against dehydration in the freeze-drying of proteins," Pharm Res. 19(12):1854-61(2002).
Lloyd et al., "A comparison of glycine, sarcosine, N,N-dimethylglycine, glycinebetaine and N-modified betaines as liposome cryoprotectants" J Pharm Pharmacol. 44(6):507-11 (1992).
Manual of Policies and Procedures, Center for Drug Evaluation and Research, "Applications for Parenteral Products in Plastic Immediate Containers," MAPP 6020.2 (2007).
McGann et al., "Cryoprotection by dimethyl sulfoxide and dimethyl sulfone," Cryobiology. 24(1):11-6 (1987).
Nishiguchi et al., "Temperature- and concentration-dependence of compatibility of the organic osmolyte beta-dimethylsulfoniopropionate," Cryobiology. 29(1):118-24 (1992).
Paleg et al., "Proline and glycine betaine influence protein solvation," Plant Physiol. 75(4):974-8 (1984).
Peek et al., "A rapid, three-step process for the preformulation of a recombinant ricin toxin A-chain vaccine," J Pharm Sci. 96(1):44-60 (2007).
Rathore et al., "Current perspectives on stability of protein drug products during formulation, fill and finish operations." Biotechnol Prog. 24(3):504-14 (2008).
Reichert et al., "Development trends for monoclonal antibody cancer therapeutics," Nat Rev Drug Discov. 6(5):349-56 (2007).
Sigalov, "Cryopreservation and long-term storage of human low density lipoproteins," Eur J Clin Chem Clin Biochem. 33(2):73-80 (1995).
Sjölander et al., "ISCOMs: an adjuvant with multiple functions," J Leukoc Biol. 64(6):713-23 (1998).
Stabilitech: "Stabilitech Technology," Innovations in Health. XP002635295. Nov. 19, 2009 (21 pages).
Suntanto et al., "Home delivery of heat-stable vaccines in Indonesia: outreach immunization with a prefilled single-use injection device" Bull World Health Organ. 77(2):119-26 (1999).
Tesconi et al., "Freeze-drying above room temperature," J Pharm Sci. 88(5):501-6 (1999).
The class notes from Indiana University on viral structure, http://courses.bio.indiana.edu/M430-Taylor/structure.html, retrieved on Apr. 13, 2015 (5 pages).
Tiyaboonchai et al., "Insulin containing polyethylenimine-dextran sulfate nanoparticles," Int J Pharm. 255(1-2):139-51 (2003).
Vasudevamurthy et al., "Enzyme stabilization using synthetic compensatory solutes" Biocat and Biotransform. 23(3/4):285-91 (2005).
Wallis et al., "Stabilization of enveloped viruses by dimethyl sulfoxide," J Virol. 2(9):953-4 (1968).
Wolff et al., "Protection of aluminum hydroxide during lyophilisation as an adjuvant for freeze-dried vaccines," Colloids and Surfaces A: Physicochem. Eng Aspects. 330:116-26 (2008).
Wolff et al., "Comparative stability study of lyophilised aluminium hydroxide adjuvanted vaccine formulations containing a monoclonal antibody as a model antigen and methods used for their characterisation," Colloids and Surfaces A: Physicochem. Eng Aspects. 339:82-93 (2009).
Wolff et al.,"Development of a formulation protecting aluminum hydroxide adjuvanted vaccines during lyophilisation," 6th World Meeting on Pharmaceutics, Biopharmaceutics and Pharmaceutical Technology, Barcelona, 7th to 10th of Apr. 2008.
Yancey, "Organic osmolytes as compatible, metabolic and counteracting cytoprotectants in high osmolarity and other stresses," J Exp Biol. 208:2819-30 (2005).
Breteler, "The MSM Miracle," available <http://www.msm-info.com/>, Jul. 2001 (12 pages).
Ishimaru et al., "Pressure-inactivated FMDV: a potential vaccine," Vaccine. 22(17-18):2334-9 (2004).
Mateu, "Assembly, stability and dynamics of virus capsids," Arch Biochem Biophys. 531(1-2):65-79 (2013).

* cited by examiner

STABILISATION OF POLYPEPTIDES

CROSS-REFERENCE TO RELATED APPLICATIONS

This application is the U.S. national stage filing under 35 U.S.C. § 371 of international application PCT/GB2012/052477, filed Oct. 5, 2012, which claims priority from Great Britain Patent Application No. 1117233.5, filed Oct. 5, 2011.

FIELD OF THE INVENTION

The invention relates to the stabilisation of polypeptides.

BACKGROUND TO THE INVENTION

Some biological molecules are sufficiently stable that they can be isolated, purified and then stored in solution at room temperature. However, this is not possible for many materials and techniques involving storage at low temperature, addition of stabilizers or cryoprotectants, freeze-drying, vacuum-drying and air-drying have been tried to ensure shelf preservation.

Despite the availability of these techniques, some biological materials still show unsatisfactory levels of stability during storage and some techniques lead to added cost and inconvenience. For example, refrigerated transportation and storage is expensive, and any breaks in temperature control can result in reduced efficacy of the biological molecule. Further, refrigerated transport is often not available for the transport of medicines in countries in the developing world.

Also, the stresses of freeze-drying or lyophilisation can be very damaging to some biological materials. Freeze drying of biopharmaceuticals involves freezing solutions or suspensions of thermosensitive biomaterials, followed by primary and secondary drying. The technique is based on sublimation of water at subzero temperature under vacuum without the solution melting. Freeze-drying represents a key step for manufacturing solid protein and vaccine pharmaceuticals. The rate of water vapour diffusion from the frozen biomaterial is very low and therefore the process is time-consuming. Additionally, both the freezing and drying stages introduce stresses that are capable of unfolding or denaturing proteins.

WO 90/05182 describes a method of protecting proteins against denaturation on drying. The method comprises the steps of mixing an aqueous solution of the protein with a soluble cationic polyelectrolyte and a cyclic polyol and removing water from the solution. Diethylaminoethyldextran (DEAE-dextran) and chitosan are the preferred cationic polyelectrolytes, although polyethyleneimine is also mentioned as suitable.

WO-A-2006/0850082 reports a desiccated or preserved product comprising a sugar, a charged material such as a histone protein and a desiccation- or thermo-sensitive biological component. The sugar forms an amorphous solid matrix. However, the histone may have immunological consequences if the preserved biological component is administered to a human or animal.

WO 2008/114021 describes a method for preserving viral particles. The method comprises drying an aqueous solution of one or more sugars, a polyethyleneimine and the viral particles to form an amorphous solid matrix comprising the viral particles. The aqueous solution contains the polyethyleneimine at a concentration of 15 μM or less based on the number-average molar mass ($M_n$) of the polyethyleneimine and the sugar concentration or, if more than one sugar is present, total sugar concentration is greater than 0.1M.

WO 2010/035001 describes a method for preserving polypeptides. The method comprises drying an aqueous solution of one or more sugars, a polyethyleneimine and the polypeptide to form an amorphous solid matrix comprising the polypeptide. The aqueous solution contains the polyethyleneimine at a concentration of 25 μM or less based on the number-average molar mass ($M_n$) of the polyethyleneimine and the sugar concentration or, if more than one sugar is present, total sugar concentration is greater than 0.1M.

SUMMARY OF THE INVENTION

The present inventors have found that polypeptide preparations are preserved stabley by compounds of formula (I) and/or (II) as defined herein or physiologically acceptable salts or esters thereof and one or more sugars during drying. Polypeptide activity was preserved following subsequent heat challenge. Polypeptide activity may also be preserved in the aqueous solution prior to drying.

Accordingly, the present invention provides a method for preserving a polypeptide comprising:

(a) providing an aqueous solution of (i) the polypeptide, (ii) one or more sugars, and (iii) a compound of formula (I) or a physiologically acceptable salt or ester thereof

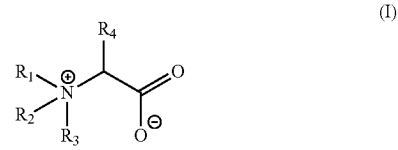

wherein:
   $R_1$ represents hydrogen or $C_{1-6}$ alkyl; and
   $R_4$ represents hydrogen; or
   $R_1$ and $R_4$ together with the atoms to which they are attached form a pyrrolidine ring;
   $R_2$ represents hydrogen, $C_{1-6}$ alkyl or —$(CH_2)_{2-5}$NHC(O)$(CH_2)_{5-15}CH_3$; and
   $R_3$ represents $C_{1-6}$ alkyl; and/or
   a compound of formula (II) or a physiologically acceptable salt or ester thereof

wherein:
   X represents —S(O)$_2$— or —S$^+$(R$_c$)—;
   $R_a$ and $R_b$ independently represent $C_{1-6}$ alkyl; and
   $R_c$ represents $C_{1-6}$ alkyl substituted with a carboxylate anion and with an amine (—NH$_2$) moiety; and (b) drying the solution to form a composition incorporating the polypeptide.

The invention further provides:
   a composition which comprises a compound of formula (I) or a physiologically acceptable salt or ester thereof and/or a compound of formula (II) or a physiologically acceptable salt or ester thereof and one or more sugars and which incorporates a polypeptide;

a composition obtainable by a method of the invention;
vaccine comprising a composition of the invention in which the polypeptide is a vaccine immunogen and optionally an adjuvant;
a composition of the invention in which the polypeptide is a vaccine immunogen for use as a vaccine;
a method of preparing a vaccine which incorporates a vaccine immunogen, which method comprises: (a) providing an aqueous solution of (i) a vaccine immunogen, (ii) a compound of formula (I) or a physiologically acceptable salt or ester thereof and/or a compound of formula (II) or a physiologically acceptable salt or ester thereof and (iii) one or more sugars; and (b) optionally adding an adjuvant, buffer, antibiotic and/or additive to the admixture; and (c) drying the solution to form a composition or solid composition incorporating said vaccine immunogen;
use of a compound of formula (I) or a physiologically acceptable salt or ester thereof and/or a compound of formula (II) or a physiologically acceptable salt or ester thereof and one or more sugars for preserving a polypeptide;
a method for preserving a polypeptide prior to drying comprising: (a) providing an aqueous solution of (i) a polypeptide, (ii) one or more sugars, and (iii) a compound of formula (I) or a physiologically acceptable salt or ester thereof and/or a compound of formula (II) or a physiologically acceptable salt or ester thereof; and (b) storing the solution for up to five years in a sealed container, optionally in a refrigerator or freezer.
a bulk aqueous solution comprising (i) a polypeptide, (ii) one or more sugars, and (iii) a compound of formula (I) or a physiologically acceptable salt or ester thereof and/or a compound of formula (II) or a physiologically acceptable salt or ester thereof, which solution is provided in a sealed container and is stored prior to drying in a refrigerator or freezer;
use of a compound of formula (I) or a physiologically acceptable salt or ester thereof and/or a compound of formula (II) or a physiologically acceptable salt or ester thereof and one or more sugars for preserving a polypeptide in an aqueous solution which comprises said polypeptide, prior to drying; and
use of a compound of formula (I) or a physiologically acceptable salt or ester thereof and/or a compound of formula (II) or a physiologically acceptable salt or ester thereof and one or more sugars as a resuspension agent for a composition which is a dried or freeze-dried product comprising a polypeptide.

The cross marks the predicted optimum.

Figure 16:
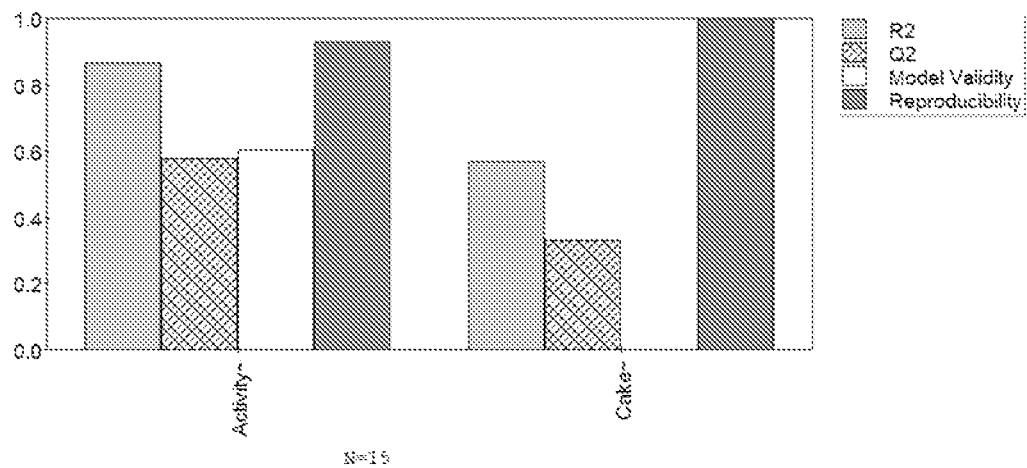

FIG. 16 shows a summary of the statistics of the model used to represent the data in Example 7. "Activity" represents model for response=% recovered activity, "Cake" represents model for response=cake quality. In general a value of 1 for each measure implies perfection. $R^2$=coefficient of determination—a measure of goodness of fit. $R^2$<0.5=low model significance. $Q^2$=estimate of prediction precision—a measure of goodness of prediction. $Q^2$ should be >0.1 for a significant model. $Q^2$ should be >0.5 for a good model. $R^2$-$Q^2$ should be <0.2 to 0.3. Model validity="a test of diverse model problems". Model validity <0.25=indicator of statistically significant model problems e.g. outliers, incorrect model/transformation. Reproducibility=measure of variation between replicates compared to over- all variability. Reproducibility >0.5 implies significance.

Figure 17:
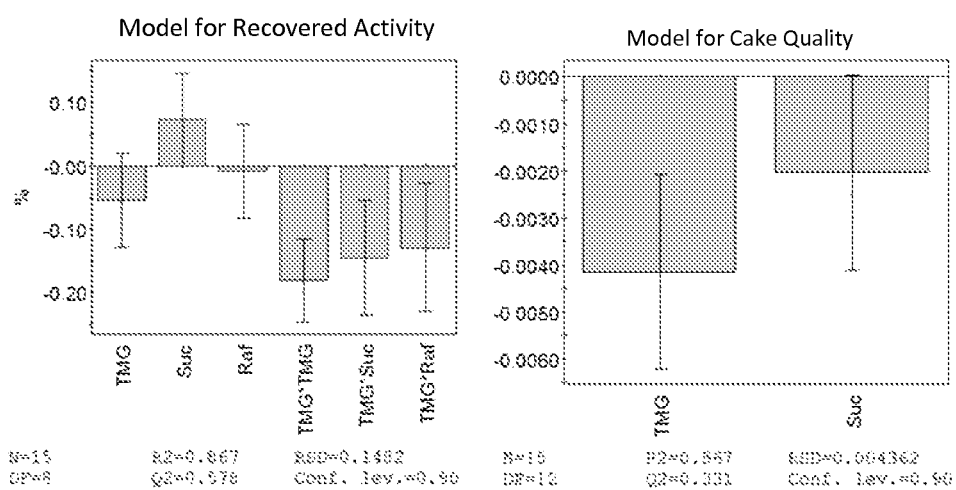
Figure 18:
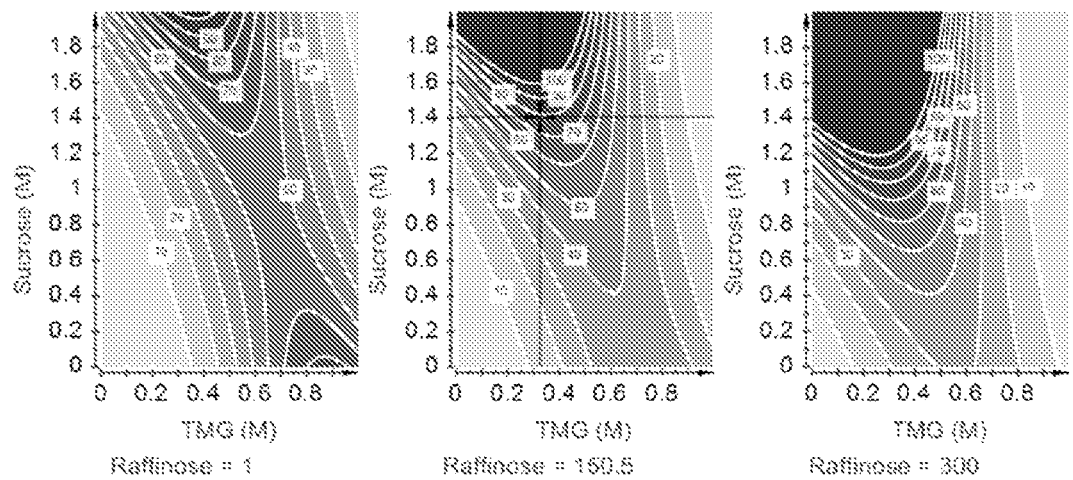

FIG. 17 shows the terms retained in the model after fine tuning in Example 7. Error bars not crossing the origin indicate a significant factor at the 90% C.I FIG. 18 shows a 4D contour plot showing the predicted recovered G-CSF activity with varying formulation in Example 7. Plots are centred around the Monte-Carlo generated optimum. The cross marks the predicted optimum.

Figure 19:
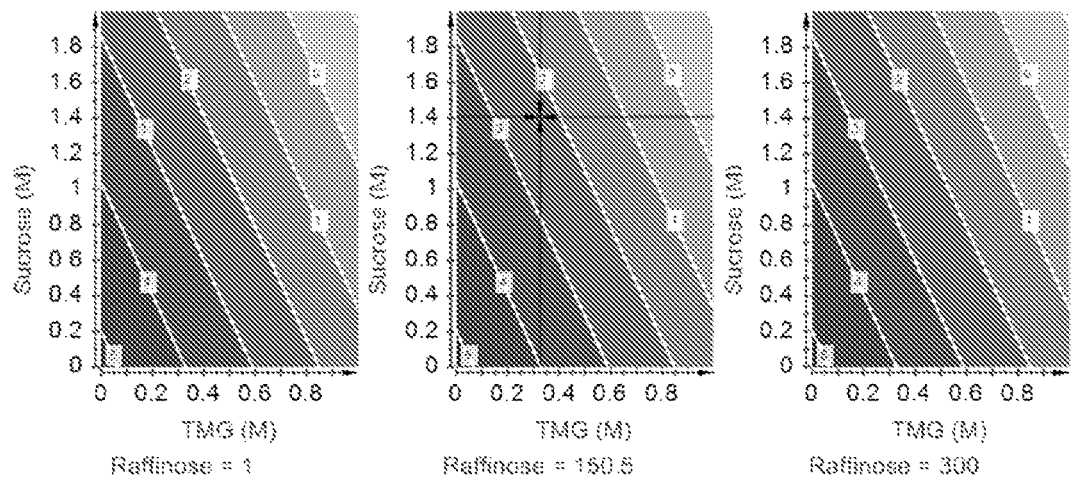
Figure 20:
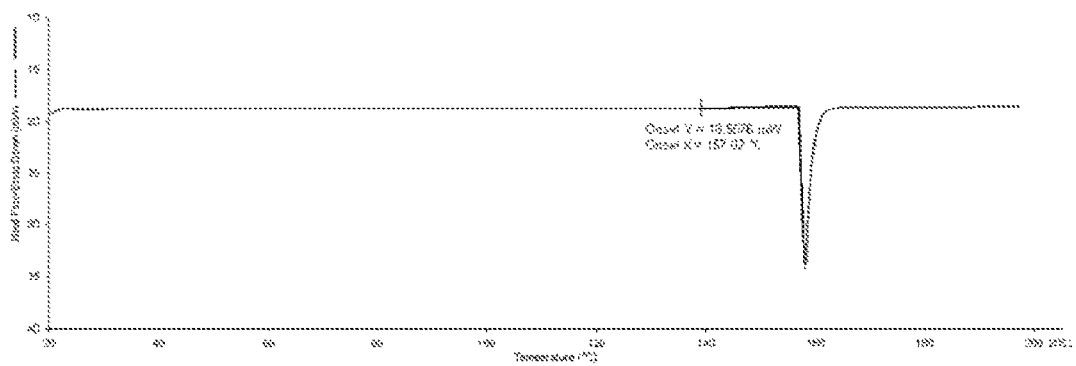

FIG. 19 shows a 4D contour plot showing the predicted cake quality with varying formulation in Example 7. Plots are centred around the Monte-Carlo generated optimum. The cross marks the predicted optimum FIGS. 20 to 25 show the differential scanning calorimetry results from Example 8.

Figure 26:
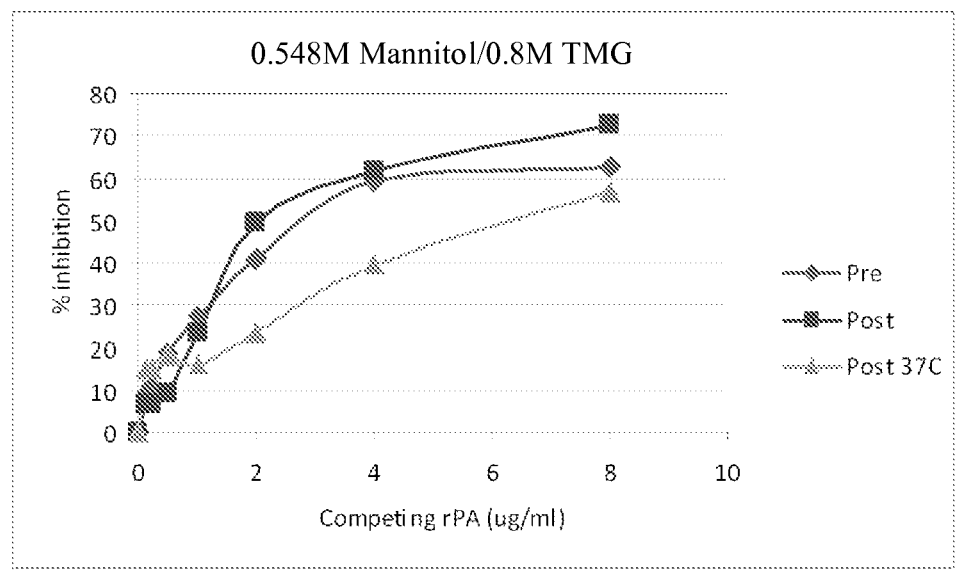

FIG. 26 shows the recombinant protective antigen (rPA) activity for 0.548M mannitol and 0.8M TMG in Example 9.

Figure 27:
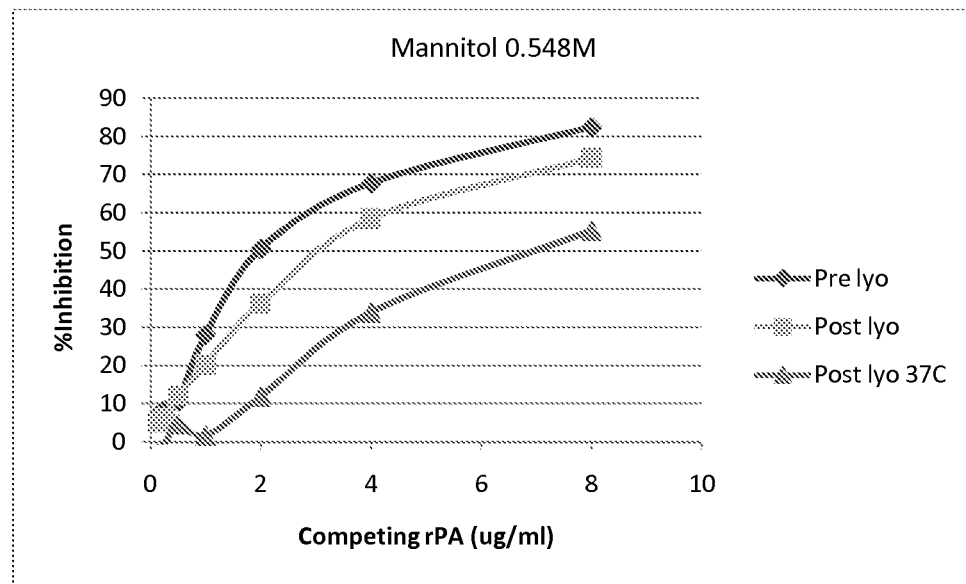

FIG. 27 shows the recombinant protective antigen (rPA) activity for 0.548M mannitol in Example 9.

Figure 28:
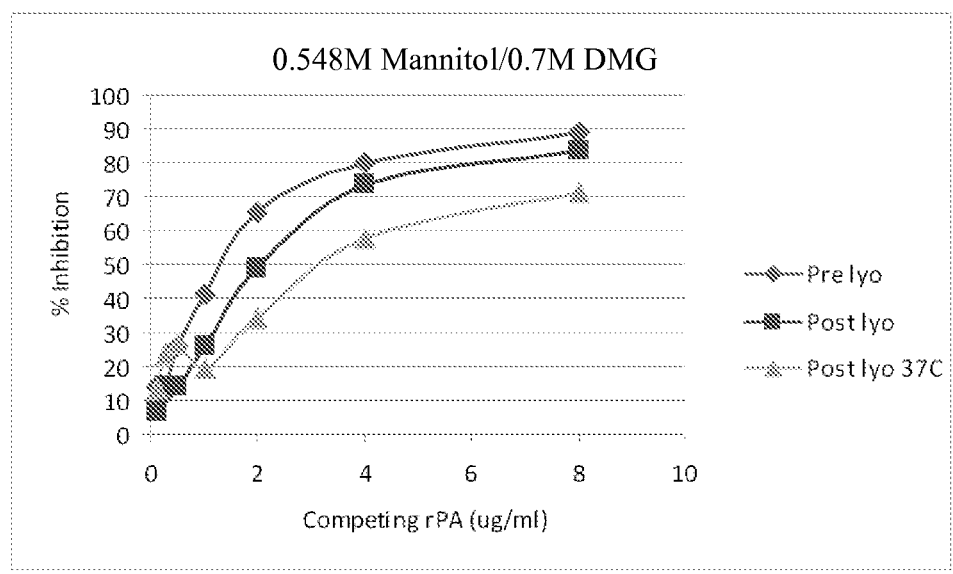

FIG. 28 shows the recombinant protective antigen (rPA) activity for 0.548M mannitol and 0.7M DMG in Example 10.

Figure 29:
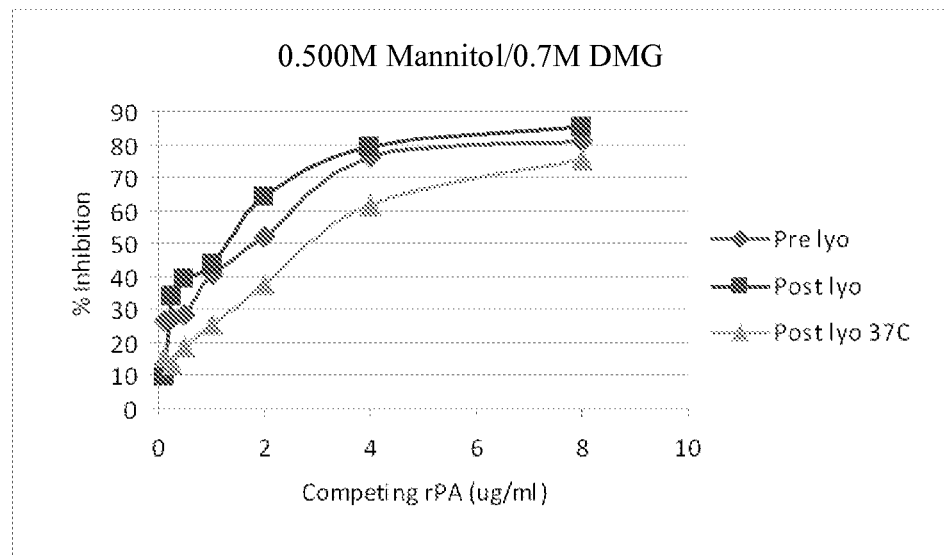

FIG. 29 shows the recombinant protective antigen (rPA) activity for 0.5M mannitol and 0.7M DMG in Example 10.

Figure 30:
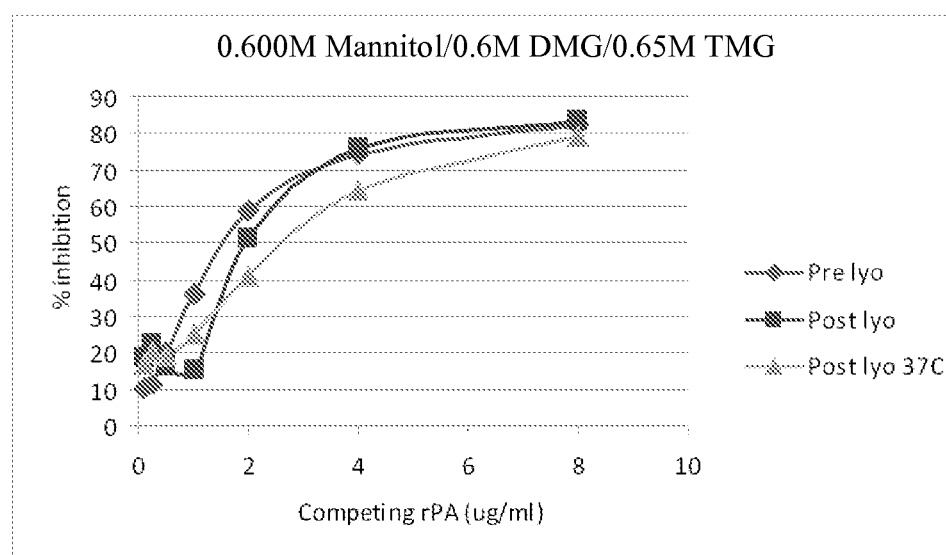

FIG. 30 shows the recombinant protective antigen (rPA) activity for 0.6M mannitol, 0.6M DMG and 0.65M TMG in Example 10.

Figure 31:
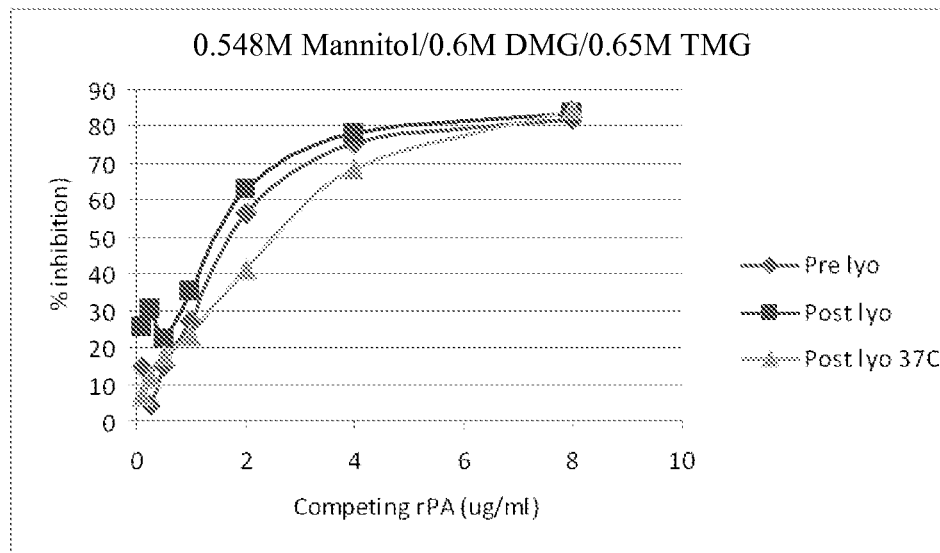

FIG. 31 shows the recombinant protective antigen (rPA) activity for 0.548M mannitol, 0.6M DMG and 0.65M TMG in Example 10.

Figure 32:
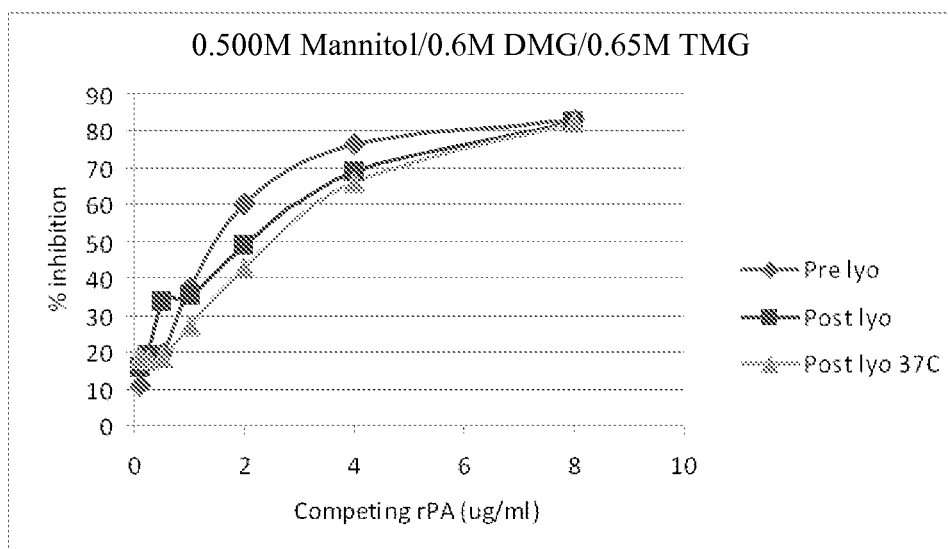

FIG. 32 shows the recombinant protective antigen (rPA) activity for 0.5M mannitol, 0.6M DMG and 0.65M TMG in Example 10.

Figure 33:
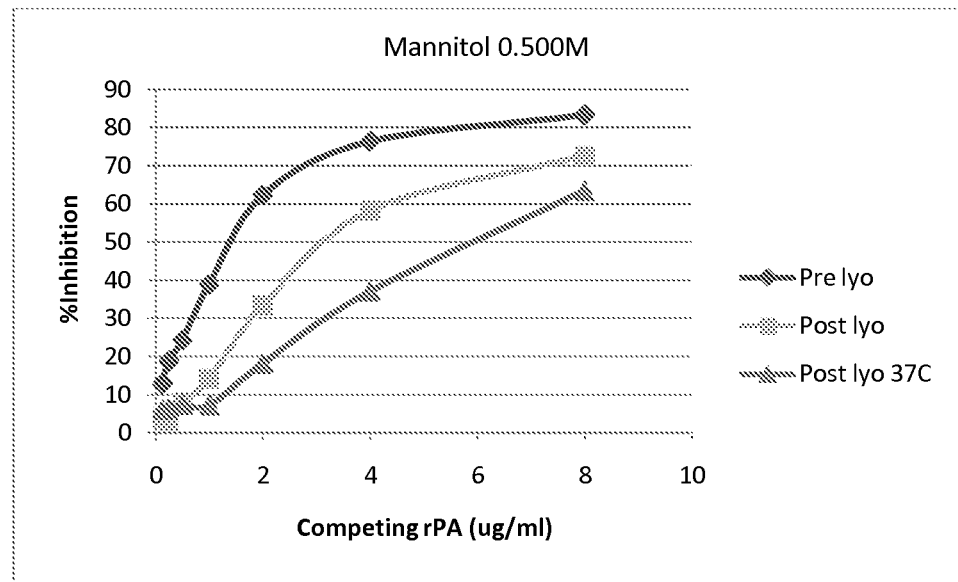

FIG. 33 shows the recombinant protective antigen (rPA) activity for 0.5M mannitol in Example 10.

Figure 34:
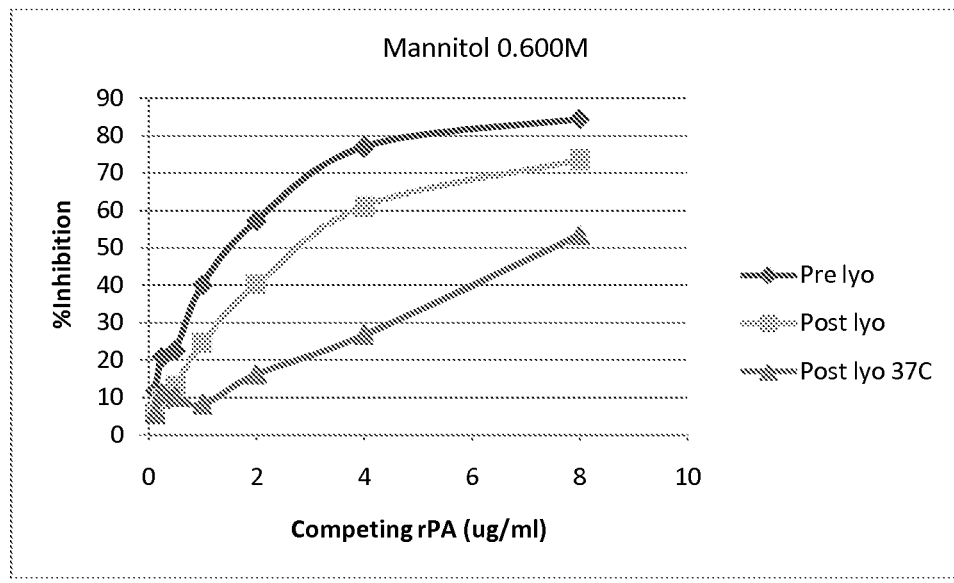

FIG. 34 shows the recombinant protective antigen (rPA) activity for 0.6M mannitol in Example 10.

FIGS. 35 to 38 shows the differential scanning calorimetry results from Example 11

Figure 39:
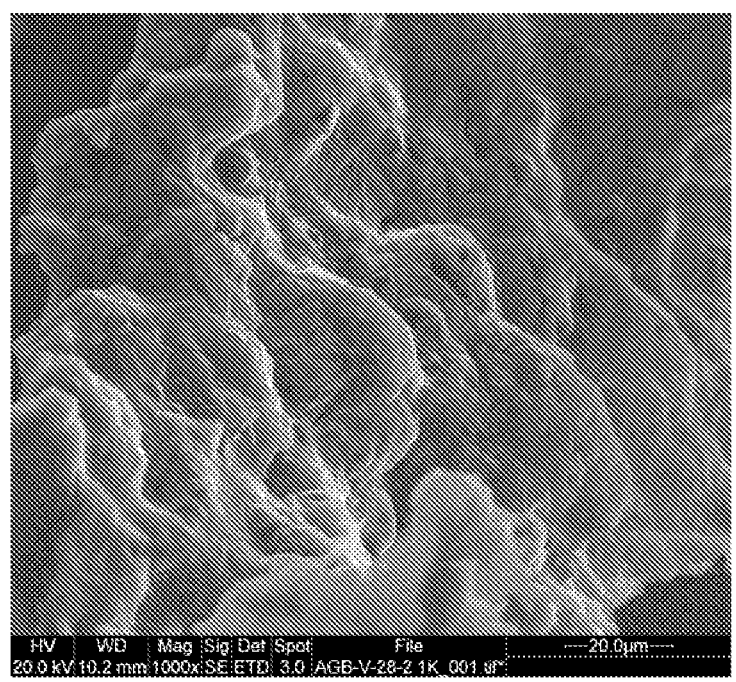

FIG. 39 shows an SEM image for freeze-dried sample 5 (0.5M DMG, 0.5M mannitol) prepared in Example 11.

DETAILED DESCRIPTION OF THE INVENTION

Summary

The present invention relates to the preservation of a polypeptide by a compound of formula (I) or a physiologically acceptable salt or ester thereof and/or a compound of formula (II) or a physiologically acceptable salt or ester thereof and one, two or more sugars. The polypeptide is contacted with the compound of formula (I) or a physiologically acceptable salt or ester thereof and/or compound of formula (II) or a physiologically acceptable salt or ester thereof and one or more sugars in an aqueous solution and the resulting solution in which the polypeptide is present is then dried to form a composition incorporating the polypeptide.

The polypeptide may therefore be admixed with an aqueous solution ("preservation mixture") of the compound of formula (I) or a physiologically acceptable salt or ester thereof and/or compound of formula (II) or a physiologically acceptable salt or ester thereof and one or more sugars. The resulting solution is then dried to form a composition incorporating the polypeptide. The dried composition may take the form of a cake or powder. The cake can be milled to a powder if required.

The invention enables polypeptide structure and function to be preserved during the drying step. Polypeptide activity following drying can thus be maintained. The presence of a compound of formula (I) or a physiologically acceptable salt or ester thereof and/or a compound of formula (II) or a physiologically acceptable salt or ester thereof alone allows preservation of polypeptide activity. Further improvements in preservation of polypeptide activity can be achieved by use of one or more sugars in combination with a compound of formula (I) or a physiologically acceptable salt or ester thereof and/or a compound of formula (II) or a physiologically acceptable salt or ester thereof.

The preserved polypeptide demonstrates improved thermal resistance allowing extension of shelf life, ease of storage and transport and obviating the need for a cold chain for distribution. The invention can thus provide protection as a cryoprotectant (protection against freeze damage), lyoprotectant (protection during freeze-drying) and/or a thermoprotectant (protection against temperatures higher or lower than 4° C.).

In addition, the polypeptide is preserved in the aqueous solution prior to the drying step. This allows the aqueous solution to be stored after preparation, until such time as the drying step can be carried out, without undue loss of polypeptide activity.

Polypeptides

Any polypeptide such as a physiologically active polypeptide is suitable for use in the invention. For example, the polypeptide may be a small peptide of less than 15 amino acids such as 6 to 14 amino acids (e.g. oxytocin, cyclosporin), a larger peptide of between 15 and 50 amino acids (e.g. calcitonin, growth hormone releasing hormone 1-29 (GHRH)), a small protein of between 50 and 250 amino acids in length (e.g. insulin, human growth hormone), a larger protein of greater than 250 amino acids in length or a multisubunit protein comprising a complex of two or more polypeptide chains.

Typically, the polypeptide is a hormone, growth factor, peptide or cytokine; an antibody or antigen- or ligand-binding fragment thereof; an oxidoreductase, a transferase, a hydrolase, a lyase, an isomerase or a ligase; or a vaccine immunogen.

The polypeptide may be a peptide hormone, growth factor or cytokine. It may be an antigen-binding polypeptide, receptor inhibitor, ligand mimic or receptor blocking agent. Typically, the polypeptide is in substantially pure form. It may thus be an isolated polypeptide. For example, the polypeptide may be isolated following recombinant production.

For example, the polypeptide may be a hormone selected from a growth hormone (GH), prolactin (PRL), a human placental lactogen (hPL), a gonadotrophin (e.g. lutenising hormone, follicle stimulating hormone), a thyroid stimulating hormone (TSH), a member of the pro-opiomelanocortin (POMC) family, vasopressin and oxytocin, a natriuretic hormone, parathyroid hormone (PTH), calcitonin, insulin, a glucagon, somatostatin and a gastrointestinal hormone.

The polypeptide may be a Tachykinin peptide (e.g. Substance P, Kassinin, Neurokinin A, Eledoisin, Neurokinin B), a vasoactive intestinal peptide (e.g. VIP (Vasoactive Intestinal Peptide; PHM27), PACAP (Pituitary Adenylate Cyclase Activating Peptide), Peptide PHI 27 (Peptide Histidine Isoleucine 27), GHRH 1-24 (Growth Hormone Releasing Hormone 1-24), Glucagon, Secretin), a pancreatic polypeptide-related peptide (e.g. NPY, PYY (Peptide YY), APP (Avian Pancreatic Polypeptide), PPY (Pancreatic PolYpeptide), an opioid peptide (e.g. Proopiomelanocortin (POMC) peptides, Enkephalin pentapeptides, Prodynorphin peptide, a calcitonin peptide (e.g. Calcitonin, Amylin, AGG01) or another peptide (e.g. B-type Natriuretic Peptide (BNP)).

The polypeptide may be a growth factor selected from a member of the epidermal growth factor (EGF) family, platelet-derived growth factor family (PDGF), fibroblast growth factor family (FGF), Transforming Growth Factors-β family (TGFs-β), Transforming Growth Factor-α (TGF-α), Erythropoietin (Epo), Insulin-Like Growth Factor-I (IGF-I), Insulin-Like Growth Factor-II (IGF-II). Typically, the growth factor is a Transforming growth factor beta (TGF-β), a Nerve growth factor (NGF), a Neurotrophin, a Platelet-derived growth factor (PDGF), Erythropoietin (EPO), Thrombopoietin (TPO), Myostatin (GDF-8), a Growth differentiation factor-9 (GDF9), Acidic fibroblast growth factor (aFGF or FGF-1), Basic fibroblast growth factor (bFGF or FGF-2), Epidermal growth factor (EGF) or a Hepatocyte growth factor (HGF).

The polypeptide may be a cytokine selected from Interleukin-1 (IL-1), Interleukin-2 (IL-2), Interleukin-6 (IL-6) Interleukin-8 (IL-8), Tumor Necrosis Factor-α (TNF-α), Tumor Necrosis Factor-β (TNF-β), Interferon-γ (INF-γ) and a Colony Stimulating Factor (CSF). Typically the cytokine is a Granulocyte-colony stimulating factor (G-CSF) or a Granulocyte-macrophage colony stimulating factor (GM-CSF).

The polypeptide may be a blood-clotting factor such as Factor VIII, Factor V, von Willebrand factor or coagulation factor III.

Typically, the polypeptide is not (a) luciferase, an analogue of luciferase showing luciferase like activity, or apyrase, and/or (b) Factor VIIa, Antibodies An antibody for use in the invention may either be a whole antibody or an antigen- or ligand-binding fragment thereof Whole Antibodies In one embodiment, the antibody is an immunoglobulin (Ig) monomer, dimer, tetramer, pentamer, or other oligomer. Each antibody monomer may comprise four polypeptide chains (for example, a conventional antibody consisting of two identical heavy chains and two identical light chains). Alternatively, each antibody monomer consists of two polypeptide chains (for example, a heavy chain antibody consisting of two identical heavy chains).

The antibody can be any class or isotype of antibody (for example IgG, IgM, IgA, IgD or IgE) or any subclass of antibody (for example IgG subclasses IgG1, IgG2, IgG3, IgG4 or IgA subclasses IgA1 or IgA2). Typically, the antibody is an IgG such as an IgG1, IgG2 or IgG4 antibody. Usually, the antibody is an IgG1 or IgG2 antibody.

Typically the antibody or antigen-binding fragment is of mammalian origin. The antibody may thus be a primate, human, rodent (e.g. mouse or rat), rabbit, ovine, porcine, equine or camelidae antibody or antibody fragment. The antibody or antibody fragment may be of shark or chicken origin.

The antibody may be a monoclonal or polyclonal antibody. Monoclonal antibodies are obtained from a population of substantially homogenous antibodies that are directed against a single determinant on the antigen. A population of polyclonal antibodies comprises a mixture of antibodies directed against different epitopes.

Antigen- or Ligand-binding Fragments

The antigen-binding fragment can be any fragment of an antibody which retains antigen- or ligand-binding ability, for example a Fab, F(Ab')$_2$, Fv, disulphide-linked Fv, single chain Fv (scFv), disulphide-linked scFv, diabody, linear antibody, domain antibody or multispecific antibody. Such fragments comprise one or more antigen or ligand binding sites. In one embodiment, the antigen- or ligand-binding fragment comprises four framework regions (e.g. FR1, FR2, FR3 and FR4) and three complementarity-determining regions (e.g. CDR1, CDR2 and CDR3). Methods suitable for detecting ability of a fragment to bind an antigen or ligand are well known in the art, for example immunoassays and phage display.

The antibody or binding fragment may be a monospecific, bispecific or multispecific antibody. A multispecific antibody has binding specificity for at least one, at least two, at least three, at least four or more different epitopes, antigens or ligands A bispecific antibody is able to bind to two different epitopes, antigens or ligands. For example, a bispecific antibody may comprise two pairs of $V_H$ and $V_L$, each $V_H/V_L$ pair binding to a single antigen or epitope. Methods for preparing bispecific antibodies are known in the art, for example involving coexpression of two immunoglobulin heavy chain-light chain pairs, fusion of antibody variable domains with the desired binding specificities to immunoglobulin constant domain sequences, or chemical linkage of antibody fragments.

The bispecific antibody "diabody" comprises a heavy chain variable domain connected to a light chain variable domain in the same polypeptide chain ($V_H$-$V_L$). Diabodies can be generated using a linker (e.g. a peptide linker) that is too short to allow pairing between the two domains on the same chain, so that the domains are forced to pair with the complementary domains of another chain and create a dimeric molecule with two antigen- or ligand-binding sites.

A suitable scFv antibody fragment may comprise $V_H$ and $V_L$ domains of an antibody wherein these domains are present in a single polypeptide chain. Generally, the Fv polypeptide further comprises a polypeptide linker between the $V_H$ and $V_L$ domains, which enables the scFv to form the desired structure for antigen binding.

A domain antibody for use in the methods of the invention may essentially consist of a light chain variable domain (e.g. a $V_L$) or of a heavy chain variable domain (e.g. a $V_H$). The heavy chain variable domain may be derived from a conventional four-chain antibody or from a heavy chain antibody (e.g. a camelidae $V_{HH}$).

Modifications

The whole antibody or fragment thereof may be associated with other moieties, such as linkers, which may be used to join together two or more fragments or antibodies. Such linkers may be chemical linkers or can be present in the form of a fusion protein with a fragment or whole antibody. The linkers may thus be used to join together whole antibodies or fragments, which have the same or different binding specificities.

In a further embodiment, the antibody or antigen- or ligand-binding fragment is linked to a further moiety such as a toxin, therapeutic drug (e.g. chemotherapeutic drug), radioisotope, liposome or prodrug-activating enzyme. The type of further moiety will depend on the end use of the antibody or antigen-binding fragment.

The antibody or antigen- or ligand-binding fragment may be linked to one or more small molecule toxins (e.g. calicheamicin, maytansine, trichothene and CC1065) or an enzymatically active toxin or fragment thereof (e.g. *diphtheria* toxin, exotoxin A chain from *Pseudomonas aeruginosa*, ricin A chain, abrin A chain, modeccin A chain, alpha-sarcin, *Aleurites fordii* proteins, dianthin proteins, curcin, crotin, gelonin, mitogellin, restrictocin, phenomycin, enomycin or tricothecenes).

Radioisotopes suitable for linking to the antibody or antigen-binding fragments include, but are not limited to $Tc^{99}$, $At_{211}$, $I^{131}$, $I^{125}$, $Y^{90}$, $Re^{186}$, $Re^{188}$, $Sm^{153}$, $Bi^{212}$ and $P^{32}$.

The antibody or antigen- or ligand-binding fragment may be linked for example, to a prodrug-activating enzyme that converts or is capable of converting a prodrug to an active anti-cancer drug. For example, alkaline phosphatase can be used to convert phosphate-containing prodrugs into free drugs, arylsufatase may be used to convert sulfate-containing prodrugs into free drugs, cytosine deaminase may be used to convert non-toxic 5-fluorocytosine into the anti-cancer drug 5-fluorouracil; and proteases such as serratia protease, thermolysin, subtilisin, carboxypeptidases and cathepsins are useful for converting peptide-containing prodrugs into free drugs. The enzyme may be a nitroreductase which has been identified as useful in the metabolism of a number of prodrugs in anti-cancer gene therapy. Alternatively, antibodies or antigen- or ligand-binding fragments with enzymatic activity can be used to convert prodrugs into free active drugs.

A suitable chemotherapeutic agent may include, but is not limited to an alkylating agent such as thiotepa and cyclosphosphamide; an alkyl sulfonate such as busulfan, improsulfan and piposulfan; an aziridine such as benzodopa, carboquone, meturedopa and uredopa; a nitrogen mustard such as chlorambucil, chlornaphazine, ifosfamide, melphalan; a nitrosurea such as carmustin and fotemustine; an anti-metabolite such as methotrexate and 5-fluorouracil (5-FU); a folic acid analogue such as denopterin and pteropterin; a purine analogue such as fludarabine and thiamiprine; a pyrimidine analogue such as ancitabine, azacitidine, carmofur and doxifluridine; a taxoid such as paclitaxel and doxetaxel; and pharmaceutically acceptable salts, acids or derivatives of any of the above.

In another embodiment, the antibody or antibody fragment may be PEGylated. Thus, one or more polyethylene glycol molecules may be covalently attached to the antibody molecule or antibody fragment molecule. From one to three polyethylene glycol molecules may be covalently attached to each antibody molecule or antibody fragment molecule. Such PEGylation is predominantly used to reduce the immunogenicity of an antibody or antibody fragment and/or increase the circulating half-life of the antibody or antibody fragment.

Chimeric, Humanized or Human Antibodies

In one embodiment the antibody or antigen- or ligand-binding fragment is a chimeric antibody or fragment thereof comprising sequence from different natural antibodies. For example, the chimeric antibody or antibody fragment may comprise a portion of the heavy and/or light chain identical or homologous to corresponding sequences in antibodies of a particular species or antibody class, while the remainder of the chain is identical or homologous to corresponding sequences in antibodies of another species or antibody class. Typically, the chimeric antibody or antibody fragment comprises a chimera of mouse and human antibody components.

Humanized forms of non-human antibodies are chimeric antibodies that contain minimal sequence derived from non-human immunoglobulin. A suitable humanized antibody or antibody fragment may comprise for example, immunoglobulin in which residues from a hypervariable region (e.g. derived from a CDR) of the recipient antibody or antigen- or ligand-binding fragment are replaced by residues from a hypervariable region of a non-human species (donor antibody) such as mouse, rat, rabbit or non-human primate having the desired specificity, affinity and/or capacity. In some instances, some framework region residues of the human immunoglobulin may be replaced by corresponding non-human residues.

As an alternative to humanization, human antibodies or antigen-binding fragments can be generated. For example, transgenic animals (e.g. mice) can be produced that are capable, upon immunization, of producing a full repertoire of human antibodies in the absence of endogenous immunoglobulin production. For example, homozygous deletion of the antibody heavy-chain joining region ($J_H$) gene in chimeric and germ-line mutant mice can result in complete inhibition of endogenous antibody production. Human germ-line immunoglobulin genes can be transferred to such germ-line mutant mice to result in the production of human antibodies upon antigen challenge. A human antibody or antigen-binding fragment can also be generated in vitro using the phage display technique.

Targets

An antibody or antigen- or ligand-binding fragment capable of binding any target antigen is suitable for use in the methods of the present invention. The antibody or antibody fragment may be capable of binding to an antigen or ligand associated with an autoimmune disorder (e.g. Type I diabetes, multiple sclerosis, rheumatoid arthritis, systemic lupus erythematosus, Crohn's disease and myasthenia gravis), an antigen or ligand associated with a cancer or an inflammatory state, an antigen associated with osteoporosis, an antigen associated with Alzheimer's disease, or a bacterial or viral antigen.

In particular, the target to which an antibody or antigen- or ligand-binding fragment may bind can be a CD antigen, growth factor, growth factor receptor, cell surface receptor such as an apoptosis receptor, a protein kinase or an oncoprotein. The antibody or antigen-binding fragment, for example a chimeric, humanized or human IgG1, IgG2 or IgG4 monoclonal antibody or antibody fragment, may thus be capable of binding to tumour necrosis factor α (TNF-α), interleukin-2 (IL-2), interleukin-6 (IL-6), glycoprotein IIb/IIIa, CD33, CD52, CD20, CD11a, CD3, RSV F protein, HER2/neu (erbB2) receptor, vascular endothelial growth factor (VEGF), epidermal growth factor receptor (EGFR), anti-TRAILR2 (anti-tumour necrosis factor-related apoptosis-inducing ligand receptor 2), complement system protein C5, α4 integrin or IgE.

More specifically, in the context of anti-cancer monoclonal antibodies, the antibody or antigen-binding fragment may be an antibody or antibody fragment capable of binding to epithelial cell adhesion molecule (EpCAM), mucin-1

(MUC1/Can-Ag), EGFR, CD20, carcinoembryonic antigen (CEA), HER2, CD22, CD33, Lewis Y and prostate-specific membrane antigen (PMSA). Again, the antibody is typically a chimeric, humanized or human IgG1, IgG2 or IgG4 monoclonal antibody.

Suitable monoclonal antibodies include, but are not limited to: infliximab (chimeric antibody, anti-TNFα), adalimumab (human antibody, anti-TNFα), basiliximab (chimeric antibody, anti-IL-2), abciximab (chimeric antibody, anti-GpIIb/IIIa), daclizumab (humanized antibody, anti-IL-2), gemtuzumab (humanized antibody, anti-CD33), alemtuzumab (humanized antibody, anti-CD52), edrecolomab (murine Ig2a, anti-EpCAM), rituximab (chimeric antibody, anti-CD20), palivizumab (humanized antibody, RSV target), trastuzumab (humanized antibody, anti-HER2/neu(erbB2) receptor), bevacizumab (humanized antibody, anti-VEGF), cetuximab (chimeric antibody, anti-EGFR), eculizumab (humanized antibody, anti-complement system protein C5), efalizumab (humanized antibody, anti-CD11a), ibritumomab (murine antibody, anti-CD20), muromonab-CD3 (murine antibody, anti-T cell CD3 receptor), natalizumab (humanized antibody, anti-α 4 integrin), nimotuzumab (humanized IgG1, anti-EGF receptor), omalizumab (humanized antibody, anti-IgE), panitumumab (human antibody, anti-EGFR), ranibizumab (humanized antibody, anti-VEGF), ranibizumab (humanized antibody, anti-VEGF) and I-131 tositumomab (humanized antibody, anti-CD20).

Preparation of Antibodies

Suitable monoclonal antibodies may be obtained for example, by the hybridoma method (e.g. as first described by Kohler et at Nature 256:495 (1975)), by recombinant DNA methods and/or following isolation from phage or other antibody libraries.

The hybridoma technique involves immunisation of a host animal (e.g. mouse, rat or monkey) with a desired immunogen to elicit lymphocytes that produce or are capable of producing antibodies that specifically bind to the immunogen. Alternatively, lymphocytes may be immunized in vitro. Lymphocytes are then fused with myeloma cells using a suitable fusing agent, such as polyethylene glycol, to form a hybridoma cell.

An antibody or antibody fragment can also be isolated from antibody phage libraries as an alternative to traditional monoclonal antibody hybridoma techniques for isolation of monoclonal antibodies. In particular, phage display may be used to identify antigen- or ligand-binding fragments for use in the methods of the invention. By using phage display for the high-throughput screening of antigen-antibody or ligand-antibody binding interactions, antibody fragments displayed on phage coat proteins can be isolated from a phage display library. By immobilising a target antigen or ligand on a solid support, a phage that displays an antibody capable of binding that antigen or ligand will remain on the support while others can be removed by washing. Those phages that remain bound can then be eluted and isolated, for example after repeated cycles of selection or panning Phage eluted in the final selection can be used to infect a suitable bacterial host from which phagemids can be collected and the relevant DNA sequence excised and sequenced to identify the relevant antigen- or ligand-binding fragment.

Polyclonal antiserum containing the desired antibodies is isolated from animals using techniques well known in the art. Animals such as sheep, rabbits or goats may be used for example, for the generation of antibodies against an antigen of interest by the injection of this antigen (immunogen) into the animal, sometimes after multiple injections. After collection of antiserum, antibodies may be purified using immunosorbent purification or other techniques known in the art.

The antibody or antigen- or ligand-binding fragment used in the method of the invention may be produced recombinantly from naturally occurring nucleotide sequences or synthetic sequences. Such sequences may for example be isolated by PCR from a suitable naturally occurring template (e.g. DNA or RNA isolated from a cell), nucleotide sequences isolated from a library (e.g. an expression library), nucleotide sequences prepared by introducing mutations into a naturally occurring nucleotide sequence (using any suitable technique known, e.g. mismatch PCR), nucleotide sequence prepared by PCR using overlapping primers, or nucleotide sequences that have been prepared using techniques for DNA synthesis. Techniques such as affinity maturation (for example, starting from synthetic, random or naturally occurring immunoglobulin sequences), CDR grafting, veneering, combining fragments derived from different immunoglobulin sequences, and other techniques for engineering immunoglobulin sequences may also be used.

Such nucleotide sequences of interest may be used in vitro or in vivo in the production of an antibody or antigen-binding fragment for use in the invention, in accordance with techniques well known to those skilled in the art.

For recombinant production of a monoclonal antibody or antibody fragment, the nucleic acid encoding it is isolated and inserted into a replicable vector for further cloning or for expression. The vector components generally including, but is not limited to one or more of the following: a signal sequence, an origin of replication, one or more marker genes, an enhancer element, a promoter, and a transcription termination sequence. Suitable host cells for cloning or expressing the DNA in the vectors are prokaryote, yeast, or higher eukaryote cells such as E. coli and mammalian cells such as CHO cells. Suitable host cells for the expression of glycosylated antibody are derived from multi-cellular organisms. Host cells are transformed with the expression or cloning vectors for antibody production and cultured in conventional nutrient media modified as appropriate for inducing promoters, selecting transformants, or amplifying the genes encoding the desired sequences.

When using recombinant techniques, the antibody can be produced intracellularly or directly secreted into the medium. If the antibody is produced intracellularly, as a first step, the particulate debris of either host cells or lysed cells, is removed, for example by centrifugation or ultra filtration. Where the antibody is secreted into the medium, supernatants from expression systems are generally first concentrated using a commercially available protein concentration filter. The antibody composition prepared from the cells can be purified using, for example, hydyoxylapatite chromatography, gel electrophoresis, dialysis and affinity chromatography.

The purified antibodies may then be isolated and optionally made into antigen- or ligand-binding fragments and/or derivatised.

Enzymes

Any protein enzyme is suitable for use in the invention. Such an enzyme comprises an active site and is capable of binding a substrate. The enzyme may be a monomer consisting of one polypeptide chain. Alternatively, the enzyme may be a dimer, tetramer or oligomer consisting of multiple polypeptide chains. The dimer, tetramer or oligomer may be a homo- or hetero- dimer, tetramer or oligomer respectively.

For example, the enzyme may need to form an aggregate (e.g. a dimer, tetramer or oligomer) before full biological activity or enzyme function is conferred. The enzyme may be an allosteric enzyme, an apoenzyme or a holoenzyme.

The enzyme may be conjugated to another moiety (e.g. a ligand, antibody, carbohydrate, effector molecule, or protein fusion partner) and/or bound to one or more cofactors (e.g. coenzyme or prosthetic group).

The moiety to which the enzyme is conjugated may include lectin, avidin, a metabolite, a hormone, a nucleotide sequence, a steroid, a glycoprotein, a glycolipid, or any derivative of these components.

Cofactors include inorganic compounds (e.g. metal irons such as iron, manganese, cobalt, copper, zinc, selenium, molybdenum) or organic compounds (e.g. flavin or heme). Suitable coenzymes include riboflavin, thiamine, folic acid which may carry hydride iron (H$^-$) carried by NAD or NADP$^+$, the acetyl group carried by coenzyme A, formyl, methenyl or methyl groups carried by folic acid and the methyl group carried by S-adenosyl methionine.

In another embodiment, the enzyme may be PEGylated especially if the enzyme is a therapeutic enzyme that is administered to a patient. Thus, one or more polyethylene glycol molecules may be covalently attached to the enzyme molecule. From one to three polyethylene glycol molecules may be covalently attached to each enzyme molecule. Such PEGylation is predominantly used to reduce the immunogenicity of an enzyme and/or increase the circulating half-life of the enzyme.

A suitable enzyme includes any enzyme classified under the International Union of Biochemistry and Molecular Biology Enzyme classification system of EC numbers including an oxidoreductase (EC 1), a transferase (EC 2), a hydrolase (EC 3), a lyase (EC 4), an isomerase (EC 5) or a ligase (EC 6). A typical enzyme is any enzyme that is used industrially.

An enzyme that is specific for any type of substrate is suitable for use in the present invention. Examples of a suitable enzyme includes a α-galactosidase, β-galactosidase, luciferase, serine proteinase, endopeptidase (e.g. cysteine endopeptidase), caspase, chymase, chymotrypsin, endopeptidase, granzyme, papain, pancreatic elastase, oryzin, plasmin, renin, subtilisin, thrombin, trypsin, tryptase, urokinase, amylase (e.g. α-amylase), xylanase, lipase, transglutaminase, cell-wall-degrading enzyme, glucanase (e.g. β-glucanase), glucoamylase, coagulating enzyme, milk protein hydrolysate, cell-wall degrading enzyme, blood coagulating enzyme, hementin, lysozyme, fibre-degrading enzyme, phytase, cellulase, hemicellulase, polymerase, protease, mannanase or glucoamylase.

An enzyme preserved according to the invention may thus be a therapeutic enzyme that is used to treat a disease or other medical condition, an enzyme used in industry for the production of bulk products such as glucose or fructose, in food processing and food analysis, in laundry and automatic dishwashing detergents, in the textile, pulp, paper and animal feed industries, as a catalyst in synthesis or fine chemicals, in diagnostic applications such as in clinical diagnosis, in biosensors or in genetic engineering.

Therapeutic enzymes to which the present invention can be applied include:
- a DNAase, for example a recombinant DNAase I such as Pulmozyme or Dornase that cleaves the DNA in the pulmonary mucus of children having cystic fibrosis;
- a gastric lipase such as Meripase which is a recombinant mammalian gastric lipase for the treatment of lipid malabsorption related to exocrine pancreatic lipase insufficiency;
- a mannose-terminated glucocerebrosidase such as Cerezyme which is a recombinant mannose-terminated glucocerebrosidase for the treatment of Gaucher disease, an inherited disorder that is caused by a deficiency in the enzyme glucocerebrosidase;
- α-galactosidase which is used in the treatment of the related glycogen storage disease Fabry disease;
- an adenosine deaminase (ADA) such as Pegademase that is used to treat ADA deficiency, a severe combined immunodeficiency;
- a phenylalanine ammonia lyase such as the PEGylated recombinant phenylalanine ammonia lyase Kuvan that is used for the treatment of phenylketonuria;
- tissue plasminogen activator, urokinase and streptokinase which are used in blood fibrinolysis to treat blood clots;
- a urate oxidase such as Elitek (rasburicase) which is a recombinant urate-oxidase that is produced by a genetically modified yeast and that is used in the treatment or prophylaxis of hyperuricemia in patients with leukaemia or lymphoma;
- L-asparaginase which is used in the treatment of childhood acute lymphoblastic leukaemia;
- Factor VIIa, used by patients with hemophilia;
- Factor IX which is used in the treatment of hemophilia B; and
- a superoxide dismutase such as the bovine superoxide dismutase Orgotein that is used for the treatment of familial amyotrophic lateral sclerosis.

Enzymes for use in food applications such as baking include amylases, xylanases, oxidoreductases, lipases, proteases and transglutaminase. Enzymes for use in fruit juice production and fruit processing include cell-wall-degrading enzymes. Enzymes for use in brewing include bacterial α-amylase, β-glucanase and glucoamylase in mashing, fungal α-amylase in fermentation and cysteine endopeptidase in post fermentation. Enzymes for use in dairy applications include coagulating enzymes, lipase, lysozyme, milk protein hydrolysates, transglutaninase, and β-galactosidase. Enzymes for use in detergent compositions include proteases, amylases, lipases, cellulases and mannanase. Enzymes for use in animal feed include HI fibre-degrading enzymes, phytases, proteases and amylases. Enzymes for use in pulp and paper processing include cellulases and hemicellulases.

The enzyme may alternatively be an enzyme used in research and development applications. For example, luciferases may be used for real-time imaging of gene expression in cell cultures, individual cells and whole organisms. Further, luciferases may be used as reporter proteins in molecular studies, for example to test the activity of transcription from specific promoters in cells transfected with luciferase. Enzymes may also be used in drug design for example in the testing of enzyme inhibitors in the laboratory. Further, enzymes may be used in biosensors (for example, a blood glucose biosensor using glucose oxidase).

The luciferase enzyme may be a firefly, beetle or railroad worm luciferase, or a derivative thereof. In particular, the luciferase may be derived from a North American firefly (*Phorinus pyralis*), *Luciola cruciata* (Japanese firefly), *Luciola lateralis* (Japanese firefly), *Luciola mingelica* (russian firefly), *Beneckea hanegi* (marine bacterial luciferase), *Pyrophorus plagiophthalamus* (click beetle), *Pyrocelia miyako* (firefly) *Ragophthalamus ohbai* (railroad worm),

*Pyrearinus termitilluminans* (click beetle), *Phrixothrix hirtus* (railroad worm), *Phrixothrix vivianii*, *Hotaria parvula* and *Photuris pensilvanica*, and mutated variants thereof.

Typically the α-galactosidase or β-galactosidase is derived from bacteria (such as *Escherichia coli*), a mammal (such as human, mouse, rat) or other eukaryote.

The enzyme maybe a naturally-occurring enzyme or a synthetic enzyme. Such enzymes may be derived from a host animal, plant or a microorganism.

Microbial strains used in the production of enzymes may be native strains or mutant strains that are derived from native strains by serial culture and selection, or mutagenesis and selection using recombinant DNA techniques. For example the microorganism may be a fungus e.g. *Thermomyces acermonium*, *Aspergillus*, *Penicillium*, *Mucor*, *Neurospora* and *Trichoderma*. Yeasts such as *Saccharomyces cereviseae* or *Pishia pastoris* may also be used in the production of enzymes for use in the methods of the present invention.

A synthetic enzyme may be derived using protein-engineering techniques well known in the art such as rational design, directed evolution and DNA shuffling.

Host organisms may be transformed with a nucleotide sequence encoding a desired enzyme and cultured under conditions conducive to the production of the enzyme and which facilitate recovery of the enzyme from the cells and/or culture medium.

Vaccine Immunogens

A vaccine immunogen suitable for use in the invention includes any immunogenic component of a vaccine. The vaccine immunogen comprises an antigen that can elicit an immune response in an individual when used as a vaccine against a particular disease or medical condition. The vaccine immunogen may be provided by itself prior to formulation of a vaccine preparation or it may be provided as part of a vaccine preparation. The vaccine immunogen may be a subunit vaccine, a conjugate useful as a vaccine or a toxoid. The vaccine immunogen may be a protein, bacterial-specific protein, mucoprotein, glycoprotein, peptide, lipoprotein, polysaccharide, peptidoglycan, nucleoprotein or fusion protein.

The vaccine immunogen may be derived from a microorganism (such as a bacterium, virus, fungi), a protozoan, a tumour, a malignant cell, a plant, an animal, a human, or an allergen. The vaccine immunogen is preferably not a viral particle. Thus, the vaccine immunogen is preferably not a whole virus or virion, virus-like particle (VLP) or virus nucleocapsid. The preservation of such viral particles is described in WO 2008/114021.

The vaccine immunogen may be synthetic, for example as derived using recombinant DNA techniques. The immunogen may be a disease-related antigen such as a pathogen-related antigen, tumour-related antigen, allergy-related antigen, neural defect-related antigen, cardiovascular disease antigen, rheumatoid arthritis-related antigen.

In particular, the pathogen from which the vaccine immunogen is derived may include human papilloma viruses (HPV), HIV, HSV2/HSV1, influenza virus (types A, B and C), para influenza virus, polio virus, RSV virus, rhinoviruses, rotaviruses, hepaptitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus, vaccinia virus, *Salmonella*, *Neisseria*, *Borrelia*, *Clamydia*, *Bordetella* such as *Bordetella pertussis*, *Plasmodium*, *Coxoplasma*, *Pneumococcus*, *Meningococcus*, *Cryptococcus*, *Streptococcus*, *Vibriocholerae*, *Yersinia* and in particular *Yersinia pestis*, *Staphylococcus*, *Haemophilus*, *Diptheria*, *Tetanus*, *Pertussis*, *Escherichia*, *Candida*, *Aspergillus*, *Entamoeba*, *Giardia* and *Trypanasoma*. The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and, bovine viral diarrhoea virus.

Tumor-associated antigens include for example, melanoma-associated antigens, mammary cancer-associated antigens, colorectal cancer-associated antigens or prostate cancer-associated antigens An allergen-related antigen includes any allergen antigen suitable for use in a vaccine to suppress an allergic reaction in an individual to which the vaccine is administered (e.g. antigens derived from pollen, dust mites, insects, food allergens, dust, poisons, parasites).

Subunit Vaccine Immunogens

A suitable subunit vaccine immunogen includes any immunogenic subunit of a protein, lipoprotein or glycoprotein derived from a microorganism (for example a virus or bacteria). Alternatively, the subunit vaccine immunogen may be derived from a disease-related antigen such as a tumour related protein. The subunit vaccine immunogen may be a naturally occurring molecule or a synthetic protein subunit. The vaccine immunogen may be a full-length viral or bacterial protein, glycoprotein or lipoprotein or a fragment of the full-length viral or bacterial protein, glycoprotein or lipoprotein.

A viral protein suitable as a subunit vaccine immunogen may be derived from a structural or non-structural viral protein. A suitable viral subunit immunogen is capable of stimulating a subject's immune system even in the absence of other parts of the virus. A suitable viral subunit vaccine immunogen includes a capsid protein, surface glycoprotein, envelope protein, hexon protein, fiber protein, coat protein or immunogenic fragment or derivative of such proteins or glycoproteins.

For example, the viral subunit vaccine immunogen may consist of a surface protein of the Influenza A, B or C virus. In particular, the vaccine immunogen may be a hemagglutinin (HA), neuraminidase (NA), nucleoprotein, M1, M2, NS1, NS2(NEP), PA, PB1, PB1-F2 and or PB2 protein, or an immunogenic derivative or fragment of any of these proteins. The immunogen may be HA1, HA2, HA3, HA4, HA5, HA6, HA7, HA8, HA9, HA10, HA11, HA12, HA13, HA14, HA15 and/or HA16, any immunogenic fragment or derivative thereof and any combination of the HA proteins, fragments or derivatives. The neuraminidase may be neuraminidase 1 (N1) or neuraminidase 2 (N2).

The viral subunit vaccine immunogen may be a hepatitis B virus viral envelope protein or a fragment or derivative thereof. For example, the subunit vaccine immunogen may be the hepatitis B surface antigen (HbsAg) or an immunogenic fragment or derivative thereof.

Typically, the bacterial subunit vaccine immunogen is a bacterial cell wall protein (e.g. flagellin, outer membrane protein, outer surface protein), a polysaccharide antigen (e.g. from *Neisseria meningitis*, *Streptococcus pneumonia*), toxin or an immunogenic fragment or derivative of such proteins, polysaccharides or toxins.

Derivatives of naturally occurring proteins include proteins with the addition, substitution and/or deletion of one or more amino acids. Such amino acid modifications can be generated using techniques known in the art, such as site-directed mutagenesis.

The subunit vaccine immunogen may be a fusion protein comprising a fusion protein partner linked with for example, a bacterial or viral protein or an immunogenic fragment or derivative thereof. A suitable fusion protein partner may prevent the assembly of viral fusion proteins into multimeric forms after expression of the fusion protein. For example, the fusion protein partner may prevent the formation of virus-like structures that might spontaneously form if the viral protein was recombinantly expressed in the absence of the fusion protein partner. A suitable fusion partner may also facilitate purification of the fusion protein, or enhance the recombinant expression of the fusion protein product. The fusion protein may be maltose binding protein, poly-histidine segment capable of binding metal ions, antigens to which antibodies bind, S-Tag, glutathione-S-transferase, thioredoxin, beta-galactosidase, epitope tags, green fluorescent protein, streptavidin or dihydrofolate reductase.

A subunit vaccine immunogen may be prepared using techniques known in the art for the preparation of for example, isolated peptides, proteins, lipoproteins, or glycoproteins. For example, a gene encoding a recombinant protein of interest can be identified and isolated from a pathogen and expressed in *E. coli* or some other suitable host for mass production of proteins. The protein of interest is then isolated and purified from the host cell (for example by purification using affinity chromatography).

In the case of viral subunit immunogens, the subunit may be purified from the viral particle after isolating the viral particle, or by recombinant DNA cloning and expression of the viral subunit protein in a suitable host cell. A suitable host cell for preparing viral particles must be capable of being infected with the virus and of producing the desired viral antigens. Such host cells may include microorganisms, cultured animal cells, transgenic plants or insect larvae. Some proteins of interest may be secreted as a soluble protein from the host cell. In the case of viral envelope or surface proteins, such proteins may need to be solubilized with a detergent to extract them from the viral envelope, followed by phase separation in order to remove the detergent.

A subunit vaccine immunogen may be combined in the same preparation and preserved together with one, two three or more other subunit vaccine immunogens.

Toxoids

The invention can be applied to toxoids. A toxoid is a toxin, for example derived from a pathogen, animal or plant, that is immunogenic but has been inactivated (for example by genetic mutation, chemical treatment or by conjugation to another moiety) to eliminate toxicity to the target subject. The toxin may be for example, a protein, lipoprotein, polysaccharide, lipopolysaccharide or glycoprotein. The toxoid may thus be an endotoxin or an exotoxin that has been toxoided.

The toxoid may be a toxoid derived from a bacterial toxin such as tetanus toxin, *diphtheria* toxin, pertussis toxin, botulinum toxin, *C. difficile* toxin, Cholera toxin, shiga toxin, anthrax toxin, bacterial cytolysins or pneumolysin and fragments or derivatives thereof. The toxoid may therefore be tetanus toxoid, *diphtheria* toxoid or pertussis toxoid. Other toxins from which a toxoid can be derived include poisons isolated from animals or plants, for example from *Crotalis atrox*. Typically, the toxoid is derived from botulinum toxin or anthrax toxin. For example, the botulinum toxin may be derived from *Clostridium botulinum* of serotype A, B, C, D, E, F or G. The vaccine immunogen derived from a botulinum toxin may be combined in the same preparation and preserved together with one or more other vaccine immunogens derived from a botulinum toxin (e.g. a combination of immunogens derived from botulinum serotypes A, B, C, D, E, F or G, such as for example A, B and E).

The anthrax toxin may be derived from a strain of *Bacillus anthracis*. The toxoid may consist of one of more components of the anthrax toxin, or derivatives of such components, such as protective antigen (PA), the edema factor (EF) and the lethal factor (LF). Typically the toxoid derived from the anthrax toxin consists of protective antigen (PA).

The toxoid may be conjugated to another moiety, for example as a fusion protein, for use as a toxoid vaccine. A suitable moiety in a conjugate toxoid includes a substance that aids purification of the toxoid (e.g. histidine tag) or reduces toxicity to a target subject. Alternatively, the toxoid may act as an adjuvant by increasing the immunogenicity of an antigen to which it is attached. For example, the B polysaccharide of *Haemophilus influenzae* may be combined with *diptheria* toxoid.

A vaccine immunogen may be combined in the same preparation and preserved together with one, two three or more vaccine immunogens. For example, a *diphtheria* toxoid may be preserved with tetanus toxoid and pertussis vaccine (DPT). *Diptheria* toxoid may be preserved with just tetanus toxoid (DT), or *diphtheria* toxoid may be preserved with *diphtheria* toxoid, tetanus toxoid and acellular Pertussis (DTaP).

Techniques for the preparation of toxoids are well known to those skilled in the art. Toxin genes may be cloned and expressed in a suitable host cell. The toxin product is then purified and may be converted to toxoid chemically, for example using formalin or glutaraldehyde. Alternatively, a toxin gene may be engineered so that it encodes a toxin having reduced or no toxicity e.g. by addition, deletion and/or substitution of one or more amino acids. The modified toxin can then be expressed in a suitable host cell and isolated. The toxicity of toxin genes may also be inactivated by conjugation of toxin genes or fragments thereof to a further moiety (e.g. polysaccharide or polypeptide).

Conjugate Vaccine Immunogens

A conjugate vaccine immunogen may be a conjugate of an antigen (for example a polysaccharide or other hapten) to a carrier moiety (for example a peptide, polypeptide, lipoprotein, glycoprotein, mucoprotein or any immunostimulatory derivative or fragment thereof) that stimulates the immunogenicity of the antigen to which it is attached. For example, the conjugate vaccine immunogen may be a recombinant protein, recombinant lipoprotein or recombinant glycoprotein conjugated to an immunogen of interest (for example a polysaccharide).

The conjugate vaccine immunogen may be used in a vaccine against *Streptococcus pneumonia*, *Haemophilus influenza*, meningococcus (strains A, B, C, X, Y and W135) or pneumococcal strains. For example, the vaccine may be for example, the heptavalent Pneumococcal $CRM_{197}$ Conjugate Vaccine (PCV7), an MCV-4 or *Haemophilus influenzae* type b (Hib) vaccine.

A conjugate vaccine immunogen may be combined in the same preparation and preserved together with one, two three or more other conjugate vaccine immunogens.

Methods for the preparation of conjugate polysaccharide-protein conjugates are well known in the art. For example, conjugation may occur via a linker (e.g. B-propionamido, nitrophenyl-ethylamine, haloalkyl halides, glycosidic linkages).

Compounds of Formula (I) or Physiologically Acceptable Salts or Esters Thereof and Compounds of Formula (II) or Physiologically Acceptable Salts or Esters Thereof The compounds of formula (I) and (II) may be present as a physiologically acceptable salt or ester thereof.

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

As used herein, a $C_{1-6}$ alkyl group is preferably a $C_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) and formula (II) also include compounds in which the carboxylate anion is protonated to give —COOH and the ammonium or sulfonium cation is associated with a pharmaceutically acceptable anion. Further, for the avoidance of doubt, the compounds defined above may be used in any tautomeric or enantiomeric form.

Compounds of Formula (I)

Typically, $R_1$ represents hydrogen or $C_{1-6}$ alkyl and $R_4$ represents hydrogen.

Typically, $R_1$ represents hydrogen or $C_{1-4}$ alkyl, preferably hydrogen, methyl, ethyl, propyl, isopropyl, butyl, isobutyl or tert-butyl, more preferably hydrogen, methyl or ethyl.

Typically, $R_2$ represents hydrogen or $C_{1-6}$ alkyl, preferably hydrogen or $C_{1-4}$, more preferably alkyl hydrogen, methyl, ethyl, propyl, isopropyl, butyl, isobutyl or tert-butyl, more preferably hydrogen, methyl or ethyl.

Typically $R_3$ represents $C_{1-4}$ alkyl, preferably, methyl, ethyl, propyl, isopropyl, butyl, isobutyl or tert-butyl, more preferably methyl or ethyl.

Preferably, $R_1$ represents hydrogen or $C_{1-4}$ alkyl, $R_2$ represents hydrogen or $C_{1-4}$ alkyl, $R_3$ represents $C_{1-4}$ alkyl and $R_4$ represents hydrogen.

Preferably, therefore, the compound of formula (I) is a glycine derivative of formula (IA) or a physiologically acceptable salt or ester thereof:

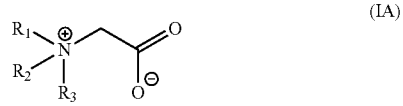

(IA)

In a preferred embodiment $R_1$ represents H, $R_2$ represents H and $R_3$ represents $C_{1-6}$ alkyl. In other words, in this embodiment the compound of formula (I) is a N—$C_{1-6}$ alkyl-glycine or physiologically acceptable salt or ester thereof. The alkyl group is typically a $C_{1-4}$ alkyl group. Preferred alkyl groups are selected from methyl, ethyl, propyl, isopropyl, butyl, isobutyl and tert-butyl. Methyl and ethyl are more preferred. N-methylglycine, also called sarcosine, is particularly preferred.

In another preferred embodiment $R_1$ represents H, $R_2$ represents $C_{1-6}$ alkyl and $R_3$ represents $C_{1-6}$ alkyl. In other words, in this embodiment the compound of formula (I) is a N,N-di($C_{1-6}$ alkyl)-glycine or physiologically acceptable salt or ester thereof. Each alkyl group is typically a $C_{1-4}$ alkyl group. Preferred alkyl groups are selected from methyl, ethyl, propyl, isopropyl, butyl, isobutyl and tert-butyl. Methyl and ethyl are more preferred. N,N-Dimethylglycine, which is also termed dimethylglycine (DMG) and or 2-(dimethylamino)-acetic acid, is particularly preferred.

In another preferred embodiment, $R_1$ represents $C_{1-6}$ alkyl, $R_2$ represents $C_{1-6}$ alkyl and $R_3$ represents $C_{1-6}$ alkyl. In other words, in this embodiment the compound of formula (I) is a N,N-di($C_{1-6}$ alkyl)-glycine or physiologically acceptable salt or ester thereof. Each alkyl group is typically a $C_{1-4}$ alkyl group. Preferred alkyl groups are selected from methyl, ethyl, propyl, isopropyl, butyl, isobutyl and tert-butyl. Methyl and ethyl are more preferred. N,N,N-trimethylglycine, which is also termed trimethylglycine (TMG), is particularly preferred.

Alternatively, the compound of formula (I) is preferably a proline derivative of formula (IB) or a physiologically acceptable salt or ester thereof:

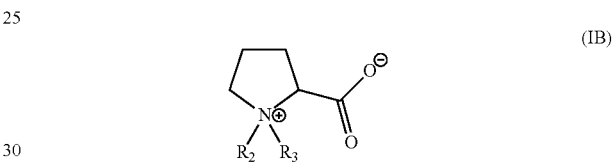

(IB)

Preferably the compound of formula (IB) is an S-proline derivative. Preferably $R_2$ and $R_3$ both represent methyl; this compound is known as proline betaine. S-proline betaine or physiologically acceptable salt or ester thereof is particularly preferred:

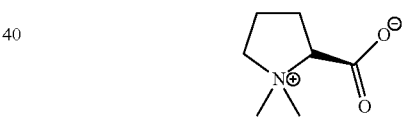

Compounds of formula (IA) or physiologically acceptable salts or esters thereof are particularly preferred.

A further alternative preferred compound of formula (I) is cocamidopropyl betaine (CAPB).

Compounds of Formula (II)

Typically $R_a$ and $R_b$ independently represent $C_{1-4}$ alkyl, preferably methyl, ethyl, propyl, isopropyl, butyl, isobutyl or tert-butyl, more preferably methyl or ethyl.

Typically, the carboxylate and amine substituents of $R_c$ are attached to the same carbon atom of the $R_c$ alkyl moiety. Typically $R_c$ is a $C_{2-4}$ or $C_{2-3}$ alkyl moiety.

Typically X represents —S(O)$_2$—. That is to say, the compound of formula (II) is preferably a sulfone compound of formula (IIA) or a physiologically acceptable salt or ester thereof:

(IIA)

A preferred sulfone compound is methylsulfonylmethane (MSM), which is also known as dimethylsulfone (DMSO$_2$).

Alternatively, X typically represents —S$^+$(Rc)-. That is to say, the compound of formula (II) is alternatively preferably a compound of formula (IIB) or a physiologically acceptable salt or ester thereof:

(IIB)

A preferred compound of formula (IIB) is S-methyl-L-methionine (SMM) or a physiologically acceptable salt or ester thereof.

Sugars

Sugars suitable for use in the present invention include reducing sugars such as glucose, fructose, glyceraldehydes, lactose, arabinose and maltose; and preferably non-reducing sugars such as sucrose and raffinose, more preferably sucrose. The sugar may be a monosaccharide, disaccharide, trisaccharide, or other oligosaccharides. The term "sugar" includes sugar alcohols. In one embodiment, therefore, use of a non-reducing sugar or a sugar alcohol is preferred.

Monosaccharides such as galactose and mannose; dissaccharides such as sucrose, lactose and maltose; trisaccharides such as raffinose; and tetrasaccharides such as stachyose are envisaged. Trehalose, umbelliferose, verbascose, isomaltose, cellobiose, maltulose, turanose, melezitose and melibiose are also suitable for use in the present invention. A suitable sugar alcohol is mannitol. When mannitol is used, cakes of improved appearance may be obtained on freeze-drying.

The presence of sugar may act to improve stability. The addition of sugar may also provide other benefits such as an altered lyophilisation cake and improved solubility for faster reconstitution. Generally one or more sugars is present when freeze-drying is used. When one sugar is used, the sugar is preferably sucrose or mannitol, more preferably mannitol.

Preservation of viral activity is particularly effective when two or more sugars are used in the preservation mixture. Two, three or four sugars may be used. Preferably, the aqueous solution is a solution of sucrose and raffinose. Thus, when two or more sugars are used the sugars preferably comprise sucrose, more preferably sucrose and raffinose. Sucrose is a disaccharide of glucose and fructose. Raffinose is a trisaccharide composed of galactose, fructose and glucose.

Preservation Procedure

In the present invention, an aqueous solution comprising the polypeptide, one or more sugars and a compound of formula (I) or a physiologically acceptable salt or ester thereof and/or a compound of formula (II) or a physiologically acceptable salt or ester thereof is dried. Any suitable aqueous solution may be used. The solution may be buffered. The solution may be a HEPES, phosphate-buffered, Tris-buffered or pure water solution. The solution may optionally comprise one or more co-solvents. An example of a co-solvent is t-butyl alcohol.

The solution may have a pH of from 2 to about 12 and may be buffered. The solution may be buffered with HEPES buffer, phosphate-buffer, Tris-buffer, sodium citrate buffer, bicine buffer (i.e. N,N-bis(2-hydroxyethyl) glycine buffer) or MOPS buffer (i.e. 3-(N-morpholino) propanesulfonic acid buffer). The solution may or may not contain NaCl. The solution may thus be a saline sodium citrate (SSC) buffered solution.

It is preferable that the aqueous solution to be dried does not comprise (a) an aluminium salt adjuvant, and/or (b) a nonionic surfactant such as polysorbate (e.g. polysorbate 80), and/or (c) ethylene-diamine, cadaverine, putrescine, spermidine or spermine.

Generally a preparation of the polypeptide is admixed with the preservation mixture, i.e. with an aqueous solution of a compound of formula (I) or a physiologically acceptable salt or ester thereof and/or a compound of formula (II) or a physiologically acceptable salt or ester thereof and one, two or more sugars. The preservation mixture may itself be buffered. It may be a HEPES, phosphate-buffered, Tris-buffered or pure water solution.

Thus, typically in the present invention, a buffered aqueous solution comprising (i) the polypeptide and (ii) one or more sugars and a compound of formula (I) or a physiologically acceptable salt or ester thereof and/or a compound of formula (II) or a physiologically acceptable salt or ester thereof as the sole excipients, is dried.

Typically in the present invention, a buffered aqueous solution comprising (i) the polypeptide and (ii) one or more sugars and a compound of formula (I) or a physiologically acceptable salt or ester thereof and/or a compound of formula (II) or a physiologically acceptable salt or ester thereof as the sole solutes, is dried.

Alternatively, the aqueous solution may typically consist, or consist essentially, of polypeptide, a compound of formula (I) or a physiologically acceptable salt or ester thereof and/or a compound of formula (II) or a physiologically acceptable salt or ester thereof, and one or more sugars.

The concentration of sugar, or the total sugar concentration if more than one sugar is present, in the aqueous solution for drying is at least 0.01M, typically up to saturation. Generally the sugar concentration, or the total sugar concentration if more than one sugar is present, is at least 0.05M, at least 0.1M, at least 0.2M or at least 0.5M up to saturation e.g. saturation at room temperature or up to 3M, 2.5M, 2M, 1.5M or 1M. The sugar concentration, or the total sugar concentration if more than one sugar is present, may therefore range from, for example, 0.1M to 3M or 0.2M to 2M or 0.3M to 1M.

When more than one sugar is present, preferably one of those sugars is sucrose. The sucrose may be present at a concentration of from 0.05M, 0.1M, 0.25M or 0.5M up to saturation e.g. saturation at room temperature or up to 3M, 2.5M or 2M. A concentration of 0.1M to 1M sucrose is particularly preferred, for example 0.1 to 0.3M or 0.3 to 0.7M or 0.7M or 1M.

The ratio of the molar concentration of sucrose relative to the molar concentration of the other sugar(s) is typically from 1:1 to 20:1 such as from 5:1 to 15:1. In the case when two sugars are present and in particular when sucrose and raffinose are present, therefore, the ratio of molar concentrations of sucrose is typically from 1:1 to 20:1 such as from 5:1 to 15:1 and preferably about 10:1.

When one sugar is present, preferably the sugar is mannitol. The mannitol may be present at a concentration of from 0.05M, 0.1M, 0.25M or 0.5M up to saturation e.g. saturation at room temperature or up to 3M, 2.5M, 2M, 1.5M or 1M. Preferably the concentration of mannitol is from 0.1M to 1M, more preferably from 0.3M to 0.7M, for example 0.4M to 0.6M.

Typically the concentration of the compound of formula (I) or physiologically acceptable salt or ester thereof, when present, is from 0.001M to 2.5M, preferably from 0.01M to 2M, more preferably from 0.01 to 1.5M. For example, the concentration range may be from 0.1M to 1M, preferably from 0.3M to 0.7M.

Typically the concentration of the compound of formula (II) or physiologically acceptable salt or ester thereof, when present, is from 0.001M to 2.5M, preferably from 0.01M to 2M, more preferably from 0.01 to 1.5M. For example, the concentration range may be from 0.1M to 1M, preferably from 0.3M to 0.7M.

When a compound of formula (I) or physiologically acceptable salt or ester thereof and a compound of formula (II) or physiologically acceptable salt or ester thereof are present, the compounds can be present in amounts that result in synergy. Typically, (a) the concentration of the compound of formula (I) or physiologically acceptable salt or ester thereof is from 0.001M to 2.5M, preferably from 0.01M to 2M, more preferably from 0.01 to 1.5M, and (b) the concentration of the compound of formula (II) or physiologically acceptable salt or ester thereof is from 0.001M to 2.5M, preferably from 0.01M to 2M, more preferably from 0.01 to 1.5M. For example, the concentration of the compound of formula (I) or physiologically acceptable salt or ester thereof may be from 0.1M to 1M, preferably from 0.3 to 0.7M, and the concentration of the compound of formula (II) or physiologically acceptable salt or ester thereof may be from 0.1M to 1M, preferably from 0.3 to 0.7M.

When a compound of a compound of formula (I) or physiologically acceptable salt or ester thereof is present in the solution, optionally one or more, preferably one, further compounds of formula (I) or physiologically acceptable salts or esters thereof may be present. The concentration of each compound of formula (I) or physiologically acceptable salt or ester thereof is preferably as set out above. Typically, when two such compounds, the compounds are DMG or a physiologically acceptable salt or ester thereof and TMG or a physiologically acceptable salt or ester thereof.

When a compound of a compound of formula (II) or physiologically acceptable salt or ester thereof is present in the solution, optionally one or more, preferably one, further compounds of formula (II) or physiologically acceptable salts or esters thereof may be present. The concentration of each compound of formula (II) or physiologically acceptable salt or ester thereof is preferably as set out above.

Preferably, when one sugar is present which is mannitol, a compound of formula (I) or physiologically acceptable salt or ester thereof is used, for example DMG.

Preferably, when two sugars are present which are sucrose and raffinose, a compound of formula (I) or physiologically acceptable salt or ester thereof (such as DMG) and a compound of formula (II) or physiologically acceptable salt or ester thereof (such as MSM) are used.

Particularly preferred aqueous solutions for use in the invention comprise, in addition to the polypeptide, the following components:
- 0.3 to 0.7M of a sugar alcohol, preferably mannitol, for example 0.4 to 0.6M or about 0.5M; and 0.1M to 1.5M of a compound of formula (I) or physiologically acceptable salt, preferably DMG or TMG, for example 0.3M to 1M or about 0.7M or about 0.8M;
- 0.01 to 0.5M sucrose, for example 0.05 to 0.15M or about 0.1M; 0.001 to 0.05M raffinose, for example 0.005 to 0.015M or about 0.01M; 0.05M to 1.5M of a compound of formula (I) or physiologically acceptable salt, preferably DMG, for example 0.1M to 1.2M, or about 1M; and 0.05M to 1.5M of a compound of formula (II) or physiologically acceptable salt, preferably MSM, for example 0.1M to 1.2M, or about 0.1M, about 0.3 M, about 0.7M or about 1M;
- 0.1 to 1.0 M sucrose, for example about 0.15M or about 0.45M; 0.1 to 0.5M raffinose, for example about 0.2M or about 0.25M; and 0.05M to 1.5M of a compound of formula (I) or physiologically acceptable salt, preferably DMG, for example 0.1M to 1.3M, or about 0.6M or about 1.3M;
- 1.0 to 1.8M sucrose, for example 1.1 to 1.6M or about 1.1M or 1.2M or 1.4M; 0.01 to 0.5M raffinose, for example 0.05 to 0.3M or about 0.15M; and 0.1 to 0.5M of a compound of formula (I) or physiologically acceptable salt, preferably TMG, for example 0.2 to 0.4M or about 0.1M; or
- 0.3 to 0.7M of a sugar alcohol, preferably mannitol, for example 0.4 to 0.6M or about 0.5M; 0.1M to 1.5M of a compound of formula (I) or physiologically acceptable salt, preferably DMG, for example 0.3M to 1M or about 0.6M; and 0.1M to 1.5M of a second compound of formula (I) or physiologically acceptable salt, preferably TMG, for example 0.3M to 1M or about 0.5M.

The particular concentration of compound of formula (I) or physiologically acceptable salt and/or ester thereof or compound of formula (II) or physiologically acceptable salt or ester thereof that is employed will depend on several factors including the type of polypeptide particle to be preserved; the particular compound being used; whether one, two more sugars are present and the identity of the sugar(s); and the drying procedure and conditions. Similarly, the selection and concentration of sugars will also depend on the polypeptide particle to be preserved; the excipients selected; and the drying procedure and conditions. The specific compounds of formula (I) or physiologically acceptable salt and/or ester thereof or compound of formula (II) or physiologically acceptable salt or ester thereof, the concentration of these compounds and the sugar(s) and their concentration can thus be selected by routine experimentation, in order to achieve the best stability.

Typically, drying is achieved by freeze drying, vacuum drying, fluid bed drying or spray-drying. Freeze-drying is preferred. By reducing the water in the material and sealing the material in a vial, the material can be easily stored, shipped and later reconstituted to its original form. The drying conditions can be suitably optimized via routine experimentation.

On drying, a composition is formed which incorporates the polypeptide. A matrix incorporating the polypeptide is produced. The composition is typically an amorphous solid. A solid matrix, generally an amorphous solid matrix, is thus generally formed. By "amorphous" is meant non-structured and having no observable regular or repeated organization of molecules (i.e. non-crystalline).

The sugar or sugars provide the amorphous matrix in the dried composition. The compound of formula (I) or a physiologically acceptable salt or ester thereof and/or a compound of formula (II) or physiologically acceptable salt or ester thereof is dispersed in the sugar matrix. The compound of formula (I) or a physiologically acceptable salt or ester thereof and/or compound of formula (II) or physiologically acceptable salt or ester thereof is thus incorporated within the sugar matrix. The polypeptide is incorporated within the sugar matrix too. The drying procedure can thus be effected e.g. by freeze-drying to form an amorphous cake within which the polypeptide is incorporated.

When aqueous solutions comprising sugars are dried, the sugar may crystallise during the drying step, rather than adopt an amorphous structure. For example, mannitol can form three anhydrous crystalline forms (alpha-, beta-, and delta-mannitol), a hemihydrate as well as an amorphous mannitol form. Mannitol often forms an unstable meta-glass during freeze drying, which reverts to a crystalline form. Thus, for example, when an aqueous solution of mannitol is dried in the absence of the excipients of the invention, the mannitol generally adopts a crystalline or a meta-stable glass rather than a stable amorphous structure. The use of an annealing step can encourage formation of crystalline mannitol. The presence of compound of formula (I) or a physiologically acceptable salt or ester thereof and/or a compound of formula (II) or physiologically acceptable salt or ester in the solution for drying may prevent formation of a crystalline sugar structure, such that the sugar adopts an amorphous structure. For example, DMG typically prevents mannitol from crystallising when a solution of the invention comprising mannitol and DMG is dried.

The drying step is generally performed as soon as the aqueous solution has been prepared or shortly afterwards. Alternatively, the aqueous solution is typically stored prior to the drying step. The polypeptide in the aqueous solution is preserved by the compound of formula (I) or a physiologically acceptable salt or ester thereof and/or a compound of formula (II) or physiologically acceptable salt or ester thereof and, optionally, one or more sugars during storage.

The aqueous solution, or bulk intermediate solution, is generally stored for up to 5 years, for example up to 4 years, 3 years, 2 years or 1 year. Preferably the solution is stored for up to 6 months, more preferably up to 3 months or up to 2 months, for example 1 day to 1 month or 1 day to 1 week. Prior to drying, the solution is typically stored in a refrigerator or in a freezer. The temperature of a refrigerator is typically 2 to 8° C., preferably 4 to 6° C., or for example about 4° C. The temperature of a freezer is typically −10 to −80° C., preferably −10 to −30° C., for example about −20° C.

The solution is typically stored in a sealed container, preferably a sealed inert plastic container, such as a bag or a bottle. The container is typically sterile. The volume of the bulk intermediate solution is typically 0.1 to 100 litres, preferably 0.5 to 100 litres, for example 0.5 to 50 litres, 1 to 20 litres or 5 to 10 litres. The container typically has a volume of 0.1 to 100 litres, preferably 0.5 to 100 litres, for example 0.5 to 50 litres, 1 to 20 litres or 5 to 10 litres.

If the stored bulk intermediate solution is to be freeze-dried, it is typically poured into a freeze-drying tray prior to the drying step.

Stable storage of the solution increases the flexibility of the manufacturing process. Thus, the solution can be easily stored, shipped and later dried.

Freeze-drying

Freeze-drying is a dehydration process typically used to preserve perishable material or make the material more convenient for transport. Freeze-drying represents a key step for manufacturing solid protein and vaccine pharmaceuticals. However, biological materials are subject to both freezing and drying stresses during the procedure, which are capable of unfolding or denaturing proteins. Furthermore, the rate of water vapour diffusion from the frozen biological material is very low and therefore the process is time-consuming. The preservation technique of the present invention enables biological materials to be protected against the desiccation and/or thermal stresses of the freeze-drying procedure.

There are three main stages to this technique namely freezing, primary drying and secondary drying. Freezing is typically performed using a freeze-drying machine. In this step, it is important to cool the biological material below its eutectic point, (Teu) in the case of simple crystalline products or glass transition temperature (Tg') in the case of amorphous products, i.e. below the lowest temperature at which the solid and liquid phase of the material can coexist. This ensures that sublimation rather than melting will occur in the following primary drying stage.

During primary drying the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

Vacuum Drying

In certain embodiments, drying is carried out using vacuum desiccation at around 1300 Pa. However vacuum desiccation is not essential to the invention and in other embodiments, the preservation mixture contacted with the polypeptide is spun (i.e. rotary desiccation) or freeze-dried (as further described below). Advantageously, the method of the invention further comprises subjecting the preservation mixture containing the polypeptide to a vacuum. Conveniently, the vacuum is applied at a pressure of 20,000 Pa or less, preferably 10,000 Pa or less. Advantageously, the vacuum is applied for a period of at least 10 hours, preferably 16 hours or more. As known to those skilled in the art, the period of vacuum application will depend on the size of the sample, the machinery used and other parameters.

Spray-drying and Spray Freeze-drying

In another embodiment, drying is achieved by spray-drying or spray freeze-drying the polypeptide admixed with the preservation mixture of the invention. These techniques are well known to those skilled in the art and involve a method of drying a liquid feed through a gas e.g. air, oxygen-free gas or nitrogen or, in the case of spray freeze-drying, liquid nitrogen. The liquid feed is atomized into a spray of droplets. The droplets are then dried by contact with the gas in a drying chamber or with the liquid nitrogen.

Fluid Bed Drying

In a further embodiment, drying is achieved by fluid bed drying the polypeptide admixed with the preservation mixture of the invention. This technique is well known to those skilled in the art and typically involves passing a gas (e.g. air) through a product layer under controlled velocity conditions to create a fluidized state. The technique can involve the stages of drying, cooling, agglomeration, granulation and coating of particulate product materials. Heat may be supplied by the fluidization gas and/or by other heating surfaces (e.g. panels or tubes) immersed in the fluidized layer. Cooling can be achieved using a cold gas and/or cooling surfaces immersed in the fluidized layer. The steps of agglomeration and granulation are well known to those skilled in the art and can be performed in various ways depending on the product properties to be achieved. Coating of particulate products such as powders, granules or tablets can be achieved by spraying a liquid on the fluidized particles under controlled conditions.

Dried Composition

A composition having a low residual moisture content can be obtained. A level of residual moisture content is achieved which offers long term preservation at greater than refrigeration temperatures e.g. within the range from 4° C. to 56° C. or more, or lower than refrigeration temperatures e.g. within the range from 0 to −70° C. or below. The dried composition may thus have residual moisture content of 10% or less, 5% or less, 2% or less or 1% or less by weight. Preferably the residual moisture content is 0.5% or more 1% or more. Typically a dried composition has residual moisture content of from 0.5 to 10% by weight and preferably from 1 to 5% by weight.

The composition can be obtained in a dry powder form. A cake resulting from e.g. freeze-drying can be milled into powder form. A solid composition according to the invention thus may take the form of free-flowing particles. The solid composition is typically provided as a powder in a sealed vial, ampoule or syringe. If for inhalation, the powder can be provided in a dry powder inhaler. The solid matrix can alternatively be provided as a patch. A powder may be compressed into tablet form.

The composition may typically consist, or consist essentially, of polypeptide, a compound of formula (I) or a physiologically acceptable salt or ester thereof and/or a compound of formula (II) or a physiologically acceptable salt or ester thereof, and optionally one or more sugars.

Drying onto a Solid Support

However, in a further embodiment of the method of the invention, the admixture comprising a polypeptide is dried onto a solid support. The solid support may comprise a bead, test tube, matrix, plastic support, microtitre dish, microchip (for example, silicon, silicon-glass or gold chip), or membrane. In another embodiment, there is provided a solid support onto which a polypeptide particle preserved according to the methods of the present invention is dried or attached.

Excipient

In the present invention, an excipient for the preservation of a polypeptide is also provided. The excipient comprises (a) optionally one or more sugars such as sucrose, raffinose, stachyose, trehalose, or a sugar alcohol or any combination thereof and (b) a compound of formula (I) or a physiologically acceptable salt or ester thereof and/or a compound of formula (II) or a physiologically acceptable salt or ester thereof. Preferably one or more sugars is present. Preferably the excipient consists, or consists essentially of these components.

By "excipient" is meant an inactive substance used as a carrier for the polypeptide of the invention. Typically, the polypeptide are dissolved into or mixed with the excipient, which acts as a preservative of the polypeptide and/or in some contexts aids administration and absorption into the body. As well as the preservation mixture of the present invention, an excipient may also comprise other preservatives such as antioxidants, lubricants and binders well known in the art, as long as those ingredients do not significantly reduce the effectiveness of the preservation mixture of the present invention.

A composition having a low residual moisture content can be obtained. A level of residual moisture content is achieved which offers long term preservation at greater than refrigeration temperatures e.g. within the range from 4° C. to 56° C. or more, or lower than refrigeration temperatures e.g. within the range from 0 to −70° C. or below. The dried composition may thus have residual moisture content of 10% or less, 5% or less, 2% or less or 1% or less by weight. Preferably the residual moisture content is 0.5% or more 1% or more. Typically a dried composition has residual moisture content of from 0.5 to 10% by weight and preferably from 1 to 5% by weight.

The composition can be obtained in a dry powder form. A cake resulting from e.g. freeze-drying can be milled into powder form. A solid composition according to the invention thus may take the form of free-flowing particles. The solid composition is typically provided as a powder in a sealed vial, ampoule or syringe. If for inhalation, the powder can be provided in a dry powder inhaler. The solid matrix can alternatively be provided as a patch. A powder may be compressed into tablet form.

The composition may typically consist, or consist essentially, of polypeptide, a compound of formula (I) or a physiologically acceptable salt or ester thereof and/or a compound of formula (II) or a physiologically acceptable salt or ester thereof, and optionally one or more sugars.

Composition

The composition of the invention is typically solid. The composition is typically dried, preferably freeze-dried.

In this way, a composition having a low residual moisture content can be obtained. A level of residual moisture content is achieved which offers long term preservation at greater than refrigeration temperatures e.g. within the range from 4° C. to 56° C. or more, or lower than refrigeration temperatures e.g. within the range from 0 to −70° C. or below. The dried solid composition thus typically has a residual moisture content of 10% or less, 5% or less, 2% or less or 1% or less by weight. Preferably, the residual moisture content is 0.5% or more 1% or more.

Typically the composition is obtained in a dry powder form. Preferably the composition is in the form of a cake, resulting from for example freeze-drying. The dry powder form and/or cake is typically milled into powder form. A composition according to the invention thus preferably takes the form of free-flowing particles. Typically, the composition is substantially amorphous, or amorphous.

Typically, when the composition is analysed by differential scanning calorimetry (DSC), no crystalline melt endotherms are observed. Thus, when the composition is analysed by DSC, the composition preferably does not have any crystalline melt endotherms, typically melt endotherms having a melting endothermic enthalpy of 1 J/g or more, in the temperature range of 50 to 250° C., preferably 100 to 200° C. The DSC analysis is carried out as described in Example 8 below. The specific temperature at which crystalline melt endotherms are absent will depend on the components present in the composition. For example, when the composition comprises mannitol, there is preferably no crystalline melt endotherm in the range 150 to 180° C., since typically a mannitol endothermic melt should be observed at 166° C.

Typically, when the composition is analysed by differential scanning calorimetry (DSC), no re-crystallisation exotherms are observed. Thus, when the composition is analysed by DSC, the composition preferably does not have any re-crystallisation exotherms, typically re-crystallisation exotherms having a melting endothermic enthalpy of 1 J/g or more, in the temperature range of 50 to 150° C. The DSC analysis is carried out as described in Example 8 below. The specific temperature at which re-crystallisation exotherms are absent will depend on the components present in the composition. For example, when the composition comprises mannitol, there are preferably no re-crystallisation exotherms in the range 50 to 120° C.

The composition of the invention is preferably a solid, freeze-dried cake, which more preferably takes the form of free-flowing particles.

For example, the composition of the invention may be:

- a solid composition comprising a compound of formula (I) or a physiologically acceptable salt or ester thereof and/or a compound of formula (II) or a physiologically acceptable salt or ester thereof and one or more sugars and which incorporates a polypeptide, preferably within a matrix formed by the sugar, and wherein when the composition is analysed by differential scanning calorimetry (DSC), no crystalline melt endotherms are observed and preferably no re-crystallisation exotherms are observed;
- a freeze-dried composition comprising a compound of formula (I) or a physiologically acceptable salt or ester thereof and/or a compound of formula (II) or a physiologically acceptable salt or ester thereof and one or more sugars and which incorporates a polypeptide, preferably within a matrix formed by the sugar, and wherein when the composition is analysed by differential scanning calorimetry (DSC), no crystalline melt endotherms are observed and preferably no re-crystallisation exotherms are observeed;
- a solid freeze-dried cake comprising a compound of formula (I) or a physiologically acceptable salt or ester thereof and/or a compound of formula (II) or a physiologically acceptable salt or ester thereof and one or more sugars and which incorporates a polypeptide, preferably within a matrix formed by the sugar, and wherein when the composition is analysed by differential scanning calorimetry (DSC), no crystalline melt endotherms are observed and preferably no re-crystallisation exotherms are observed, The solid composition is typically provided as a powder in a sealed vial, ampoule or syringe. If for inhalation, the powder can be provided in a dry powder inhaler. The solid matrix can alternatively be provided as a patch. A powder may be compressed into tablet form.

The composition may typically consist, or consist essentially, of polypeptide, a compound of formula (I) or a physiologically acceptable salt or ester thereof and/or a compound of formula (II) or a physiologically acceptable salt or ester thereof, and one or more sugars.

Measuring Polypeptide Preservation

Preservation in relation to a polypeptide such as a hormone, growth factor, peptide or cytokine refers to resistance of the polypeptide to physical or chemical degradation, aggregation and/or loss of biological activity such as the ability to stimulate cell growth, cell proliferation or cell differentiation, ability to stimulate cell signalling pathways, bind hormone receptors or preserve epitopes for antibody binding, under exposure to conditions of desiccation, freezing, temperatures below 0° C., below –5° C., below –10° C., below –15° C., below –20° C. or below –25° C., freeze-drying, room temperature, temperatures above –10° C., above –5° C., above 0° C., above 5° C., above 10° C., above 15° C., above 20° C., above 25° C. or above 30° C. The preservation of a polypeptide may be measured in a number of different ways. For example the physical stability of a polypeptide may be measured using means of detecting aggregation, precipitation and/or denaturation, as determined, for example upon visual examination of turbidity or of colour and/or clarity as measured by UV light scattering or by size exclusion chromatography.

The assessment of preservation of biological activity of the polypeptide will depend on the type of biological activity being assessed. For example, the ability of a growth factor to stimulate cell proliferation can be assessed using a number of different techniques well known in the art, (such as cell culture assays that monitor cells in S-phase, or the incorporation of base analogs (e.g. bromodeoxyuridine (BrdU)) as an indication of changes in cell proliferation. Various aspects of cell proliferation, or cell differentiation may be monitored using techniques such as immunofluorescence, immunoprecipitation, immunohistochemistry.

The assessment of preservation of epitopes and formation of antibody-polypeptide complexes may be determined using an immunoassay e.g. an Enzyme-linked Immunosorbant assay (ELISA).

Uses of the Preserved Polypeptides of the Invention

The amorphous form of the preserved polypeptide enables the polypeptide to be stored for prolonged periods of time and maximises the shelf-life of the polypeptide. The potency and efficacy of the polypeptide is maintained. The particular use to which a polypeptide preserved according to the present invention is put depends on the nature of the polypeptide. Typically, however, an aqueous solution of the polypeptide is reconstituted from the dried amorphous solid matrix incorporating the polypeptide prior to use of the polypeptide.

In the case of a therapeutic polypeptide such as a hormone, growth factor, peptide or cytokine, an aqueous solution of the polypeptide can be reconstituted by addition of for example Sterile Water for Injections or phosphate-buffered saline to a dry powder comprising the preserved polypeptide. The solution of the polypeptide can then be administered to a patient in accordance with the standard techniques. The administration can be by any appropriate mode, including parenterally, intravenously, intramuscularly, intraperitoneally, transdermally, via the pulmonary route, or also, appropriately by direct infusion with a catheter. The dosage and frequency of administration will depend on the age, sex and condition of the patient, concurrent administration of other drugs, counter indications and other parameters to be taken into account by the clinician.

Generally, a therapeutic polypeptide preserved according to the invention is utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension may be chosen from thickeners such as carboxymethylcellulose, polvinylpyrrolidine, gelatine and alginates. Intravenous vehicles include fluid and nutrient replenishers and electrolyte replenishers such as those based on Ringers dextrose. Preservative and other additives, such as antimicrobials, antioxidants, chelating agents and inert gases may also be present.

Other polypeptides preserved according to the invention can, as noted above, be used as diagnostic agents.

Measuring Antibody or Antigen-Binding Fragment Preservation

Preservation in relation to an antibody or antigen-binding fragment refers to resistance of the antibody or antigen-binding fragment to physical or chemical degradation and/or loss of biological activity such as protein aggregation or degradation, loss of antigen-binding ability, loss of ability to neutralise targets, stimulate an immune response, stimulate effector cells or activate the complement pathway, under exposure to conditions of desiccation, freezing, temperatures below 0° C., below −5° C., below −10° C., below −15° C., below −20° C. or below −25° C., freeze-drying, room temperature, temperatures above −10° C., above −5° C., above 0° C., above 5° C., above 10° C., above 15° C., above 20° C., above 25° C. or above 30° C.

The preservation of an antibody or antigen-binding fragment thereof may be measured in a number of different ways.

For example, the physical stability of antibodies may be measured using means of detecting aggregation, precipitation and/or denaturation, as determined, for example upon visual examination of turbidity and/or clarity as measured by light scattering or by size exclusion chromatography.

Chemical stability of antibodies or antigen-binding fragments may be assessed by detecting and quantifying chemically altered forms of the antibody or fragment. For example changes in the size of the antibody or fragment may be evaluated using size exclusion chromatography, SDS-PAGE and/or matrix-assisted laser desorption ionization/time-of-flight mass spectrometry (MALDI/TOF MS). Other types of chemical alteration including charge alteration, can be evaluated using techniques known in the art, for example, by ion-exchange chromatography or isoelectric focussing.

The preservation of biological activity of the antibody or antigen-binding fragment may also be assessed by measuring the ability of the antibody or antigen-binding fragment for example, to bind antigen, raise an immune response, neutralise a target (e.g. a pathogen), stimulate effector functions (e.g. opsonization, phagocytosis, degranulation, release of cytokins or cytotoxins) or activate complement pathway. Suitable techniques for measuring such biological functions are well known in the art. For example an animal model may be used to test biological functions of an antibody or antigen-binding fragment. An antigen-binding assay such as an immunoassay, may be used for example to detect antigen-binding ability.

Determining whether the antibody binds an antigen in a sample may be performed by any method known in the art for detecting binding between two protein moieties. The binding may be determined by measurement of a characteristic in either the antibody or antigen that changes when binding occurs, such as a spectroscopic change. The ability of a preserved antibody or antigen-binding fragment to bind an antigen may be compared to a reference antibody (e.g. an antibody with the same specificity of the preserved antibody or antigen-binding fragment, that has not been preserved according to the methods described herein).

Generally the method for detecting antibody-antigen binding is carried out in an aqueous solution. In particular embodiments, the antibody or antigen is immobilized on a solid support. Typically, such a support is a surface of the container in which the method is being carried out, such as the surface of a well of a microtiter plate. In other embodiments, the support may be a sheet (e.g. a nitrocellulose or nylon sheet) or a bead (e.g. Sepharose or latex).

In a preferred embodiment, the preserved antibody sample is immobilized on a solid support (such as the supports discussed above). When the support is contacted with antigen, the antibody may bind to and form a complex with the antigen. Optionally, the surface of the solid support is then washed to remove any antigen that is not bound to the antibody. The presence of the antigen bound to the solid support (through the binding with the antibody) can then be determined, indicating that the antibody is bound to the antigen. This can be done for example by contacting the solid support (which may or may not have antigen bound to it) with an agent that binds to the antigen specifically.

Typically the agent is a second antibody which is capable of binding the antigen in a specific manner whilst the antigen is bound to the first immobilised sample antibody that also binds the antigen. The secondary antibody may be labelled either directly or indirectly by a detectable label. The second antibody can be labelled indirectly by contacting with a third antibody specific for the Fc region of the second antibody, wherein the third antibody carries a detectable label.

Examples of detectable labels include enzymes, such as a peroxidose (e.g. of horseradish), phosphatase, radioactive elements, gold (or other colloid metal) or fluorescent labels. Enzyme labels may be detected using a chemiluminescence or chromogenic based system.

In a separate embodiment, the antigen is immobilised on a solid support and the preserved antibody is then contacted with the immobilised antigen. The antigen-antibody complexes may be measured using a second antibody capable of binding antigen or the immobilised antibody.

Heterogeneous immunoassays (requiring a step to remove unbound antibody or antigen) or homogenous immunoassays (not requiring this step) may be used to measure the ability of preserved antibody or antigen-binding fragments to bind antigen. In a homogenous assay, in contrast to a heterogeneous assay, the binding interaction of candidate antibody with an antigen can be analysed after all components of the assay are added without additional fluid manipulations being required. Examples include fluorescence resonance energy transfer (FRET) and Alpha Screen. Competitive or non-competitive heterogeneous immunoassays may be used. For example, in a competitive immunoassay, unlabelled preserved antibody in a test sample can be measured by its ability to compete with labelled antibody of known antigen-binding ability (a control sample e.g. an antibody sampled before desiccation, heat treatment, freeze-drying and/or storage). Both antibodies compete to bind a limited amount of antigen. The ability of unlabelled antibody to bind antigen is inversely related to the amount of label measured. If an antibody in a sample is able to inhibit the binding between a reference antibody and antigen, then this indicates that such an antibody is capable of antigen-binding.

Particular assays suitable for measuring the antigen-binding ability of the preserved antibodies of the invention include enzyme-linked immunoassays such as Enzyme-Linked ImmunoSorbent Assay (ELISA), homogenous binding assays such as fluorescence resonance energy transfer (FRET), Fluorescence Polarization Immunoassay (FPIA), Microparticle Enzyme Immunoassay (MEIA), Chemiluminescence Magnetic Immunoassay (CMIA), alpha-screen surface plasmon resonance (SPR) and other protein or cellular assays known to those skilled in the art for assaying antibody-antigen interactions.

In one embodiment, using the ELISA assay, an antigen is brought into contact with a solid support (e.g. a microtiter plate) whose surface has been coated with an antibody or antigen-binding fragment preserved according to the present invention (or a reference antibody e.g. one that has not been preserved according to the method of the invention). Optionally, the plate is then washed with buffer to remove non-specifically bound antibody. A secondary antibody that is able to bind the antigen is applied to the plate and optionally, followed by another wash. The secondary antibody can be linked directly or indirectly to a detectable label. For example, the secondary antibody may be linked to an enzyme e.g. horseradish peroxidase or alkaline phosphatase, which produces a colorimetric produce when appropriate substrates are provided.

In a separate embodiment, the solid support is coated with the antigen and the preserved antibody or antigen-binding fragment is brought into contact with the immobilised antigen. An antibody specific for the antigen as preserved antibody may be used to detect antigen-antibody complexes.

In a further embodiment, the binding interaction of the preserved antibody and a target is analysed using Surface Plasmon Resonance (SPR). SPR or Biomolecular Interaction Analysis (BIA) detects biospecific interactions in real-time without labelling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules.

Information from SPR can be used to provide an accurate and quantitative measure of the equilibrium disassociation constant ($D_D$), and kinetic parameters, including $K_{on}$ and $K_{off}$ for the binding of a biomolecule to a target.

Typically, the ability of an antibody to form antibody-antigen complexes following preservation according to the present invention and incubation of the resulting product at 37° C. for 7 days is at least 10%, at least 20%, at least 30%, at least 40%, at least 50%, at least 60%, at least 70%, at least 80% or at least 90% of the ability of the antibody to form such complexes prior to such incubation, or indeed prior to preservation according to the present invention and such incubation.

Uses of Preserved Antibodies or Antigen-Binding Fragments Thereof

Preserved antibodies or antigen-binding fragments thereof may be employed in in vivo therapeutic and prophylactic applications, in vitro and in vivo diagnostic applications and in in vitro assay and reagent applications.

In diagnostic applications, body fluids such as blood, urine, saliva, sputum, gastric juices, other blood fluid components, urine or saliva, or body tissue, may be assayed for the presence and amount of antigen that binds to the preserved antibodies or antigen-binding fragments. The assay may be performed by a number of routine methods known in the art such as immunoassays (e.g. RIA, ELISA).

For example, a sample of bodily fluid may be added to an assay mixture containing the antibody and a marker system for detection of antigen-bound antibody. By comparing the results obtained using a test sample with those obtained using a control sample, the presence of an antigen specific to a particular disease or condition may be determined. Such methods for qualitatively or quantitatively determining the antigen associated with a particular disease or condition may be used in the diagnosis of that disease or condition.

Other techniques may be used in diagnostic applications such as Western analysis and in situ protein detection by standard immunohistochemical procedures, wherein the preserved antibody or antigen-binding fragment may be labelled as appropriate for the particular technique used. Preserved antibodies or antigen-binding fragments may also be used in affinity chromatography procedures when complexed to a chromatographic support, such as a resin.

Diagnostic applications include human clinical testing in hospitals, doctors offices and clinics, commercial reference laboratories, blood banks and the home. Non-human diagnostics applications include food testing, water testing, environmental testing, bio-defence, veterinary testing and in biosensors.

Preserved antibodies or antigen-binding fragments may also be used in research applications such as in drug development, basic research and academic research. Most commonly, antibodies are used in research applications to identify and locate intracellular and extracellular proteins. The preserved antibodies or antigen binding fragments described herein may be used in common laboratory techniques such as flow cytometry, immunoprecipitation, Western Blots, immunohistochemistry, immunofluorescence, ELISA or ELISPOT.

Preserved antibodies or antigen-binding fragments for use in diagnostic, therapeutic or research applications may be stored on a solid support. In diagnostic applications for example, a patient sample such as bodily fluid (blood, urine, saliva, sputum, gastric juices etc) may be preserved according to the methods described herein by drying an admixture comprising the patient sample and preservation mixture of the present invention onto a solid support (e.g. a microtiter plate, sheet or bead). Preserved patient samples (e.g. serum) may then be tested for the presence of antibodies in the sample using for example, immunoassays such as ELISA.

Alternatively, antibodies or antigen-binding fragments of interest may be preserved according to the methods described herein by drying an admixture comprising the antibody or antigen-binding fragment and preservation mixture of the present invention onto a solid support. Patient samples may be tested for the presence of particular antigens by contacting the patient sample with a solid support onto which the antibodies or antigen-binding fragments of interest are attached. The formation of antigen-antibody complexes can elicit a measurable signal. The presence and/or amount of antigen-antibody complexes formed may be used to indicate the presence of a disease, infection or medical condition or provide a prognosis.

For therapeutic applications, the preserved antibodies or antigen-binding fragments described herein will typically find use in preventing, suppressing or treating inflammatory states, allergic hypersensitivity, cancer, bacterial or viral infection and/or autoimmune disorders (including for example, but not limited to, Type I diabetes, multiple sclerosis, rheumatoid arthritis, systemic lupus erythematosus, Crohn's disease and myasthenia gravis).

The antibody may itself be a therapeutic agent or may target a therapeutic agent or other moiety to a particular cell type, tissue or location. In one embodiment, preserved antibodies or antigen-binding fragments of the invention are conjugated to radioisotopes, toxins, drugs (e.g. chemotherpeutic drugs), enzyme prodrugs or liposomes for the treatment of a variety of diseases or conditions.

Measuring Enzyme Preservation

Preservation in relation to an enzyme refers to resistance of the enzyme to physical degradation and/or loss of biological activity such as protein degradation, reduced catalytic activity, loss of ability to bind substrate, reduced product production, enzyme efficiency (e.g. reduced $k_{cat}/K_m$) or rate of reaction, under exposure to conditions of desiccation, freezing, temperatures below 0° C., below −5° C., below −10° C., below −15° C., below −20° C. or below −25° C., freeze-drying, room temperature, temperatures above −10° C., above −5° C., above 0° C., above 5° C., above 10° C., above 15° C., above 20° C., above 25° C. or above 30° C. The preservation of an enzyme may be measured in a number of different ways. For example the physical stability of an enzyme may be measured using means of detecting aggregation, precipitation and/or denaturation, as determined, for example upon visual examination of turbidity or of colour and/or clarity as measured by UV light scattering or by size exclusion chromatography.

The preservation of catalytic activity of the enzyme may be assessed using an enzyme assay to measure the consumption of substrate or production of product over time. The catalytic activity of a preserved enzyme may be compared with a reference enzyme having the same specificity that has not been preserved according to the present invention.

Changes in the incorporation of radioisotopes, fluorescence or chemiluminescence of substrates, products or cofactors of an enzymatic reaction or substances bound to such substrates, products or cofactors, may be used to monitor the catalytic activity of the enzyme in such assays.

For example, a continuous enzyme assay may be used (e.g. a spectrophotometric assay, a fluorimetric assay, calorimetric assay, chemiluminescent assay or light scattering assay) or a discontinuous enzyme assay (e.g. a radiometric or chromatographic assay). In contrast to continuous assays, discontinuous assays involve sampling of the enzyme reaction at specific intervals and measuring the amount of product production or substrate consumption in these samples.

For example, spectrophotometric assays involve the measurement of changes in the absorbance of light between products and reactants. Such assays allow the rate of reaction to be measured continuously and are suitable for enzyme reactions that result in a change in the absorbance of light. The type of spectrophotometric assay will depend on the particular enzyme/substrate reaction being monitored. For example, the coenzymes NADH and NADPH absorb UV light in their reduced forms, but do not in their oxidised forms. Thus, an oxidoreductase using NADH as a substrate could therefore be assayed by following the decrease in UV absorbance as it consumes the coenzyme.

Radiometric assays involve the incorporation or release of radioactivity to measure the amount of product made over the time during an enzymatic reaction (requiring the removal and counting of samples). Examples of radioactive isotopes suitable for use in these assays include $^{14}C$, $^{32}P$, $^{35}C$ and $^{125}I$. Techniques such as mass spectrometry may be used to monitor the incorporation or release of stable isotopes as substrate is converted into product.

Chromatographic assays measure product formation by separating the reaction mixture into its components by chromatography. Suitable techniques include high-performance liquid chromatography (HPLC) and thin layer chromatography.

Fluorimetric assays use a difference in the fluorescence of substrate from product to measure the enzyme reaction. For example a reduced form may be fluorescent and an oxidised form non-fluorescent. In such an oxidation reaction, the reaction can be followed by a decrease in fluorescence. Reduction reactions can be monitored by an increase in fluorescence. Synthetic substrates can also be used that release a fluorescent dye in an enzyme catalysed reaction.

Chemiluminescent assays can be used for enzyme reactions that involve the emission of light. Such light emission can be used to detect product formation. For example an enzyme reaction involving the enzyme luciferase involves production of light from its substrate luciferin. Light emission can be detected by light sensitive apparatus such as a luminometer or modified optical microscopes.

Uses of the Preserved Enzymes of the Invention

The amorphous form of the preserved enzyme enables the enzyme to be stored for prolonged periods of time and maximises the shelf-life of the enzyme. The potency and efficacy of the enzyme is maintained. The particular use to which an enzyme preserved according to the present invention is put depends on the nature of the enzyme. Typically, however, an aqueous solution of the enzyme is reconstituted from the dried amorphous solid matrix incorporating the enzyme prior to use of the enzyme.

In the case of a therapeutic enzyme for example, an aqueous solution of the enzyme can be reconstituted by addition of for example Water for Injections or phosphate-buffered saline to a dry powder comprising the preserved enzyme. The solution of the enzyme can then be administered to a patient in accordance with the standard techniques. The administration can be by any appropriate mode, including parenterally, intravenously, intramuscularly, intraperitoneally, transdermally, via the pulmonary route, or also, appropriately by direct infusion with a catheter. The dosage and frequency of administration will depend on the age, sex and condition of the patient, concurrent administration of other drugs, counter indications and other parameters to be taken into account by the clinician.

Generally, a therapeutic enzyme preserved according to the invention is utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension may be chosen from thickeners such as carboxymethylcellulose, polvinylpyrrolidine, gelatine and alginates. Intravenous vehicles include fluid and nutrient replenishers and electrolyte replenishers such as those based on Ringers dextrose. Preservative and other additives, such as antimicrobials, antioxidants, chelating agents and inert gases may also be present.

Other enzymes preserved according to the invention can, as noted above, be used as diagnostic agents, in bio sensors, in the production of bulk products such as glucose or fructose, in food processing and food analysis, in laundry and automatic dishwashing detergents, in the textile, pulp, paper and animal feed industries, as a catalyst in the synthesis of fine chemicals, in clinical diagnosis or in research applications such as genetic engineering.

Measuring Vaccine Immunogen Preservation

Preservation in relation to a vaccine immunogen refers to resistance of the vaccine immunogen to physical or chemical degradation and/or loss of biological activity such as protein degradation, loss of ability to stimulate a cellular or humoral immune response or loss of ability to stimulate antibody production or bind antibodies under conditions of desiccation, freezing, temperatures below 0° C., below −5° C., below −10° C., below −15° C., below −20° C. or below −25° C., freeze-drying, room temperature, temperatures above −10° C., above −5° C., above 0° C., above 5° C., above 10° C., above 15° C., above 20° C., above 25° C. or above 30° C.

The preservation of a vaccine immunogen may be measured in a number of different ways. For example, antigenicity may be assessed by measuring the ability of a vaccine immunogen to bind to immunogen-specific antibodies. This can be tested in various immunoassays known in the art, which can detect antibodies to the vaccine immunogen. Typically an immunoassay for antibodies will involve selecting and preparing the test sample, such as a sample of preserved vaccine immunogen (or a reference sample of vaccine immunogen that has not been preserved in accordance with the methods of the present invention) and then incubating with antiserum specific to the immunogen in question under conditions that allow antigen-antibody complexes to form.

Further, antibodies for influenza haemagglutinin and neuraminidase can be assayed routinely in the haemagglutanin-inhibition and neuraminidase-inhibition tests, an agglutination assay using erythrocytes, or using the single-radial diffusion assay (SRD). The SRD is based on the formation of a visible reaction between the antigen and its homologous antibody in a supporting agarose gel matrix. The virus immunogen is incorporated into the gel and homologous antibodies are allowed to diffuse radially from points of application through the fixed immunogens. Measurable opalescent zones are produced by the resulting antigen-antibody complexes.

Uses of Preserved Vaccine Immunogens

A preserved vaccine immunogen of the present invention is used as a vaccine. For example, a preserved subunit vaccine immunogen, conjugate vaccine immunogen or toxoid immunogen is suitable for use as a subunit, conjugate or toxoid vaccine respectively. As a vaccine the preserved vaccine immunogens of the invention may be used for the treatment or prevention of a number of conditions including but not limited to viral infection, sequelae of viral infection including but not limited to viral-, animal- or insect-induced toxicity, cancer and allergies. Such antigens contain one or more epitopes that will stimulate a host's immune system to generate a humoral and/or cellular antigen-specific response.

The preserved vaccine immunogen of the invention may be used as a vaccine in the prophylaxis or treatment of infection by viruses such as human papilloma viruses (HPV), HIV, HSV2/HSV1, influenza virus (types A, B and C), para influenza virus, polio virus, RSV virus, rhinoviruses, rotaviruses, hepaptitis A virus, norwalk virus, enteroviruses, astroviruses, measles virus, mumps virus, varicella-zoster virus, cytomegalovirus, epstein-barr virus, adenoviruses, *rubella* virus, human T-cell lymphoma type I virus (HTLV-I), hepatitis B virus (HBV), hepatitis C virus (HCV), hepatitis D virus, poxvirus, and vaccinia virus. The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and bovine viral diarrhoea virus. Alternatively, the vaccine may be used to provide a suitable immune response against animal- or insect-induced toxicity (for example as induced by snake venom or other animal poisons). In one embodiment, the vaccine is a multivalent vaccine.

The vaccine compositions of the present invention comprise a vaccine immunogen admixed with the preservation mixture of the invention containing one or more sugars and PEI. The vaccine composition may further comprise appropriate buffers and additives such as antibiotics, adjuvants or other molecules that enhance presentation of the vaccine immunogen to specific cells of the immune system.

A variety of adjuvants well known in the art can be used in order to increase potency of the vaccine and/or modulate humoral and cellular immune responses. Suitable adjuvants include, but are not limited to, oil-in-water emulsion-containing adjuvants or water in oil adjuvants, such as mineral oil, aluminium-based adjuvants, squalene/phosphate based adjuvants, Complete/Incomplete Freunds Adjuvant, cytokines, an immune stimulating complex (ISCOM) and any other substances that act as immuno stimulating agents to enhance the effectiveness of the vaccine. The aluminium-based adjuvant includes aluminium phosphate and aluminium hydroxide. An ISCOM may comprise cholesterol, lipid and/or saponin. The ISCOM may induce a wide range of systemic immune responses.

The vaccine composition of the present invention can be in a freeze-dried (lyophilised) form in order to provide for appropriate storage and maximize the shelf-life of the preparation. This will allow for stock piling of vaccine for prolonged periods of time and help maintain immunogenicity, potency and efficacy. The preservation mixture of the present invention is particularly suited to preserve viral substances against desiccation and thermal stresses encountered during freeze-drying/lyophilisation protocols. Therefore, the preservation mixture is suitable for adding to the vaccine immunogen soon after harvesting and before subjection of the sample to the freeze-drying procedure.

To measure the preservation of a vaccine prepared in accordance with the present invention, the potency of the vaccine can be measured using techniques well known to those skilled in the art. For example, the generation of a cellular or humoral immune response can be tested in an appropriate animal model by monitoring the generation of antibodies or immune cell responses to the vaccine. The ability of vaccine samples prepared in accordance with the method of the present invention to trigger an immune response may be compared with vaccines not subjected to the same preservation technique.

Administration

Preserved polypeptides according to the present invention may be administered, in some instances after reconstitution of a dried or freeze-dried product, to a subject in vivo using a variety of known routes and techniques. For example, the polypeptides can be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. Polypeptides may be administered topically to skin or mucosal tissue, such as nasally, intratrachealy, intestinal, sublingually, rectally or vaginally, or provided as a finely divided spray suitable for respiratory or pulmonary administration.

In one embodiment, the method of the invention further comprises the step of processing the mixture into a formulation suitable for administration as a liquid injection. Preferably, the method further comprises the step of processing the mixture into a formulation suitable for administration via ingestion or via the pulmonary route.

The preserved product is administered to a subject in an amount that is compatible with the dosage formulation and that will be prophylactically and/or therapeutically effective. The administration of the preserved product of the invention may be for either "prophylactic" or "therapeutic" purpose. As used herein, the term "therapeutic" or "treatment" includes any of the following: the prevention of infection or reinfection; the reduction or elimination of symptoms; and the reduction or complete elimination of a pathogen. Treatment may be effected prophylactically (prior to infection) or therapeutically (following infection).

The compound of formula (I) or physiologically acceptable salt or ester thereof and/or compound of formula (II) or physiologically acceptable salt or ester thereof and, optionally, one or more sugars, typically acts as a resuspension agent for a dried or freeze-dried product comprising polypeptides, preferably a product of the invention, for example when it is converted into liquid form (aqueous solution) prior to administration to a patient.

The following Examples illustrate the invention.

Materials and Equipment

The following materials, equipment and techniques were employed unless stated otherwise:

| | Supplier | Product Code | Lot No. |
|---|---|---|---|
| Dulbecco's phosphate buffered saline (PBS) | Sigma | D8662 | RNBB2193, RNBB4780, RNBB6651 |
| Dimethylglycine (DMG) | Sigma | D1156 | 077K1856 |
| Dimethylsulphone | Sigma | M81705 | 0001452516 |
| Mannitol | Sigma | M1902 | 077K0166 |
| Sucrose | Sigma | 16104 | SZB90120 |
| Raffinose | Sigma | R0250 | 050M0053 |
| Tween 20 | Sigma | P1379 | 087K0197 |
| Skimmed milk powder | Marvel | — | — |
| TMB chromogen | Invitrogen | SB02 | 72764382A |
| Sulphuric acid | Sigma | 25,8105 | S55134-258 |
| HPLC Grade Water | Sigma | 34877-2.5L | BCBG1213V |
| Sodium Sulphate | VWR | 28111.296 | 07G160005 |
| Potassium Sulphate | Sigma | 71840-1KG | 0001451144 |
| Acetate buffer | Sigma | 31103 | SZBB0540 |
| Foetal Bovine Serum | Sigma | F7524 | 111B77F2311 |
| Granulocyte-colony stimulating factor (G-CSF) | Sigma | 300-23 | 5110901099 |
| Macrophage-colony stimulating factor (M-CSF) | Sigma | 130-093-860 | RNBB6654 |
| Penicillin streptomycin | Sigma | P4458 | 030M0695 |
| Growth medium (RPMI) | Sigma | R8758 | RNBB8596 |
| Water | Sigma | W3500 | RNBB8005 |
| Sodium salt of 2,3-bis[2-methoxy-4-nitro-5sulfophenyl]-2H-tetrazolium-5 carboxyanilide inner salt (XTT) | Sigma | TOX2 | 078K8403 |
| β-Mercaptoethanol | Sigma | M7522 | 01496DK |

| | Supplier | Product Code |
|---|---|---|
| Bivalent $F(ab')_2$ | AbDSerotec | AbD09357.4 |
| Antigen - IgG2b kappa | AbDSerotec | PRP05 |
| Goat anti human HRP | AbDSerotec | STAR126P |
| Rabbit anti mouse HRP | AbDSerotec | STAR13B |
| Normal mouse serum | Sigma | M5905 |
| Mouse anti *Neisseria gonorrhoeae* | AbDSerotec | 6600-1205 |
| Antigen - *Neisseria gonorrhoeae* | AbDSerotec | MPP017X |
| HRP -conjugated Mouse anti *Neisseria gonorrhoeae* IgG | AbDSerotec | 6600-1205MX |
| HPLC-SEC Size Standards | BioRAD | 1901-151 |
| Monovalent Fab | AbDSerotec | AbD12385.2 |
| M-NFS-60 cell line | LGC | CRL-1838 |

| | Manufacturer | Product Code |
|---|---|---|
| 2 ml eppendorf tubes | VWR | 16466-058 |
| Forma 900 series −80° C. freezer | Thermofisher | |
| Virtis Freeze Dryer | Virtis | |
| ATL-84-1 Atlion Balance | Acculab | |
| Med Line +4° C. fridge | Liebherr | |
| +40° C. incubator | Binder | |
| Synergy HT Microplate reader | Biotek | |
| Med Line +4° C. fridge | Liebherr | |
| LEC +4° C. fridge 1132880 | LEC | |
| +37° C. shaking incubator | Max Q 4450 | |
| HPLC Separations Module | Waters | |

-continued

| | |
|---|---|
| HPLC PhotoDiode Array Detector | Waters |
| HPLC Column Oven | Waters |
| HPLC-SEC Separations Column (TSKGel G3000SWxl 7.8 mm × 30 cm) | Sigma |
| HPLC-SEC Guard Column (SWxl Guardcol 6.0 mm × 4.0 cm) | Sigma |
| Temperature monitoring system | Kelsius |
| BD115 56° C. incubator | Binder |
| Binder $CO_2$ Incubator | Binder |
| BP61 Balance | Sartorius |
| G560E Vortex | VortexGenie |
| IP250 37° C. Incubator | LTE |
| JB Aqua 5 VAB05EU Waterbath | Grant |
| KEN SJ/5538 Microwave | Kenwood |
| Microbiological Safety cabinets | Biomat |
| Profiline refrigerator (stock storage) | Liebherr |
| Excipients Mannitol and TMG | HEPES + 25 mM NaCl @ pH 7.9 (LBN0014p34) |
| rPA | Freeze dry vials |
| Bungs | PBS |
| Tween20 Sigma P1379 | Milk Marvel |
| *Bacillus anthracis* mAb | Goat anti mouse IgG-HRP |
| Fitzgerald 10R- | Sigma |
| B106a clone 3 | A0412 |
| TMB Invitrogen SB02 | $H_2SO_4$ Sigma 25 810-5 |
| Flat bottom plates Nunc 439454 | Water |
| FD vials Schott VCDIN2R | 14 mm FD stopper Adelphi healthcare W1816 |
| 13 mm aluminium seal Adelphi healthcare COTW13 | |
| Flat bottom plates Nunc 439454 | Sample buffer Biorad 161-0737 |
| Molecular marker Biorad 161-0319 | Running buffer Biorad 161-0772 |
| 4-20% TGX gels Biorad 456-1096 | Coomassie brilliant blue Fisher 101-25 |
| Methanol VWR 20486.326 | Acetic acid Fisher A/0360/PB08 |
| Glycerol Sigma G9012 | Isopropanol VWR 20839.322 |

EXAMPLE 1

Bivalent $F(ab')_2$ was thermally challenged in the presence of various concentrations of excipients and assayed at different points. An ELISA assay was used to assess the residual $F(ab')_2$ activity—this was used as a measure of the extent of damage sustained during the thermal challenge.

Methods

Preparation and Thermal Challenge of Bivalent $F(ab)_2$ in a Solid Setting with Excipients Bivalent $F(ab')_2$ in PBS was removed from storage at −80° C. and allowed to thaw at room temperature. To determine the protective properties of the excipients described below in a solid setting, 300 μl of each formulation with an antibody concentration of 6.67 μg/ml was aliquoted into glass freeze drying vials. Details of each formulation are set out in Table 1.

TABLE 1 details of excipient formulations

| Abbreviation | Description | DMG | mannitol |
|---|---|---|---|
| [Hi]DMG/man | [high] DMG, [fixed] mannitol | 1M | 0.5M |
| [Med]DMG/man | [middle] DMG, [fixed] mannitol | 0.7M | 0.5M |
| [Lo]DMG/man | [low] DMG, [fixed] mannitol | 0.3M | 0.5M |

TABLE 1-continued details of excipient formulations

| Abbreviation | Description | DMG | mannitol |
|---|---|---|---|
| −DMG/man | no DMG, [fixed] mannitol | — | 0.5M |
| −DMG/−man | no DMG/no mannitol, PBS only | — | — |

Ten vials of each formulation were made up, to assess five timepoints in duplicate.

The samples were then lyophilized using a VirTis Advantage freeze dryer on recipe 6, using the drying cycles shown in Table 2 below. Samples were frozen at −40° C. for 45 minutes before a vacuum was applied, initially at 200 milliTorre. Shelf temperature and vacuum were adjusted throughout the process.

In the primary drying phase the shelf temperature was initially dropped to −40° C. The secondary drying phase included series of hold steps increasing in temperature up to 30° C. until the drying was completed. Probes recorded shelf temperatures and condenser temperatures.

TABLE 2

| Step | Shelf temp (° C.) | Time (mins) | Ramp/Hold | Vacuum (milliTorre) |
|---|---|---|---|---|
| 1 | −45 | 15 | H | 200 |
| 2 | −36 | 600 | H | 300 |
| 3 | −20 | 120 | R | 300 |
| 4 | −10 | 120 | R | 300 |
| 5 | 0 | 120 | R | 300 |
| 6 | 10 | 120 | R | 80 |
| 7 | 20 | 120 | R | 80 |
| 8 | 30 | 1255 | R | 80 |
| 9 | 4 | 1255 | R | 80 |

Once lyophilised, the vials were photographed to document the quality of the cakes produced, then placed in a +40° C. incubator to begin thermal challenge.

Assay of Bivalent F(ab)$_2$ Activity

The activity of the Bivalent F(ab')$_2$ was assayed by ELISA. Antigen (Rat IgG2b-kappa) diluted to 0.5 µg/ml in PBS was coated 100 µl/well in row A to G of a 96-well ELISA plate, as well as two extra wells in row H for the +4° C. control condition. These controls were used to normalise data later. Plates were incubated for 18 hours at +4° C. then washed three times with PBS containing 0.05% Tween 20 (wash buffer). Plates were dried by blotting onto a paper towel. This method of blotting was used in every wash step. Plates were blocked for 1.5 hours with PBS containing 5% skimmed milk powder and 0.05% Tween 20. Plates were washed three times with wash buffer before adding the samples.

After incubation at thermal challenge, the F(ab')$_2$ formulations were removed from incubator and reconstituted in 1 ml of wash buffer—this resulted in the required antibody concentration for the ELISA (2 µg/ml). Each diluted sample was added to the plate in duplicate and was diluted 2-fold down the plate (final concentrations ranging from 2 µg/ml to 0.0625 µg/ml). A condition with no bivalent F(ab')$_2$ was also included to measure the background signal. The positive control condition was assayed at 2 µg/ml. The plates were incubated at room temperature for 1.5 hours after which time the plates were washed five times with wash buffer.

A goat anti-human HRP conjugated antibody was diluted 1:5000 in wash buffer and 100 µl added to all the wells containing bivalent F(ab')$_2$. The plates were incubated at room temperature for 1.5 hours then washed five times with wash buffer. 100 µl of TMB stabilised chromogen was added to each well and was allowed to react for 10 minutes at room temperature, after which time 100 µl 200 mM sulphuric acid was added to stop the reaction. The plates were read at 450 nm using Synergy HT Microplate reader.

Statistical Analysis

The average and standard error were taken for each duplicate and the data points plotted as a bar graph at a designated F(ab')$_2$ concentration.

The results were normalised to the bivalent F(ab')$_2$ positive control (a sample taken from the stock aliquot which had not been mixed with excipients or thermally challenged). Results were divided by the average of the two positive control wells for the plate (each plate had a separate positive control).

A student's t-test was carried out at the 9 month time point to determine the significance between the samples lyophilised and stored with excipients and those lyophilised and stored with only PBS. The the P-values for formulations T-tested against PBS only samples at 9 months (n=4, two tailed student's t-test) are set out in Table 3.

TABLE 3

| Formulations T-tested against PBS only sample | P value |
|---|---|
| HiDMG | 0.000127319 |
| MedDMG | 0.12493135 |
| LoDMG | 0.000587714 |

Results

Activity of Bivalent F(ab')$_2$ Fragments after Thermal Treatment at +56° C. For 24 Hours in a Liquid Setting.

Figure 1:
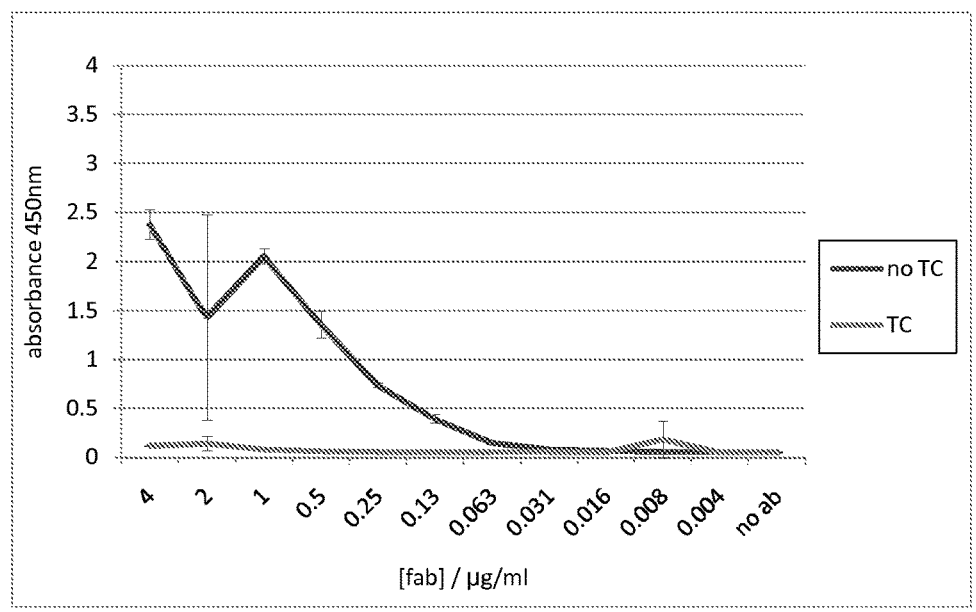
FIG. 1 shows the results from an initial thermal challenge study on F(ab')$_2$ at 56° C. for 24 hours in Example 1. TC denotes thermal challenge. The data are not normalized and error bars are standard deviation, n=2. The results shows that F(ab')$_2$ is extremely heat labile.

In a preliminary study, stock F(ab')$_2$ (as supplied by AbD Serotec—concentration 0.73 mg/ml) was stored at +56° C. to assess initial stability at elevated temperatures. The antibody was found to be extremely heat labile with little activity remaining after 24 hours at 56° C., providing an excellent starting point for testing the ability of the excipients to stabilise this antibody. The results are depicted in FIG. 1, where TC denotes thermal challenge (data not normalized) and error bars are standard deviation, n=2.

Activity of Bivalent F(Ab)$_2$ Fragments after Thermal Treatment at +40° C. With and without Excipients in a Solid Setting.

The bivalent F(ab')$_2$ was thermally challenged in the presence of various concentrations of the excipients and assayed at different timepoints (1, 2, 3, 6 and 9 months). After 1 month storage at +40° C. the 1M DMG group had a higher activity than all other groups. After 2 months storage at +40° C., the activity dropped off in all groups. It would appear that the majority of damage occurs during the first and second months of thermal challenge. Samples which contain [Hi]DMG/man retained the most antibody activity after 9 months storage with an optical density (OD) of 0.20. All other DMG containing samples had an OD of around 0.15, whilst the mannitol only and PBS controls were around 0.10 (see FIG. 2).

Conclusion

Figure 2:
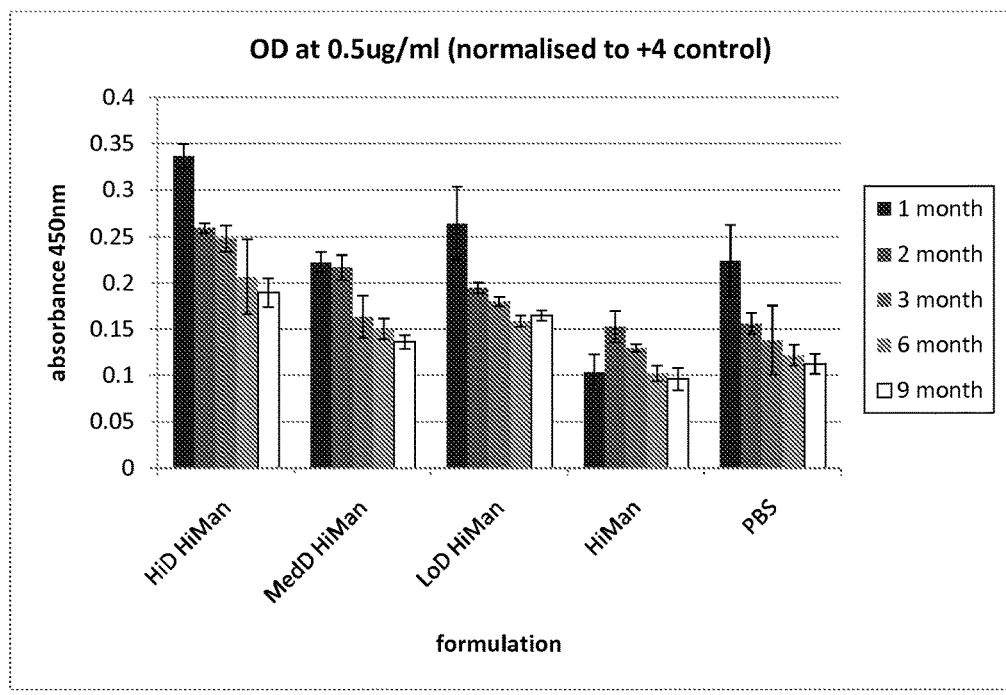
FIG. 2 shows the residual F(ab')2 activity (at 0.5 ug/ml) remaining after a 9 month thermal challenge at +40° C. in Example 1. Error bars show standard error, n=4.

It can be seen in FIG. 1 that the bivalent F(ab')$_2$ is extremely heat labile. When the bivalent F(ab')$_2$ has been lyophilised (with or without excipients), the antibody activity is preserved for significantly longer during thermal challenge. Although all samples retain antibody activity to some extent, those which contain DMG and mannitol in combination retain more antibody activity than those without. The samples which contain 1M DMG with mannitol, protects the bivalent F(ab')$_2$ marginally better than those with 0.7M or 0.3M (FIG. 2).

The statistical analysis in Table 3 above shows that the differences between the antigenicity retained in the samples lyophilized with [HiDMG] and [LoDMG] and samples lyophilized with PBS only at 9 months are statistically significant.

EXAMPLE 2

HRP-conjugated mouse anti *Neisseria gonorrhoeae* IgG monoclonal antibody (mAb) was thermally challenged at +40° C. in the presence and absence of various concentrations of excipients at two months An ELISA assay was used to assess the residual HRP-conjugated mAb binding activity—this was used as a measure of the extent of damage sustained/protection achieved, that is to say the greater the antibody binding activity, the greater the protection obtained.

Methods
Preparation and Thermal Challenge of Mouse Anti *Neisseria gonorrhoeae* IgG HRP-Conjugated Monoclonal Antibody in a Solid Setting with Excipients To determine the protective properties of the excipients described below in a solid setting, 300 µl of each formulation with an antibody concentration of 167 µg/ml was aliquoted into glass freeze drying vials and lyophilized using program 1 on a Virtis lyophiliser as described below. Details of each formulation are set out in Table 4. Each formulation was made up to assess the residual binding activity at 2 months at +40° C., in duplicate.

TABLE 4 details of excipient formulations

| Abbreviation | Description | DMG | mannitol |
| --- | --- | --- | --- |
| HiDMG/man | High [DMG], fixed [mannitol] in PBS | 1M | 0.5M |
| LoDMG/man | Lo[DMG], fixed [mannitol] in PBS | 0.7M | 0.5M |
| Man only | Fixed [mannitol] only in PBS | — | 0.5M |
| PBS only | PBS only | — | — |

The samples were then lyophilized using a VirTis Advantage freeze dryer, using the drying cycles shown in Table 5 below. Samples were frozen at −40° C. for 120 minutes before a vacuum was applied, initially at 100 milliTorre. Shelf temperature and vacuum were adjusted throughout the process.

In the primary drying phase the shelf temperature was initially dropped to −45° C. The secondary drying phase included series of hold steps increasing in temperature up to 30° C. until the drying was completed. Probes recorded shelf temperatures and condenser temperatures.

TABLE 5

| Step | Shelf temp (° C.) | Time (mins) | Ramp/Hold | Vacuum (milliTorre) |
| --- | --- | --- | --- | --- |
| 1 | −45 | 15 | H | 100 |
| 2 | −38 | 30 | R | 100 |
| 3 | −34 | 1200 | H | 100 |
| 4 | −34 | 1200 | H | 100 |
| 5 | −20 | 120 | H | 100 |
| 6 | −10 | 120 | H | 100 |
| 7 | 0 | 120 | H | 100 |
| 8 | 10 | 120 | H | 80 |

TABLE 5-continued

| Step | Shelf temp (° C.) | Time (mins) | Ramp/Hold | Vacuum (milliTorre) |
| --- | --- | --- | --- | --- |
| 9 | 20 | 120 | H | 80 |
| 10 | 30 | 1255 | H | 80 |
| 11 | 4 | 1255 | H | 80 |
| 12 | 4 | 1255 | H | 80 |
| 13 | 4 | 1255 | H | 80 |
| 14 | 4 | 1255 | H | 80 |

Once lyophilised, the vials were placed in a +40° C. incubator to begin thermal challenge.

Assay of HRP-conjugated Mouse Anti *Neisseria gonorrhoeae* IgG Activity

The activity of the HRP-conjugated mouse anti *Neisseria gonorrhoeae* IgG was assayed by ELISA. Antigen (*Neisseria gonorrhoeae*) was removed from −80° C. and allowed to thaw at room temperature. It was diluted to 1.5 µg/ml in PBS and ELISA plate wells in rows A-G were coated with 100 µl, along with two wells in row H which acted as a positive control. Plates were incubated for 18 hours at +4° C. then washed three times with PBS containing 0.05% Tween 20 (wash buffer). Plates were dried by blotting onto a paper towel. This method of blotting was used in every wash step. Plates were blocked for 1.5 hours with PBS containing 5% skimmed milk powder and 0.05% Tween 20 (blocking buffer), at +37° C. with shaking Plates were washed three times with wash buffer before adding the samples.

After incubation at thermal challenge, the mAb formulations were removed from the incubator and reconstituted in 300 µl of PBS, and then diluted to 2 µg/ml in blocking buffer—this resulted in the required antibody concentration for the ELISA (2 µg/ml). Each diluted sample was added to the plate in duplicate and was diluted 2-fold down the plate (final concentrations ranging from 2 µg/ml to 0.0625 µg/ml). The final volume in each well was 100 µl.

A condition with no mAb (blocking buffer only) was also included to measure the background signal. The plates were incubated at +37° C. with shaking for 1.5 hours after which time the plates were washed three times with wash buffer. 100 µl of TMB stabilised chromogen was added to each well and was allowed to react for 20 minutes at room temperature, after which time 100 µl 1200 mM sulphuric acid was added to stop the reaction. The plates were read at 450 nm using Synergy HT Microplate reader.

Statistical Analysis

The average and standard error was taken for each duplicate and the data points plotted as a line graph or as a bar graph at a designated mAb concentration.

The results were normalised to the positive control (a sample obtained from the stock aliquot which had no addition of excipients or thermal challenge). Each result was divided by the average of the two positive control wells for the plate (each plate had a separate positive control).

Results

Activity of Mouse Anti *Neisseria gonorrhoeae* IgG after Thermal Treatment at +56° C. for 7 Days in a Lyophilised and Liquid Setting.

Figure 3:
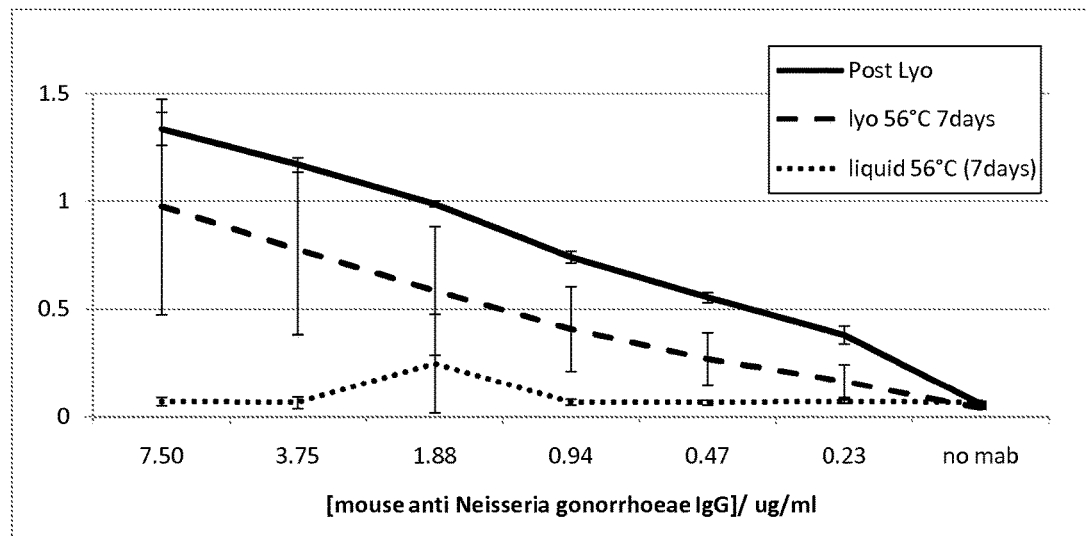
FIG. 3 shows the results from a preliminary study in Example 2 using the unconjugated mouse anti *Neisseria gonorrhoeae* IgG, to determine the initial stability of the antibody at an elevated temperature. The data are not normalized and error bars are standard deviation, n=2. The antibody was found to be extremely heat labile with little activity remaining after 7 days at +56° C. in a liquid setting, and around one third loss of activity in the lyophilised setting.

A preliminary study using the unconjugated mouse anti *Neisseria gonorrhoeae* IgG was carried out to determine the initial stability of the antibody at an elevated temperature. The mAb was lyophilised with a basic formulation (PBS only, 30 µg/ml antibody concentration) and stored at +56° C. An identical, but unlyophilised, control was also placed at +56° C. The results are show in FIG. 3 (data not normalized, error bars are standard deviation, n=2). The antibody was found to be extremely heat labile with little activity remaining after 7 days at +56° C. in a liquid setting, and around one third loss of activity in the lyophilised setting. This provided an excellent starting point for testing the ability of the excipients to stabilise this antibody.

Activity of HRP-Conjugated Mouse Anti *Neisseria gonorrhoeae* IgG after Thermal Treatment at +40° C. with and without Excipients in a Solid Setting.

Figure 4:
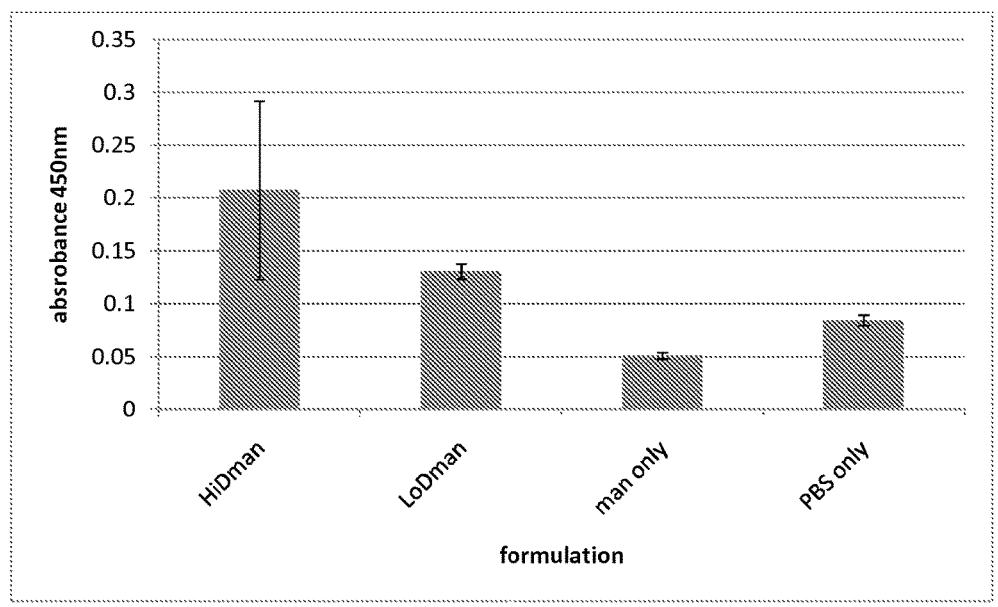
FIG. 4 shows residual HRP-conjugated mAb activity (at 0.5 ug/ml) remaining after thermal challenge at +40° C. in Example 2. Error bars show standard error, n=2.

The HRP-conjugated mAb was thermally challenged in the presence of various combinations and concentrations of excipients and assayed after 2 months at +40° C. FIG. 4 shows data at the 2 month timepoint (error bars are standard error, n=2).

At the 2 month final timepoint, the samples containing DMG and mannitol maintained higher antibody binding activity than the samples containing PBS only and mannitol only. The samples containing PBS only and mannitol only maintained around 25% of the best DMG and mannitol combination.

Conclusion

Following heat challenge, DMG has a benefit when added to mannitol for preserving the binding activity of the HRP-conjugated mouse anti *Neisseria gonorrhoeae* IgG.

EXAMPLE 3

Bivalent F(ab')$_2$ was thermally challenged in the presence of various concentrations of excipients and assayed at different points. An ELISA assay was used to assess the residual F(ab')$_2$ activity—this was used as a measure of the extent of damage sustained.

Methods

Preparation and Thermal Challenge of Bivalent Flab)$_2$ in a Solid Setting with Excipients To determine the protective properties of the excipients described below in a solid setting, 300 µl of each formulation with an antibody concentration of 6.7 µg/ml was aliquoted into glass freeze drying vials and lyophilized using program 1 on a Virtis lyophiliser as described in Example 2. Details of each formulation are set out in Table 6 below.

TABLE 6 details of excipient formulations

| Abbreviation | Description | Suc/Raff (SR) | DMG (D) | MSM (M) |
|---|---|---|---|---|
| --- | PBS only | — | — | — |
| S-- | SR, no DMG, no MSM | 0.1M, 0.01M | — | — |
| S-L | SR, no DMG, LoMSM | 0.1M, 0.01M | — | 0.1M |
| S-H | SR no DMG, HiMSM | 0.1M, 0.01M | — | 1M |
| SL- | SR LoDMG, no MSM | 0.1M, 0.01M | 0.1M | — |
| SLL | SR, LoDMG, LoMSM | 0.1M, 0.01M | 0.1M | 0.1M |
| SLH | SR, LoDMG, HiMSM | 0.1M, 0.01M | 0.1M | 1M |
| SH- | SR, HiDMG, no MSM | 0.1M, 0.01M | 1M | — |
| SHL | SR, HiDMG, LoMSM | 0.1M, 0.01M | 1M | 0.1M |
| SHH | SR, HiDMG, HiMSM | 0.1M, 0.01M | 1M | 1M |

Each formulation was made up to assess the residual binding activity at 6 months at +40° C., in duplicate.

Once lyophilised, the vials were photographed to document the quality of the cakes produced, then placed in an incubator at +40° C. to begin thermal challenge—temperature was constantly monitored using Kelsius system.

Assay of Bivalent F(ab)$_2$ Activity

The activity of the bivalent F(ab')$_2$ was assayed by ELISA. Antigen (Rat IgG2b kappa) was diluted to 0.5 µg/ml in PBS and ELISA plate wells were coated with 100 µl. Two control wells of normal mouse serum at a 1:400000 dilution were also included. These have been found to give consistent results and were used to normalise the data. Plates were incubated for 18 hours at +4° C. then washed three times with PBS containing 0.05% Tween 20 (wash buffer). Plates were dried by blotting onto a paper towel. This method of blotting was used in every wash step. Plates were blocked for 1.5 hours with PBS containing 5% skimmed milk powder and 0.05% Tween 20 (blocking buffer). Plates were washed three times with wash buffer before adding the samples.

After incubation at thermal challenge, the F(ab')$_2$ formulations were removed from incubator and reconstituted in 1 ml of wash buffer—this resulted in the required antibody concentration for the ELISA (2 µg/ml). Each diluted sample was added to the plate in duplicate and was diluted 2-fold down the plate (final concentrations ranging from 2 µg/ml to 0.0625 µg/ml). The final volume in each well was 100 µl. A condition with no mAb (wash buffer only) was also included to measure the background signal. The plates were incubated at room temperature for 1.5 hours after which time the plates were washed five times with wash buffer.

A goat anti human HRP conjugated antibody was diluted 1:5000 in wash buffer and 100 µl added to all wells (a rabbit anti mouse HRP conjugate was diluted to 1:1000 and 100 µl added to the mouse serum control wells). The plates were incubated at room temperature for 1.5 hours then washed five times with wash buffer. 100 µl of TMB stabilised chromogen was added to each well and was allowed to react for 20 minutes at room temperature, after which time 100 µl 200 mM sulphuric acid was added to stop the reaction. The plates were read at 450 nm using Synergy HT Microplate reader.

Statistical Analysis

The average and standard error was taken for each duplicate and the data points plotted as a bar graph at a designated F(ab')$_2$ concentration. The results were normalised to the normal mouse serum controls. Each result was divided by the average of the two positive control wells for the plate (each plate had a separate positive control).

Results

Activity of Bivalent F(Ab)$_2$ Fragments after Thermal Treatment at +56° C. for 24 Hours in a Liquid Setting.

As explained in Example 1 and depicted in FIG. 1, the bivalent F(ab')$_2$ fragments were extremely heat labile with little activity remaining after 24 hours at 56° C., providing an excellent starting point for testing the ability of the excipients to stabilise this antibody.

Activity of Bivalent F(Ab')$_2$ Fragments after Thermal Treatment at +40° C. With and without Excipients in a Solid Setting.

Figure 5:
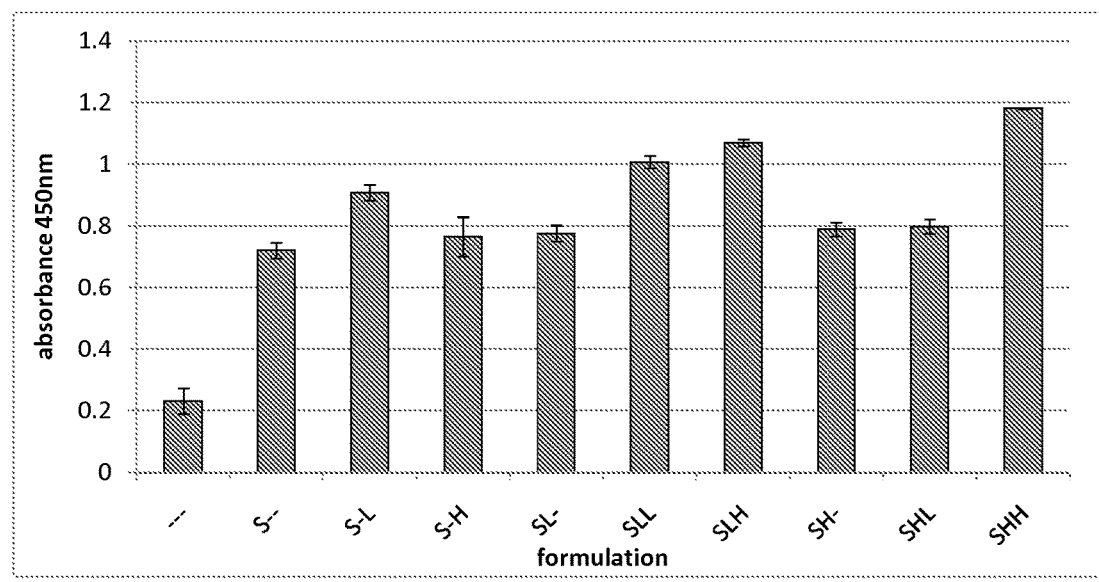
FIG. 5 shows residual bivalent F(ab')2 fragment activity (at 0.5 ug/ml) remaining after a 6 month thermal challenge at +40° C. in Example 3. Error bars are standard error, n=2.

The F(ab')$_2$ was thermally challenged at +40° C. in the presence of various combinations and concentrations of excipients and assayed at 6 months. FIG. 5 shows data after 6 months at +40° C.; --- denotes PBS only and S-—denotes sugar alone.

Conclusion

It can be seen in FIG. 1 that the bivalent F(ab')$_2$ fragments are extremely heat labile. Lyophilisation helps to preserve the antibody binding activity for up to 6 months at +40° C. even in a basic formulation. The addition of low sugar concentrations enhances this protection, which is then enhanced further with the addition of MSM or DMG. The addition of DMG and MSM together provides a protective effect higher than that of DMG or MSM alone with low sugar—this indicates synergy.

EXAMPLE 4

Methods

Solutions containing the HRP-conjugated mouse anti-*Neisseria gonorrhoeae* IgG monoclonal antibody (mAb) with and without various mixtures of the excipients were prepared and assayed ('preLyo'). These solutions were then lyophilised and some of the resulting solids cakes were immediately resuspended to the original volume and assayed ('postLyo'). These samples were used to ellucidate the lyoprotective capacity of the novel excipient mixes.

The remaining solid cakes were subjected to heat challenge at 40° C. for two months before being assayed. These samples were used to ellucidate the thermoprotective capacity of the novel excipient mixes.

HPLC-SEC was used to assay the amount and hydrodynamic size distribution of bulk protein in lyophilised±heat challenged samples in comparison to the untreated and formulated liquid (preLyo) controls. In this way, HPLC-SEC was used to track changes to the bulk protein content of the mAb in response to lyophilisation itself and to the heat challenge.

Preparation and Thermal Challenge of HRP-conjugated Mouse Anti-*Neisseria gonorrhoeae* IgG Monoclonal Antibody in a Solid Setting with Excipients All conditions were lyophilised as 300 µl aliquots containing an antibody concentration of 167 µg/ml. The composition of the four excipient mix conditions and the excipient-free control are documented in Table 7. Mastermixes corresponding to these five conditions were prepared such that each contained enough to supply duplicate lyophilised vials at each time-temperature point plus enough surplus to allow preLyo liquid controls to be assayed.

TABLE 7

| details of excipient formulations | | | |
|---|---|---|---|
| Abbreviation | Description | DMG | mannitol |
| hiDMG/man | High [DMG], fixed [mannitol] in PBS | 1M | 0.55M |
| mdDMG/man | Medium [DMG], fixed [mannitol] in PBS | 0.7M | 0.55M |
| loDMG/man | Low [DMG], fixed [mannitol] in PBS | 0.3M | 0.55M |
| Man only | Fixed [mannitol] only in PBS | — | 0.55M |
| PBS only | PBS only | — | — |

Vials were lyophilised using a VirTis Advantage freeze dryer on recipe 6, as described in Example 1. Following lyophilisation, with the exception of those samples destined for immediate post-lyophilisation assay, samples were then stored in a +40° C. incubation chamber.

HPLC-SEC Assay of HRP-conjugated Mouse Anti *Neisseria gonorrhoeae* IgG Activity The hydrodynamic size distribution and intensity were followed at 214 nm using HPLC-SEC. The buffer used was 0.1 M Sodium Sulphate & 0.1 M Sodium Phosphate adjusted to a final pH at room temperature of 6.8 using concentrated sulphuric acid. The buffer was passed through a 0.45 filter prior to use. The HPLC automatically performed degassing. The flow rate was 0.75 mL. The sample injection volume was 25 µL. The HPLC was equipped with a sample autoloader and the sample chamber was kept at 4° C. The column jacket that surrounded the column was kept at 25° C. The absorption profile of each sample was followed for 24 minutes following injection. Samples were injected in blocks punctuated by both wash steps—in which buffer but no sample was run through the system—and standards—that served to assure consistent operation of the system.

Samples were injected in duplicate as either repeats (preLyo) or replicates from separate vials (postLyo and after heat challenge).

Profile Processing

Quantification of peaks via integration was not attempted owing to the complexity and obfuscation of the many overlapping species present on the profile. Instead, a qualitative assessment was performed in which the profile was treated as a 'fingerprint'. Changes to the control (liquid, prelyophilised) profile that occurred in the profiles of non-control samples were noted. For clarity, a single representative trace of each condition was chosen for presentation.

Results

Standard Curve Construction and Processing

A representative standards run was used as a quality assurance measure in this study. Five species were included in the standards mix and are listed in Table 8.

TABLE 8

| Sizes and retention volumes of the HPLC-SEC standards | | |
|---|---|---|
| size/kD | log[size] | RT/min |
| 670 | 2.826075 | 8.44 |
| 158 | 2.198657 | 11.56 |
| 44 | 1.643453 | 13.46 |
| 17 | 1.230449 | 14.91 |
| 1.35 | 0.130334 | 18.04 |

The latter two were used to construct a standard curve shown, which was subsequently used to estimate the sizes of peaks of interest.

Lyoprotection: Pre & PostLyo Conditions

During the following description of peak area retention, emphasis will be placed on the highest point of the peak complex. This point begins at 8 minutes and is associated with an estimated size of 1.07 MDa (using the standard curve discussed above). HRP was conjugated post-translationally via a chemical process that covalently attached the moiety to certain surface-exposed residues on the mAb; the large size of the initial peak suggests that multiple adhesion sites were utilised.

Figure 6:
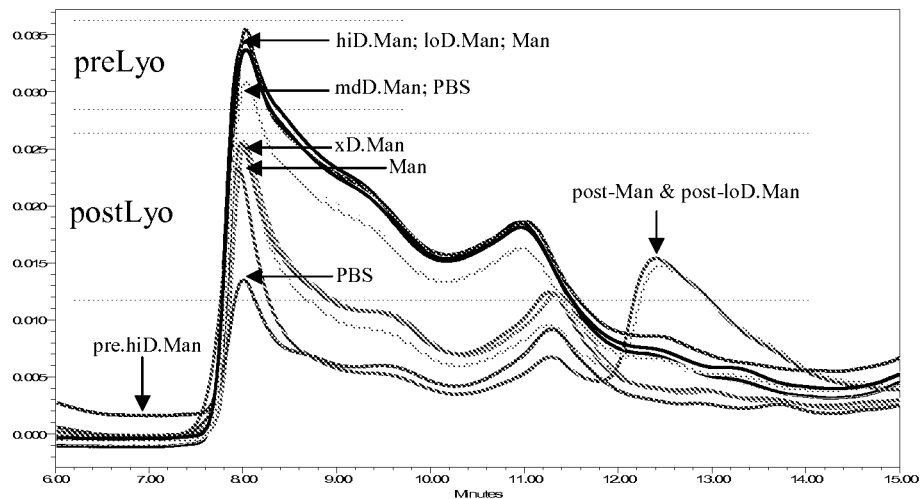
FIG. 6 shows HPLC-SEC trace of all pre- and post-lyophilisation conditions in Example 4. Legend: pre: prelyophilised (liquid) sample; post: post lyophilised sample; hiD.Man: 1.0M DMG+0.55M Mannitol; mdD.Man: 0.7M DMG+0.55M Mannitol; lo.DMan: 0.3M DMG+0.55M Mannitol; xD.Man: [1.0M or 0.7M or 0.3M DMG]+0.55M Mannitol; Man: 0.55M Mannitol & PBS: Phosphate Buffered Saline (control).

FIG. 6 indicates that all peak areas were larger prior to lyophilisation than after it for all samples. Following lyophilisation, the biggest drop in peak area retention occurred solely in the PBS condition; all other conditions essentially showed equivalent peak area retention with mannitol-only trailing slightly behind the three DMG-containing conditions.

A new peak is observable after lyophilisation in the mannitol-only and [0.3M DMG & Mannitol] samples. This peak has a retention time of 12.4 minutes and is associated with an estimated size of 77 kDa (using the standard curve discussed above).

Taken together these results indicate that optima for both peak area retention and profile fidelity occurred with samples containing either [0.7 M DMG & mannitol] or [1.0 M DMG & mannitol].

Thermoprotection: 2 Month Heat-challenged Conditions

Figure 7:
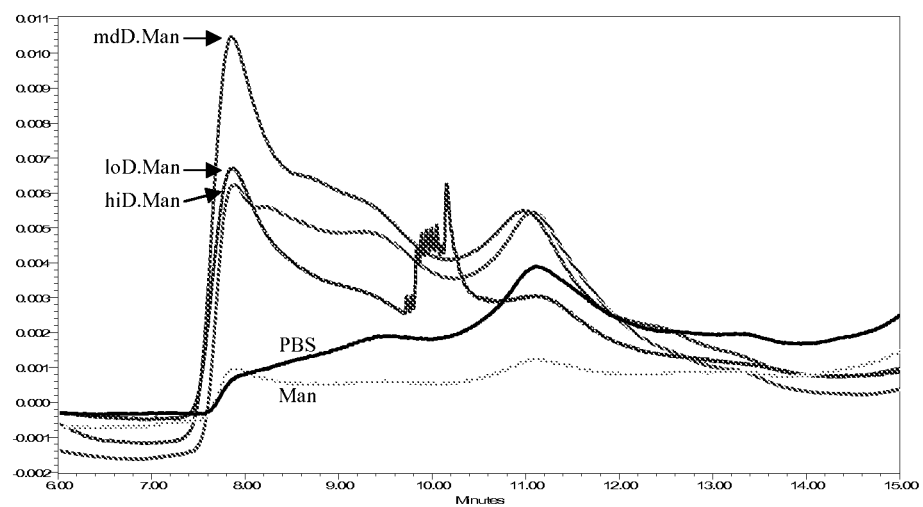
FIG. 7 shows the HPLC traces of all 5 conditions after two months' incubation at 40° C. in Example 4. Legend: pre: prelyophilised (liquid) sample; post: post lyophilised sample; hiD.Man: 1.0M DMG+0.55M Mannitol; mdD.Man: 0.7M DMG+0.55M Mannitol; lo.DMan: 0.3M DMG+0.55M Mannitol; xD.Man: [1.0M or 0.7M or 0.3M DMG]+0.55M Mannitol; Man: 0.55M Mannitol & PBS: Phosphate Buffered Saline (control).

FIG. 7 shows that after two months at 40° C. the biggest peak area drop was observed in PBS and mannitol-only conditions which both presented peak areas close to baseline levels. The three remaining samples—all of which contain DMG in addition to mannitol—all preserve the general profile of the preLyo (liquid) positive control condition shown in FIG. 6. Of these three DMG-containing samples, the highest peak area retention occurred in the condition containing [0.7M DMG & mannitol]. The other two conditions presented essentially equivalent peak area retentions.

These results indicate that—after the thermal challenge—mannitol alone was insufficient to preserve the profile of the mAb (as was PBS) and that addition of DMG was capable of preserving the profile of the mAb. Furthermore, absence of DMG was associated with an essentially absence of the main peak bulk mass (the mass beginning with the peak at 7.85 minutes that correlates to an estimated weight of approximately 1.07 MDa) whilst its addition was associated with the highest peak area retention.

The optimum amount of DMG tested (in coincidence with 0.55M mannitol) was 0.7M but both 0.3M and 1.0M are also capable of preserving the profile.

Conclusion

The data presented and discussed herein indicate that mannitol and DMG & mannitol could preserve the general characteristics of the chromatographic profile of the mAb through the lyophilisation process whilst PBS alone could not. Following additional heat challenge, better peak area retention was observed in samples containing DMG. Profile integrity was preserved in conditions that contained the highest two concentrations of DMG but not in the mannitol-only condition or the lower DMG condition.

The presence of DMG had a significant positive impact on peak area retention and was necessary to preserve profile fidelity after the stress treatment of 2 months at 40° C. Both the mannitol-only and PBS conditions were of decimated peak area retention and did not preserve profile fidelity.

The overall conclusion was that the optimal condition for both lyoprotection and thermoprotection was medium DMG (0.7M) and 0.55M mannitol.

Example 5

Methods

Monovalent Fragment Antigen-Binding (Fab) was thermally challenged in the presence of various concentrations of excipients and assayed at different points. An ELISA assay was used to assess the residual Fab activity—this was used as a measure of the extent of damage sustained.

Preparation and Thermal Challenge of Monovalent Fragment Fab in a Solid Setting with Excipients To determine the protective properties of the excipients described in section 4.1 in a solid setting, 300 μl of each formulation with an antibody concentration of 6.7 μg/ml was aliquoted into glass freeze drying vials and lyophilized using program 1 on a Virtis lyophiliser as described in Example 2. Details of each formulation are set out in Table 9.

TABLE 9 details of excipient formulations

| Abbreviation | Description | Suc/Raff (SR) | DMG (D) | MSM (M) |
| --- | --- | --- | --- | --- |
| S-- | SR, no DMG, no MSM | 0.1M, 0.01M | — | — |
| S-L | SR, no DMG, LoMSM | 0.1M, 0.01M | — | 0.1M |
| S-H | SR no DMG, HiMSM | 0.1M, 0.01M | — | 1M |
| SL- | SR LoDMG, no MSM | 0.1M, 0.01M | 0.1M | — |
| SLL | SR, LoDMG, LoMSM | 0.1M, 0.01M | 0.1M | 0.1M |
| SLH | SR, LoDMG, HiMSM | 0.1M, 0.01M | 0.1M | 1M |
| SH- | SR, HiDMG, no MSM | 0.1M, 0.01M | 1M | — |
| SHL | SR, HiDMG, LoMSM | 0.1M, 0.01M | 1M | 0.1M |
| SHH | SR, HiDMG, HiMSM | 0.1M, 0.01M | 1M | 1M |

Each formulation was made up to assess the residual binding activity at 6 months at +4° C., in duplicate.

Once lyophilised, the vials were placed in a +4° C. fridge to begin thermal challenge—the temperature of which was monitored and recorded constantly for any fluctuations in temperature using the Kelsius temperature monitoring system.

Assay of Monovalent Fab Activity

The activity of the monovalent Fab was assayed by ELISA. Antigen (Rat IgG2b kappa) was diluted to 2.5 μg/ml in PBS and ELISA plate wells were coated with 100 μl. Two wells of normal mouse serum at a 1:400000 dilution were also included—this has been found to give consistent results and were used to normalise the data. Plates were incubated for 18 hours at +4° C. then washed three times with PBS containing 0.05% Tween 20 (wash buffer). Plates were dried by blotting onto a paper towel. This method of blotting was used in every wash step. Plates were blocked for 1.5 hours with PBS containing 5% skimmed milk powder and 0.05% Tween 20 (blocking buffer).

Plates were washed three times with wash buffer before adding the samples. After incubation at thermal challenge, the Fab formulations were removed from the fridge and reconstituted in 1 ml of wash buffer—this resulted in the required antibody concentration for the ELISA (2 μg/ml). Each diluted sample was added to the plate in duplicate and was diluted 2-fold down the plate (final concentrations ranging from 2 μg/ml to 0.0625 μg/ml). The final volume in each well was 100 μl. A condition with no mAb (wash buffer only) was also included to measure the background signal. The plates were incubated at room temperature for 1.5 hours after which time the plates were washed five times with wash buffer.

A goat anti human HRP conjugated antibody was diluted 1:5000 in wash buffer and 100 μl added to all wells (a rabbit anti mouse HRP conjugate was diluted to 1:1000 and 100 μl added to the mouse serum control wells). The plates were incubated at RT 1.5 hours then washed five times with wash buffer. 100 μl of TMB stabilised chromogen was added to each well and was allowed to react for 20 minutes at room temperature, after which time 100 μl 200 mM sulphuric acid was added to stop the reaction. The plates were read at 450 nm using Synergy HT Microplate reader.

Statistical Analysis

The average and standard error was taken for each duplicate and the data points plotted as a line graph or as a bar graph at a designated Fab concentration. The results were normalised to a 4° C. stock antibody control. Each result was divided by the average of the two positive control wells for the plate (each plate had a separate positive control).

Results

Activity of Monovalent Fab Fragments after Thermal Treatment at +56° C. For 24 Hours in a Liquid Setting.

Figure 8:
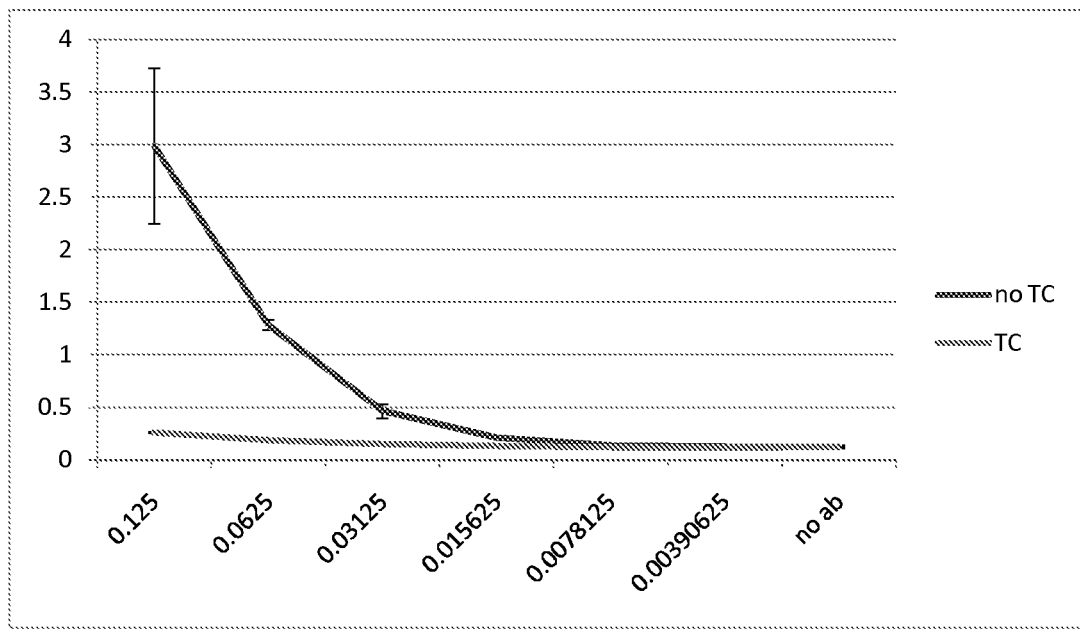
FIG. 8 shows the initial thermal challenge study in Example 5. Data not normalized and error bars are standard deviation, n=2.

In a preliminary study, stock Fab (as supplied by AbD Serotec—concentration 1 mg/ml) was stored at +56° C. to assess initial stability at elevated temperatures. The results are shown in FIG. 8, in which the data not normalized and error bars are standard deviation, n=2. The antibody was found to be extremely heat labile with little activity remaining after 24 hours at 56° C., providing an excellent starting point for testing the ability of our excipients to stabilise this antibody.

Activity of Monovalent Fab Fragments after Thermal Treatment at +4° C. With and without Excipients in a Solid Setting.

Figure 9:
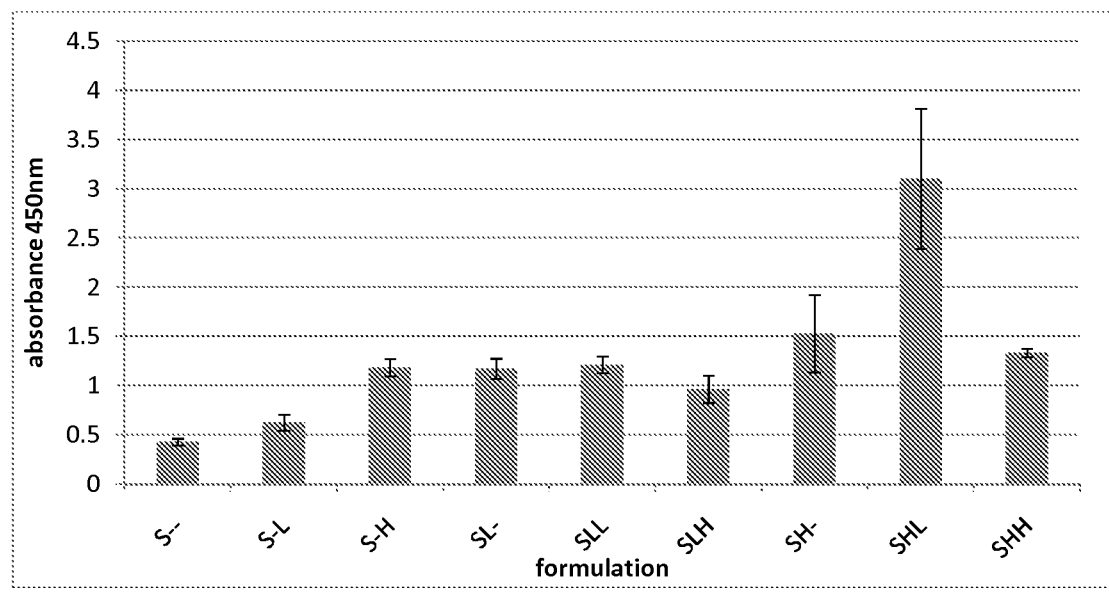
FIG. 9 shows residual monovalent Fab fragment activity (at 0.5 ug/ml) remaining after a 6 month thermal challenge at +4° C. in Example 5. Error bars are standard error, n=2.

The Fab was thermally challenged in the presence of various combinations and concentrations of excipients and assayed after 6 months at +4° C. FIG. 9 shows data at 6 months at +4° C.; S——denotes sugar alone. (Error bars are standard deviation, n=2)

After storage at +4° C., the addition of sugar alone was not sufficient to protect at 6 months. When MSM is combined with high DMG and sugar (SHL and SHH), the level of protection is much higher, indicating synergy—this is further enhanced with addition of more MSM.

Conclusion

It can be seen in FIG. 8 that the monovalent Fab fragments are extremely heat labile. Lyophilisation helps to preserve the antibody binding activity for up to 6 months at +4° C. even in a basic sugar-only formulation. The use of sugar, MSM and DMG in combination may result in synergy.

EXAMPLE 6

Methods
Design of Experiment

MODDE 9.0 was used to generate a Doehlert design (see Table 10 below). Doehlert designs are a form of response surface modelling (RSM) design constructed from regular simplexes and support quadratic models. Doehlert designs are extendable in different directions and new factors can be added to an existing design. Unlike regular formulation designs non-significant factors can be eliminated from the analysis and so do not become a confounding factor.

Cytokines Used in this Study

During routine cell culture of M-NFS-60s, cells were stimulated using purified recombinant mouse macrophage-colony stimulating factor (Mouse M-CSF) according to ATCC recommendations. Mouse M-CSF was obtained from Milteny Biotec (product number 130-094-129) and was provided unformulated.

Stability studies were performed using unformulated granulocyte-colony stimulating factor (G-CSF) obtained from Peprotech (300-23). This G-CSF was expressed in *E. coli* and provided unformulated. The activity of this G-CSF was determined by the manufacturer as ≥1×10$^7$ units/mg.

M-NFS-60 Cells

M-NFS-60 cells were recovered from liquid nitrogen storage. A single passage of these cells was used to produce a storage bank of cells. 1 ml aliquots of passage 1 cells were produced with cells at 6.43×10$^5$ cells/ml in RPMI growth medium, and 5% DMSO, and 10% foetal bovine serum (FBS). The aliquots were frozen down at −80° C. before subsequent transfer to liquid nitrogen storage. This bank of cells was used to establish further cultures for this investigation.

Routine Maintenance of M-NFS-60 Cells

Cells were maintained according to ATCC guidelines. Briefly, cells were propagated in RPMI-1640 medium plus 0.05 mM β-mercaptoethanol, 10% FBS, 1% Penicillin streptomycin, and 62 ng/ml M-CSF. Cells were reared at +37° C., +5% $CO_2$. Cells were seeded at 2.5×10$^4$ viable cells/ml.

Preparation, Lyophilisation and Thermal Challenge of G-CSF

Excipients were prepared in acetate buffer as described in Table 10.

TABLE 10

| Sample Number | DoE Design | | | | Initial Solids Stock | | | ? Weight in 5 ml (g) | | | ? Protein Stock (µg/ml) |
|---|---|---|---|---|---|---|---|---|---|---|---|
| | Raffinose (mM) | DMG (M) | Sucrose (M) | Protein (µg/ml) | Raffinose (mM) | DMG (M) | Sucrose (M) | Raffinose | DMG | Sucrose | |
| 1 | 333.3 | 1.1 | 0.8 | 250.0 | 444.4 | 1.5 | 1.1 | 1.12 | 1.11 | 0.83 | 1000.0 |
| 2 | 250.0 | 2.1 | 0.8 | 250.0 | 333.3 | 2.8 | 1.1 | 0.84 | 2.07 | 0.83 | 1000.0 |
| 3 | 250.0 | 1.4 | 1.5 | 250.0 | 333.3 | 1.9 | 2.0 | 0.84 | 1.43 | 1.51 | 1000.0 |
| 4 | 250.0 | 1.4 | 1.0 | 368.6 | 333.3 | 1.9 | 1.3 | 0.84 | 1.43 | 1.00 | 1474.3 |
| 5 | 0.0 | 1.1 | 0.8 | 250.0 | 0.0 | 1.5 | 1.1 | 0.00 | 1.11 | 0.83 | 1000.0 |
| 6 | 83.3 | 0.1 | 0.8 | 250.0 | 111.1 | 0.2 | 1.1 | 0.28 | 0.15 | 0.83 | 1000.0 |
| 7 | 83.3 | 0.8 | 0.2 | 250.0 | 111.1 | 1.1 | 0.2 | 0.28 | 0.79 | 0.15 | 1000.0 |
| 8 | 83.3 | 0.8 | 0.7 | 131.4 | 111.1 | 1.1 | 0.9 | 0.28 | 0.79 | 0.66 | 525.7 |
| 9 | 250.0 | 0.1 | 0.8 | 250.0 | 333.3 | 0.2 | 1.1 | 0.84 | 0.15 | 0.83 | 1000.0 |
| 10 | 250.0 | 0.8 | 0.2 | 250.0 | 333.3 | 1.1 | 0.2 | 0.84 | 0.79 | 0.15 | 1000.0 |
| 11 | 250.0 | 0.8 | 0.7 | 131.4 | 333.3 | 1.1 | 0.9 | 0.84 | 0.79 | 0.66 | 525.7 |
| 12 | 166.7 | 1.8 | 0.2 | 250.0 | 222.2 | 2.3 | 0.2 | 0.56 | 1.75 | 0.15 | 1000.0 |
| 13 | 166.7 | 1.8 | 0.7 | 131.4 | 222.2 | 2.3 | 0.9 | 0.56 | 1.75 | 0.66 | 525.7 |
| 14 | 166.7 | 1.1 | 1.3 | 131.4 | 222.2 | 1.5 | 1.8 | 0.56 | 1.11 | 1.34 | 525.7 |
| 15 | 83.3 | 2.1 | 0.8 | 250.0 | 111.1 | 2.8 | 1.1 | 0.28 | 2.07 | 0.83 | 1000.0 |
| 16 | 83.3 | 1.4 | 1.5 | 250.0 | 111.1 | 1.9 | 2.0 | 0.28 | 1.43 | 1.51 | 1000.0 |
| 17 | 83.3 | 1.4 | 1.0 | 368.6 | 111.1 | 1.9 | 1.3 | 0.28 | 1.43 | 1.00 | 1474.3 |
| 18 | 166.7 | 0.5 | 1.5 | 250.0 | 222.2 | 0.6 | 2.0 | 0.56 | 0.47 | 1.51 | 1000.0 |
| 19 | 166.7 | 0.5 | 1.0 | 368.6 | 222.2 | 0.6 | 1.3 | 0.56 | 0.47 | 1.00 | 1474.3 |
| 20 | 166.7 | 1.1 | 0.3 | 368.6 | 222.2 | 1.5 | 0.4 | 0.56 | 1.11 | 0.32 | 1474.3 |
| 21 | 166.7 | 1.1 | 0.8 | 250.0 | 222.2 | 1.5 | 1.1 | 0.56 | 1.11 | 0.83 | 1000.0 |
| 22 | 166.7 | 1.1 | 0.8 | 250.0 | 222.2 | 1.5 | 1.1 | 0.56 | 1.11 | 0.83 | 1000.0 |
| 23 | 166.7 | 1.1 | 0.8 | 250.0 | 222.2 | 1.5 | 1.1 | 0.56 | 1.11 | 0.83 | 1000.0 |

Masses of each excipient were weighed out and dissolved in 3 ml of pre-warmed acetate buffer. A brief period of warming in a microwave and vortexing was applied. Once fully dissolved, the total volume was made up to 5 ml with additional acetate buffer. Solutions were deliberately made-up at 1.3× the desired final concentration (according to the design shown in Table 10).

2 ml glass vials were prepared containing 75 µl of excipient mix and 25 µl of G-CSF (at concentrations stated in Table 10). One vial was prepared for each formulation described in Table 10.

The vials were loaded into an aluminium plate and freeze-dried as described in Example 2.

On completion of the lyophilisation cycle the machine held samples at +4° C. until they could be recovered. Vials were sealed under vacuum, and their cakes photographed and scored 1-5 before being transferred to +56° C. for a 4 day heat challenge. After heat challenge samples were transferred to +4° C. until it was practical to assay them.

Assay of G-CSF in M-NFS-60 cells using XTT (2,3-bis[2-methoxy-4-nitro-5sulfophenyl]-2H-tetrazolium-5 carboxyanilide inner salt)

Cells were suspended in RPMI-1640 containing 10% FBS, 1% penicillin streptomycin and 0.05 mM β-Mercaptoethanol but no cytokines. Cells were seeded to a 96 well plate at 20000 cells per well, 190 µl/well.

Lyophilised G-CSF samples were recovered from refrigeration and reconstituted in 100 µl of sterile water. 20 µl of each sample was removed and diluted 1 in 3 in RPMI-1640. Seven more dilutions were produced from the 1 in 3 dilution by 10 fold serial dilution thus producing a 10 fold dilution series from 1 in 3 to 1 in $3\times10^7$. Each dilution was added to a well on 3 separate plates, at 10 µl per well.

Additionally, unformulated G-CSF was recovered from storage at +4° C. and reconstituted to a concentration of 15 µg/ml in sterile water. This sample was diluted 1 in 100 to produce an initial standard of 150 ng/ml. A half $Log_{10}$ dilution series was produced to generate a standard curve between 150 ng/ml and 0.05 ng/ml. Each standard was added to 3 wells per plate at 10 µl per well.

The plates were then placed at +37° C., +5% $CO_2$ (EQP#014) for 72 hours. After 72 hours vials of XTT with 1% PMS were reconstituted in PBS (5 ml per vial). Multiple vials were reconstituted and these vials were pooled prior to use. 40 µl of the XTT solution was added per well and the plates returned to +37° C., +5% $CO_2$ for a further 8 hours. At this time plates were given a mild mixing to disperse XTT formazan and then absorbance at 450 nm and 690 nm was measured in a plate reader.

Estimation of Recovered G-CSF

Absorbance at 690 nm was subtracted from the absorbance at 450 nm for each sample. The known concentration of standards was plotted against the normalised absorbance and the part of the curve showing exponential increase was identified. The data points in this concentration range were plotted as natural log of concentration versus normalised absorbance.

A least squares regression line was produced for the standards on each plate separately. The formula for this standard curve was then used to estimate the concentration of G-CSF in each formulated treatment on that particular plate. The dilution of G-CSF that was most dilute and yet still within the dynamic absorbance range of the assay was used to estimate concentration which was adjusted relative to the known dilution factor.

Since different formulations comprised differing starting G-CSF concentrations the estimated concentration post heat challenge was converted to a percentage of the starting value to allow fair comparison. An average of the three measurements taken was used in subsequent analysis.

Results

Cake quality produced in this study was assessed by photography of the cakes immediately after lyophilisation and subsequent scoring from 0 (very poor) to 5 (very good). This assessment is quite subjective and the scale not necessarily strictly linear, furthermore this one assessment is attempting to capture multiple effects, e.g. cake collapse, melt-back, shrinkage etc. However, the scores remain useful and are shown in Table 11.

TABLE 11

DoE Design

| | Raffinose (mM) | DMG (M) | Sucrose (M) | Protein (µg/ml) | % Recovered Activity | Cake Quality |
|---|---|---|---|---|---|---|
| 1 | 333.3 | 1.1 | 0.8 | 250.0 | 8.5 | 1.5 |
| 2 | 250.0 | 2.1 | 0.8 | 250.0 | 29.4 | 0.5 |
| 3 | 250.0 | 1.4 | 1.5 | 250.0 | 14.3 | 4.0 |
| 4 | 250.0 | 1.4 | 1.0 | 368.6 | 153.7 | 1.5 |
| 5 | 0.0 | 1.1 | 0.8 | 250.0 | 6.7 | 1.0 |
| 6 | 83.3 | 0.1 | 0.8 | 250.0 | 5.6 | 4.0 |
| 7 | 83.3 | 0.8 | 0.2 | 250.0 | 24.9 | 2.0 |
| 8 | 83.3 | 0.8 | 0.7 | 131.4 | 16.0 | 2.5 |
| 9 | 250.0 | 0.1 | 0.8 | 250.0 | 34.2 | 4.5 |
| 10 | 250.0 | 0.8 | 0.2 | 250.0 | 56.0 | 3.0 |
| 11 | 250.0 | 0.8 | 0.7 | 131.4 | 39.2 | 2.8 |
| 12 | 166.7 | 1.8 | 0.2 | 250.0 | 68.0 | 0.5 |
| 13 | 166.7 | 1.8 | 0.7 | 131.4 | 53.0 | 1.0 |
| 14 | 166.7 | 1.1 | 1.3 | 131.4 | 134.1 | 1.5 |
| 15 | 83.3 | 2.1 | 0.8 | 250.0 | 17.1 | 0.5 |
| 16 | 83.3 | 1.4 | 1.5 | 250.0 | 70.2 | 1.0 |
| 17 | 83.3 | 1.4 | 1.0 | 368.6 | 92.3 | 1.0 |
| 18 | 166.7 | 0.5 | 1.5 | 250.0 | 142.1 | 1.5 |
| 19 | 166.7 | 0.5 | 1.0 | 368.6 | 115.4 | 3.5 |
| 20 | 166.7 | 1.1 | 0.3 | 368.6 | 72.5 | 2.0 |
| 21 | 166.7 | 1.1 | 0.8 | 250.0 | 110.2 | 1.0 |
| 22 | 166.7 | 1.1 | 0.8 | 250.0 | 76.3 | 1.0 |
| 23 | 166.7 | 1.1 | 0.8 | 250.0 | 72.1 | 0.5 |

Though an elegant cake may be important, a priority of this study was maximising recovered G-CSF activity and cake quality was a secondary factor.

Recovered activity was expressed as a percentage of starting activity because each formulation had differing starting activity and this allowed better comparison of formulations. Recovered activity also displayed a range in responses although most were within a LOG loss and all were within 1.5 LOG loss. The response ranged from 5.6 to 153% (see Table 11). That several formulations yielded recovered activity of over 100% is presumably a product of the inherent variability within this assay. Centre-points showed a relatively wide spread in this response (72.1-110.2%) but since significant models could be fitted it is thought this spread is small enough relative to the between formulation variation in response.

Figure 10:
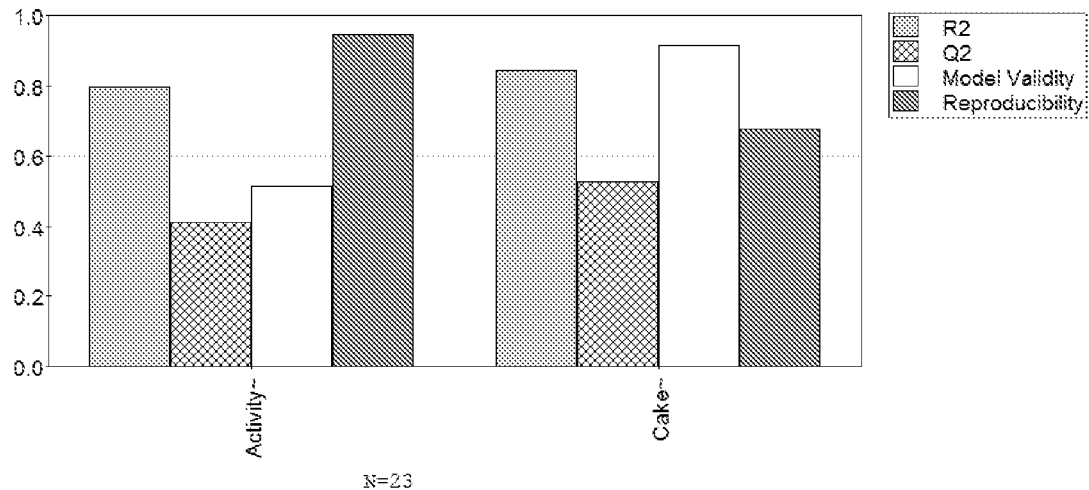
FIG. 10 shows a summary of the statistics of the model used to represent the data in Example 6. "Activity" represents model for response=% recovered activity, "Cake" represents model for response=cake quality. In general a value of 1 for each measure implies perfection. $R^2$=coefficient of determination—a measure of goodness of fit. $R^2<0.5$=low model significance. $Q^2$=estimate of prediction precision—a measure of goodness of prediction. $Q^2$ should be >0.1 for a significant model. $Q^2$ should be >0.5 for a good model. $R^2$-$Q^2$ should be <0.2 to 0.3. Model validity="a test of diverse model problems". Model validity <0.25=indicator of statistically significant model problems e.g. outliers, incorrect model/transformation. Reproducibility=measure of variation between replicates compared to over-all variability. Reproducibility >0.5 implies significance.

Significant models could be fitted for both of these responses (see FIG. 10). For recovered activity the model assessment parameters are $R^2$=0.79, $Q^2$=0.41, Model Validity=0.51, Reproducibility=0.95. Whilst for cake quality they are $R^2$=0.84, $Q^2$=0.53, Model Validity=0.91, Reproducibility=0.68.

Figure 11:
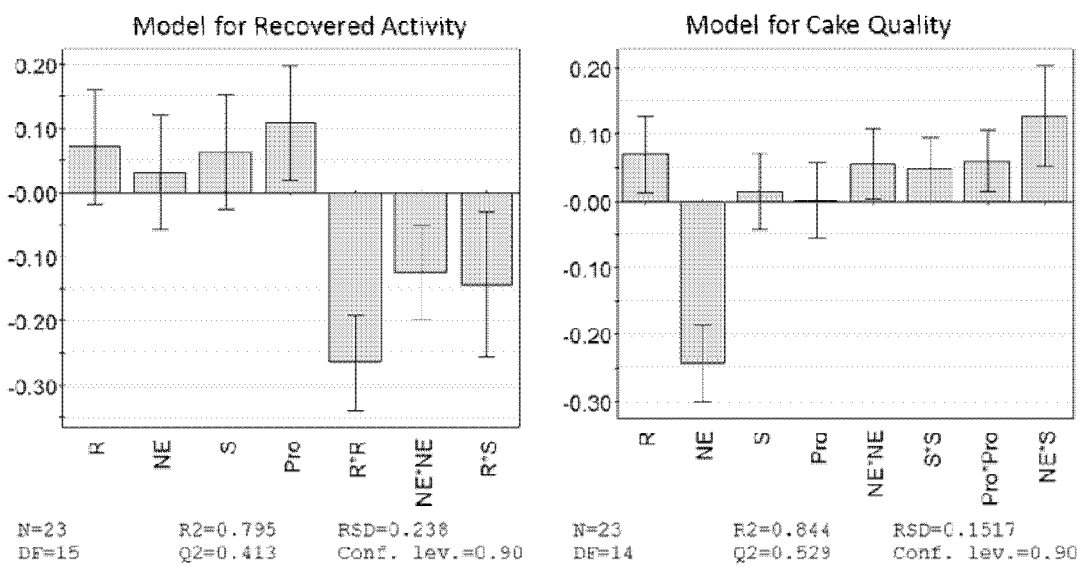
FIG. 11 shows the terms retained in the model after fine tuning in Example 6. Error bars not crossing the origin indicate a significant factor at the 90% C.I

For recovered activity, protein concentration had a positive linear effect. The greater the concentration of protein; the greater the stability. Quadratric effects (non-linear) effects of both DMG and raffinose were observed allowing the identification of a true optimum in their concentration. Sucrose was found to have no effect on recovered activity on its own but does have an interaction with raffinose. Retained coefficients in the model together with an indication of the size of the effect are shown in FIG. 11.

Monte-Carlo simulations were used to predict formulations that maximised recovered activity. Since cake quality was seen as a secondary factor it was disregarded in this initial analysis. An optimum of 203.9 mM Raffinose, 1.3M DMG, 0.45M Sucrose, and 300 µg/ml was identified. This optimum is predicted to yield no loss in activity.

Figure 12:
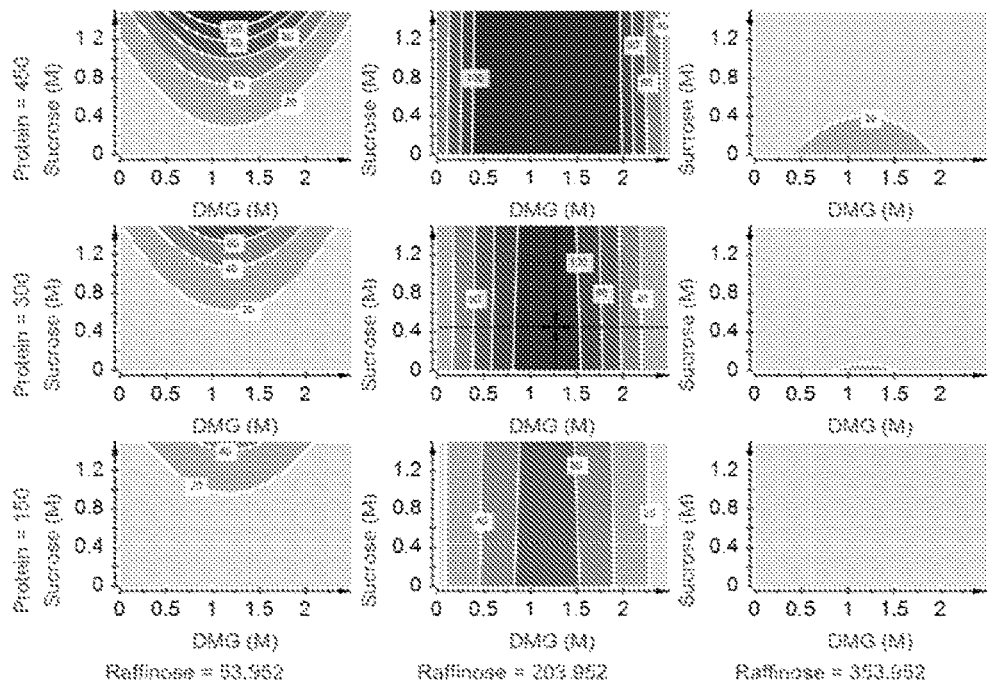
FIG. 12 shows a 4D contour plot showing the predicted recovered G-CSF activity with varying formulation in Example 6. Plots are centred around the Monte-Carlo generated optimum. The cross marks the predicted optimum.

4D contour plots of the optimum region (FIG. 12) clearly demonstrate an optimum DMG concentration of around 1.2M. Increasing protein concentration increases the region around this theoretical DMG optimum where there is predicted 100% recovery. The figure also demonstrated the quadratic effect of raffinose and a clear optimum of 203.9 mM.

Figure 13:
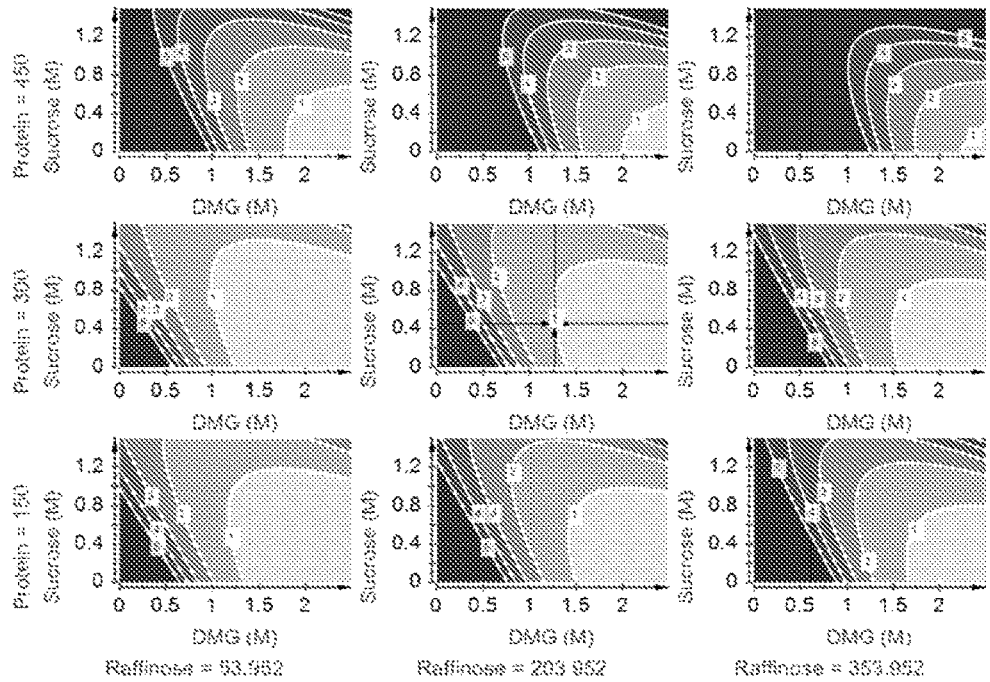
FIG. 13 shows a 4D contour plot showing the predicted cake quality with varying formulation in Example 6. Plots are centred around the Monte-Carlo generated optimum. The cross marks the predicted optimum.

FIG. 13 shows the same region of formulation space and the optimum is marked. However, the response plotted here is cake quality. This model shows that increasing sucrose enhances cake quality. Increasing protein concentration itself is shown to improve cake quality as does increasing raffinose concentration.

A subsequent analysis used Monte-Carlo simulations to maximise recovered activity whilst also maximising cake quality. The two responses were given equal weighting. This identified an optimum formulation of 250 mM raffinose, 0.6M DMG, 0.15M Sucrose, 300 µg/ml protein. Estimates of responses were a cake quality of 4.7 and a recovered activity of 76.5%.

Figure 14:
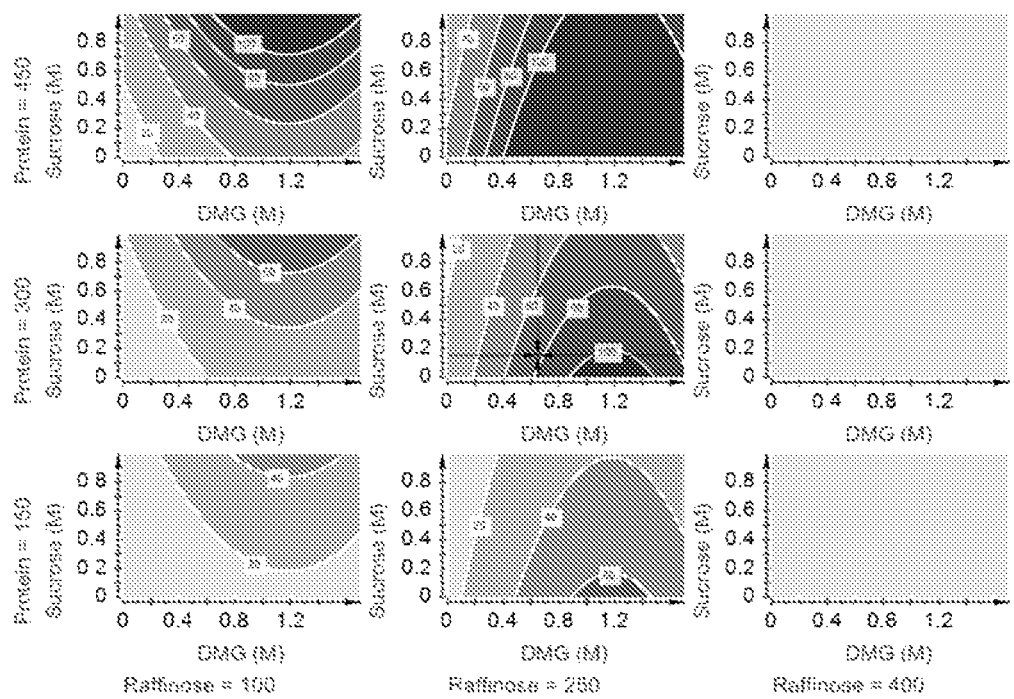
FIG. 14 shows a 4D contour plot showing the predicted recovered G-CSF activity with varying formulation in Example 6. Plots are centred around the Monte-Carlo generated optimum. The cross marks the predicted optimum.
Figure 15:
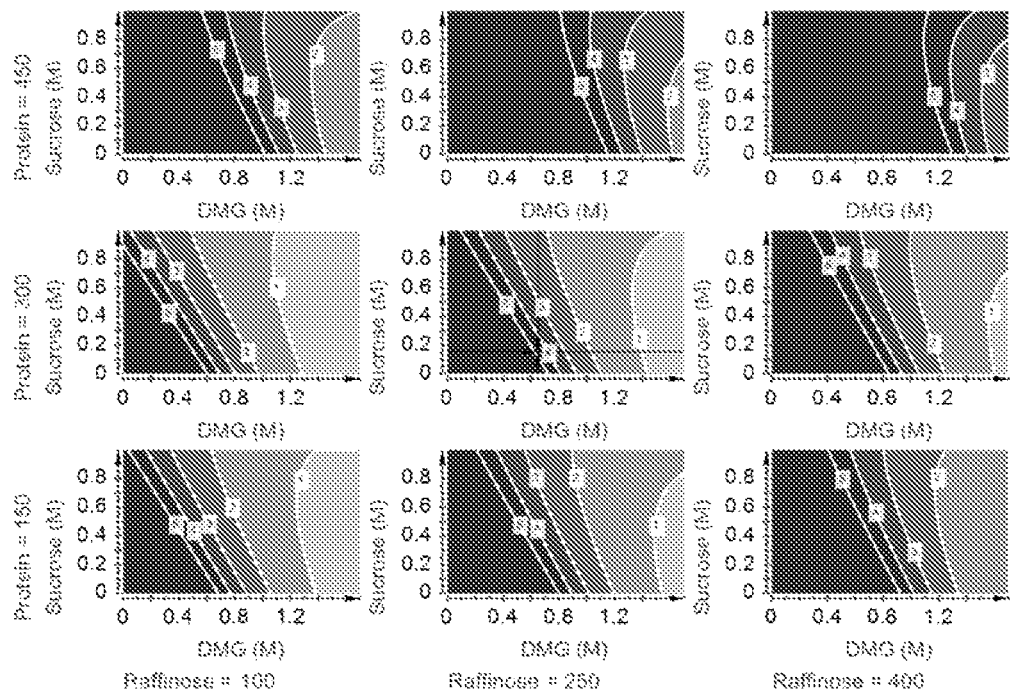
FIG. 15 shows a 4D contour plot showing the predicted cake quality with varying formulation in Example 6. Plots are centred around the Monte-Carlo generated optimum.

FIGS. 14 and 15 show 4D contour plots of the two responses (as in FIGS. 12 and 13) but around the new optimum identified in the second analysis.

EXAMPLE 7

Methods
Design of Experiment
MODDE 9.0 was used to generate a Doehlert design (see Table 12 below). Doehlert designs are described in Example 6.
Cytokines Used in this Study
The M-NFS-60s cells were obtained, prepared and maintained as described in Example 6. The G-CSF was also as described in Example 6.
Preparation, Lyophilisation and Thermal Challenge of G-CSF
Excipients were prepared in acetate buffer as described in Table 12.

TABLE 12

| | DoE Design | | | Initial Solids Stock | | | Weight in 5 ml (g) | | |
|---|---|---|---|---|---|---|---|---|---|
| Sample Number | Raffinose (mM) | TMG (M) | Sucrose (M) | Raffinose (mM) | TMG (M) | Sucrose (M) | Raffinose | TMG | Sucrose |
| 1 | 150.50 | 1.00 | 0.80 | 0.1 | 0.1 | 0.3 | 0.10 | 0.08 | 0.44 |
| 2 | 150.50 | 0.78 | 1.41 | 0.1 | 0.2 | 0.3 | 0.10 | 0.25 | 0.44 |
| 3 | 272.57 | 0.78 | 1.00 | 0.1 | 0.2 | 0.7 | 0.10 | 0.25 | 0.90 |
| 4 | 150.50 | 0.10 | 0.80 | 0.4 | 0.2 | 1.0 | 0.51 | 0.25 | 1.36 |
| 5 | 150.50 | 0.33 | 0.19 | 0.4 | 0.2 | 1.0 | 0.51 | 0.25 | 1.36 |
| 6 | 28.43 | 0.33 | 0.60 | 0.4 | 0.3 | 1.4 | 0.51 | 0.43 | 1.83 |
| 7 | 150.50 | 0.78 | 0.19 | 0.4 | 0.3 | 1.4 | 0.51 | 0.43 | 1.83 |
| 8 | 28.43 | 0.78 | 0.60 | 0.4 | 0.3 | 1.4 | 0.51 | 0.43 | 1.83 |
| 9 | 28.43 | 0.55 | 1.20 | 0.4 | 0.3 | 1.4 | 0.51 | 0.43 | 1.83 |
| 10 | 150.50 | 0.33 | 1.41 | 0.4 | 0.3 | 1.4 | 0.51 | 0.43 | 1.83 |
| 11 | 272.57 | 0.33 | 1.00 | 0.4 | 0.5 | 1.7 | 0.51 | 0.61 | 2.29 |
| 12 | 272.57 | 0.55 | 0.40 | 0.4 | 0.5 | 1.7 | 0.51 | 0.61 | 2.29 |
| 13 | 150.50 | 0.55 | 0.80 | 0.7 | 0.5 | 2.1 | 0.92 | 0.61 | 2.75 |
| 14 | 150.50 | 0.55 | 0.80 | 0.7 | 0.5 | 2.4 | 0.92 | 0.61 | 3.21 |
| 15 | 150.50 | 0.55 | 0.80 | 0.7 | 0.6 | 2.4 | 0.92 | 0.78 | 3.21 |

Masses of each excipient were weighed out and dissolved in 3 ml of pre-warmed acetate buffer. A brief period of warming in a microwave and vortexing was applied to aid dissolution. Once fully dissolved total volume was made up to 5 ml with additional acetate buffer. Solutions were deliberately made-up at 1.3 times the desired final concentration (according to the design shown in Table 12).

2 ml glass vials were prepared containing 75 µl of excipient mix and 25 µl of G-CSF (at concentration of 1200 µg/ml, therefore final concentration in the vial was 300 µg/ml). One vial was prepared for each formulation described in Table 12.

The vials were placed into an aluminium plate and loaded and freeze dried as described in Example 2.

On completion of the lyophilisation cycle the machine held samples at +4° C. until they could be recovered. Vials were sealed under vacuum, and their cakes photographed, and scored 0-5 for cake quality before being transferred to +56° C. for 4 days heat challenge. After heat challenge samples were transferred to +4° C. until it was practical to assay them.

Assay of G-CSF and Estimation of Recovered Activity
G-CSF was assayed and the recovered activity determined as described in Example 6.

Results
A good range in responses of recovered activity was observed from 12.3-81.1% of starting activity as shown in Table 13.

TABLE 13

| | DoE Design | | | % | |
|---|---|---|---|---|---|
| | Raffinose (mM) | TMG (M) | Sucrose (M) | Recovered Activity | Cake Quality |
| 1 | 150.50 | 1.00 | 0.80 | 12.3 | 0.0 |
| 2 | 150.50 | 0.78 | 1.41 | 15.8 | 0.5 |
| 3 | 272.57 | 0.78 | 1.00 | 15.1 | 1.0 |
| 4 | 150.50 | 0.10 | 0.80 | 11.7 | 4.0 |
| 5 | 150.50 | 0.33 | 0.19 | 14.3 | 3.5 |
| 6 | 28.43 | 0.33 | 0.60 | 22.6 | 3.0 |
| 7 | 150.50 | 0.78 | 0.19 | 21.8 | 1.5 |
| 8 | 28.43 | 0.78 | 0.60 | 50.5 | 3.5 |
| 9 | 28.43 | 0.55 | 1.20 | 66.6 | 0.0 |
| 10 | 150.50 | 0.33 | 1.41 | 81.1 | 4.0 |

TABLE 13-continued

| | DoE Design | | | % | |
|---|---|---|---|---|---|
| | Raffinose (mM) | TMG (M) | Sucrose (M) | Recovered Activity | Cake Quality |
| 11 | 272.57 | 0.33 | 1.00 | 70.1 | 2.0 |
| 12 | 272.57 | 0.55 | 0.40 | 60.6 | 3.5 |
| 13 | 150.50 | 0.55 | 0.80 | 39.7 | 2.0 |

TABLE 13-continued

| | DoE Design | | | % | |
| | Raffinose (mM) | TMG (M) | Sucrose (M) | Recovered Activity | Cake Quality |
| --- | --- | --- | --- | --- | --- |
| 14 | 150.50 | 0.55 | 0.80 | 43.8 | 2.0 |
| 15 | 150.50 | 0.55 | 0.80 | 56.8 | 2.0 |

This good spread allowed a relatively strong model to be fitted. None of the formulations suffered greater than a log loss during this quite significant thermal challenge.

The range in response of cake quality was also good. Responses varied from 0 to 4.5, but this very subjective and artificial scoring system does tend to produce a range of responses.

Strength of Fitted Models

A significant model was fitted to both responses. Recovered activity, which is the primary readout gave the strongest model as judged by model assessment parameters ($R^2$=0.87, $Q^2$=0.58, model validity=0.60, reproducibility=0.93), as shown in FIG. 16. The model fitted for cake quality was less strong as also set out in FIG. 16, probably due to subjective nature of cake quality.

Critical Factors in the Models

The critical factors in the model are set out in FIG. 17. For recovered activity the only linear effect observed was that of sucrose which had a positive effect i.e. increasing sucrose increases recovered activity. In addition to this, TMG was found to have a second order, non-linear effect (i.e. an optimum concentration was observed) and was also found to interact with both sucrose and raffinose.

Identification of Optimum Formulations

Monte-Carlo simulations were used in conjunction with the fitted model to predict optimal formulations. The optimum was generated with the specific aim of maximising recovered activity whilst ignoring the less critical response of cake quality. The optimum was found to be 1.4M Sucrose, 0.3M TMG and 150.5 mM Raffinose and was predicted to yield a recovered activity of 78.4%.

Description of Fitted Model

FIG. 18 shows a contour plot of the formulation space surrounding the predicted optimum formulation. The response plotted on this graph is recovered activity as a percentage of starting activity. It can be seen that significant protection can be achieved by high levels of sucrose. Raffinose and TMG both reduce the amount of sucrose required. Compromise between the recovered activity and cake quality may be necessary. A formulation of 150.5 mM raffinose, 0.33M TMG, 1.14M sucrose gave both good recovered activity (81.1%) and cake quality (cake quality score=4).

EXAMPLE 8

Methods

Freeze-dried samples of mannitol formulation were examined by differential scanning calorimetry (DSC) to determine whether the mannitol was amorphous or crystalline. While mannitol is frequently used in freeze-dried formulations, it is usually crystallised during the cycle due to instability over time of the amorphous form.

DSC Procedure

A Perkin Elmer DSC 4000 was used. Initially, a sample of indium run as described below to check calibration of the machine. This involved heating the indium sample from 20° C. to 200° C. at a rate of 20° C. per minute. An endothermic melt is usually seen at 156.6° C. if the DSC to running appropriately.

Following the calibration check, samples were hermetically sealed in aluminium sample pans, and equilibrated to 20° C. inside the DSC. A blank pan was used as the reference, and place onto the heat plate next to the sample. The programme was then run, heating the sample and reference at 20° C. per minute, from 20° C. to 200° C., and then cooling them from 200° C. to 20° C. at 20° C. per minute.

Indium Reference

Indium was used as a reference material to ensure the DSC equipment was producing expected results. Indium has a well-documented melt temperature of 156.6° C. The value obtained in this study was 157.02° C. (see FIG. 20) which is within acceptable limits.

Mannitol

Figure 21:
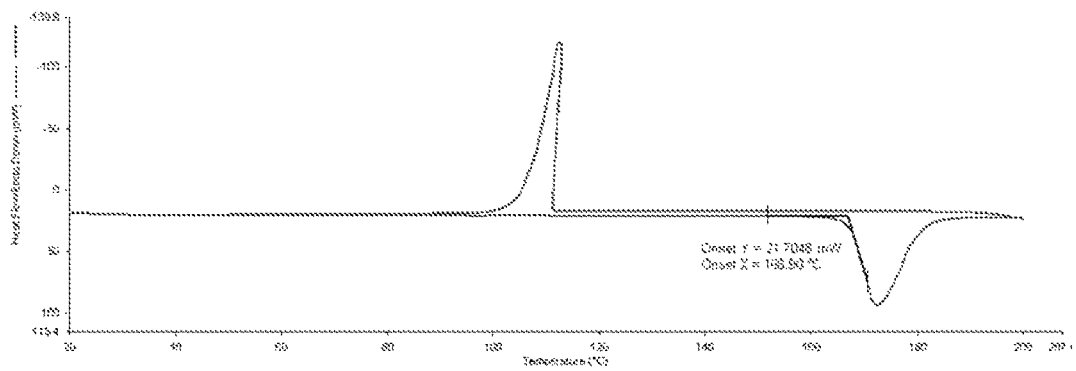

Standard analytical grade mannitol (Sigma) was run in the DSC as a positive control for crystalline material. The results are shown in FIG. 21. Powdered mannitol showed a clear crystalline melt at 166.9° C., which is in agreement with published data. During the cooling stage, there is a clear crystallisation exotherm at 115° C. This experiment showed both melt and re-crystallisation of the mannitol.

Figure 22:
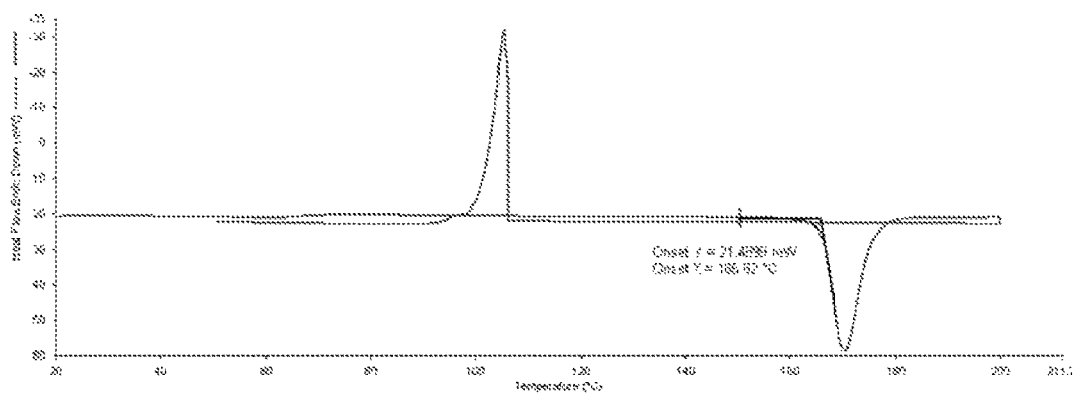

Freeze-dried Mannitol from 274 mM Solution 274 mM mannitol was freeze-dried at −40° C. for 72 hours at approximately 100 μbar (Mechatec lyophiliser), in an attempt to obtain amorphous mannitol. During the heating stage of subsequent DSC analysis, there was a weak re-crystallisation exotherm, prior to the crystalline melt at 166.6° C. This would suggest that much of the mannitol had re-crystallised prior to analysis, due to the very low Tg of anhydrous mannitol of 10° C. The DSC results are shown in FIG. 22. As expected, a strong re-crystallisation exotherm occurred at around 110° C.

Freeze-dried Mannitol in Phosphate Buffered Saline (PBS)

Figure 23:
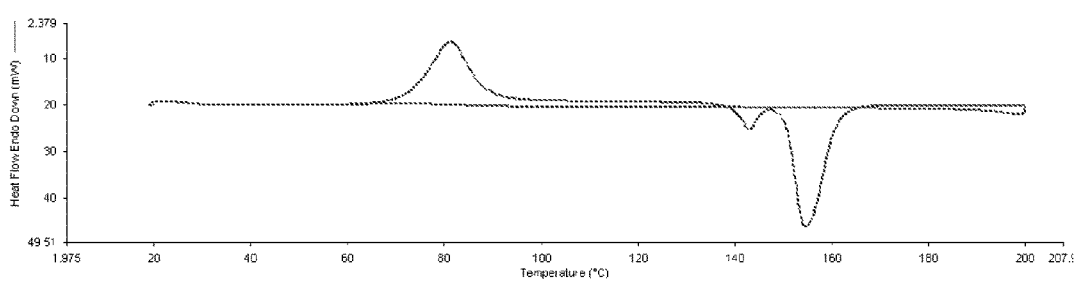

A sample of mannitol (530 mM) in PBS (3.9 mg) was freeze dried. The resulting sample was analysed by DSC and the results are shown in FIG. 23. There was a strong crystalline melt endotherm at around 160° C. and a re-crystalline exotherm at around 80° C. From this it can be concluded that mannitol can crystallize and re-crystallise in a PBS only formulation.

Freeze-dried Mannitol from Solution Containing DMG

Two samples containing mannitol and DMG were freeze-dried (550 mM mannitol, 1M DMG in PBS) using the method described in Table 14 using a VirTis Advantage freeze dryer. Samples were frozen at −40° C. for 120 minutes before a vacuum was applied, initially at 200 milliTorre. Shelf temperature and vacuum were adjusted throughout the process.

In the primary drying phase the shelf temperature was initially dropped to −45° C. The secondary drying phase included series of hold steps increasing in temperature up to 30° C. until the drying was completed. Probes recorded shelf temperatures and condenser temperatures.

TABLE 14

| Step | Shelf temp (° C.) | Time (mins) | Ramp/Hold | Vacuum (milliTorre) |
| --- | --- | --- | --- | --- |
| 1 | −45 | 15 | H | 200 |
| 2 | −34 | 30 | R | 200 |
| 3 | −34 | 1200 | H | 200 |
| 4 | −20 | 120 | R | 200 |

TABLE 14-continued

| Step | Shelf temp (° C.) | Time (mins) | Ramp/Hold | Vacuum (milliTorre) |
|---|---|---|---|---|
| 5 | −10 | 120 | R | 200 |
| 6 | 0 | 120 | R | 200 |
| 7 | 10 | 120 | R | 80 |
| 8 | 20 | 1250 | H | 80 |
| 9 | 20 | 1250 | H | 80 |
| 10 | 20 | 1250 | H | 80 |
| 11 | 20 | 1250 | H | 80 |

Figure 24:
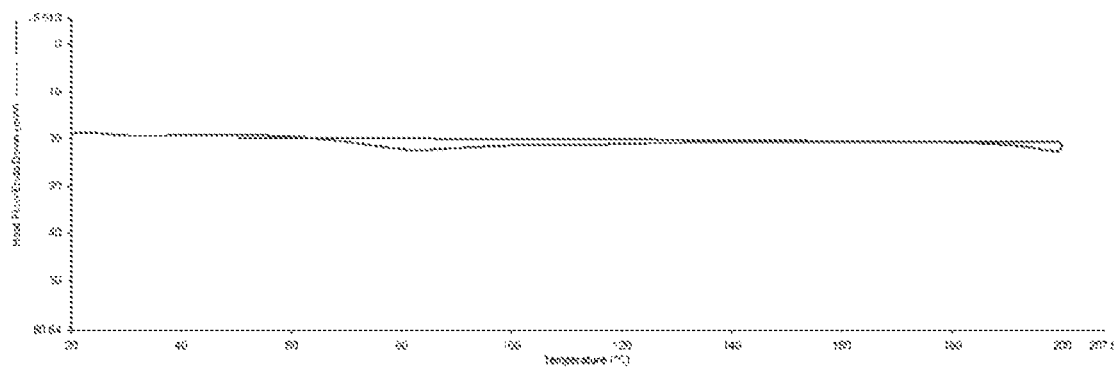
Figure 25:
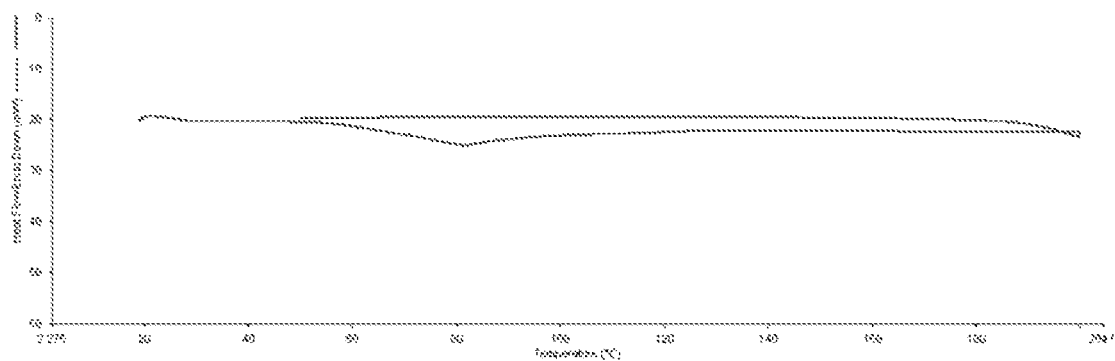

The materials were removed from the vials and run in the DSC. The results are shown in FIGS. 24 and 25. There was a weak endotherm from 60° C. to 100° C., which is likely to be loss of water from the material during heating. However, there is no crystalline melt at 166° C., or re-crystallisation exotherm at around 110° C. This would suggest that, not only is the mannitol amorphous to begin with, but that it is prevented from crystallising during cooling.

Conclusions

The data from the DSC demonstrate that DMG prevents mannitol from crystallising during freeze-drying, such that it retains an amorphous structure.

EXAMPLE 9

The aim of this experiment was to lyophilise recombinant protective antigen (rPA) in formulations containing TMG and/or mannitol. The activity of the rPA was then investigated by competition ELISA. The ELISA was carried out on samples before lyophilisation, Methods Aqueous solutions of DMG and mannitol in the concentrations set out in Table 18 below were prepared.

TABLE 18

| Sample | DMG (M) | Mannitol (M) |
|---|---|---|
| 1 | 0.1 | 0.5 |
| 2 | 0.2 | 0.5 |
| 3 | 0.3 | 0.5 |
| 4 | 0.4 | 0.5 |
| 5 | 0.5 | 0.5 |

These solutions were then freeze-dried. The freeze drying was conducted using a Heto FD 8.0 CD 8030 Freeze dryer (Heto Lab equipment Ltd, UK). The samples were pipetted (1.5 cm$^3$) into clear glass 1.5 ml crimp neck vials (32×11.6 mm). The samples were frozen at (−45° C.) for two hours. The primary drying was conducted (−45° C.) for 15 minutes and was followed by secondary drying as detailed in Table 19.

TABLE 19

| Temperature (° C.) | Time (min) | Vacuum |
|---|---|---|
| −38 | 30 | Yes |
| −37 | 1200 | Yes |
| −34 | 1200 | Yes |
| −20 | 120 | Yes |
| −10 | 120 | Yes |
| 0 | 120 | Yes |
| 10 | 120 | Yes |
| 20 | 120 | Yes |
| 30 | 1255 | Yes |
| 4 | 4800 | Yes |
| 35 | 1000 | No |

In addition, aqueous solutions of (i) 0.5M mannitol and 0.5M glycine [Sample in 6] and (ii) 0.5M mannitol and 0.5M sarcosine [Sample 7] were also freeze-dried in accordance with the above protocol, in order to allow a comparison with Sample 5.

The samples were then analysed by differential scanning calorimetry (DSC) using a TA Q-2000 series thermal analysis system (TA Instruments Ltd, UK). A heating rate of 10° C./min and a cooling rate of 30° C./min were employed.

In addition, a scanning electron microscope (SEM) image was taken for freeze-dried sample 5. This is depicted in FIG. 39.

Results

Figure 35:
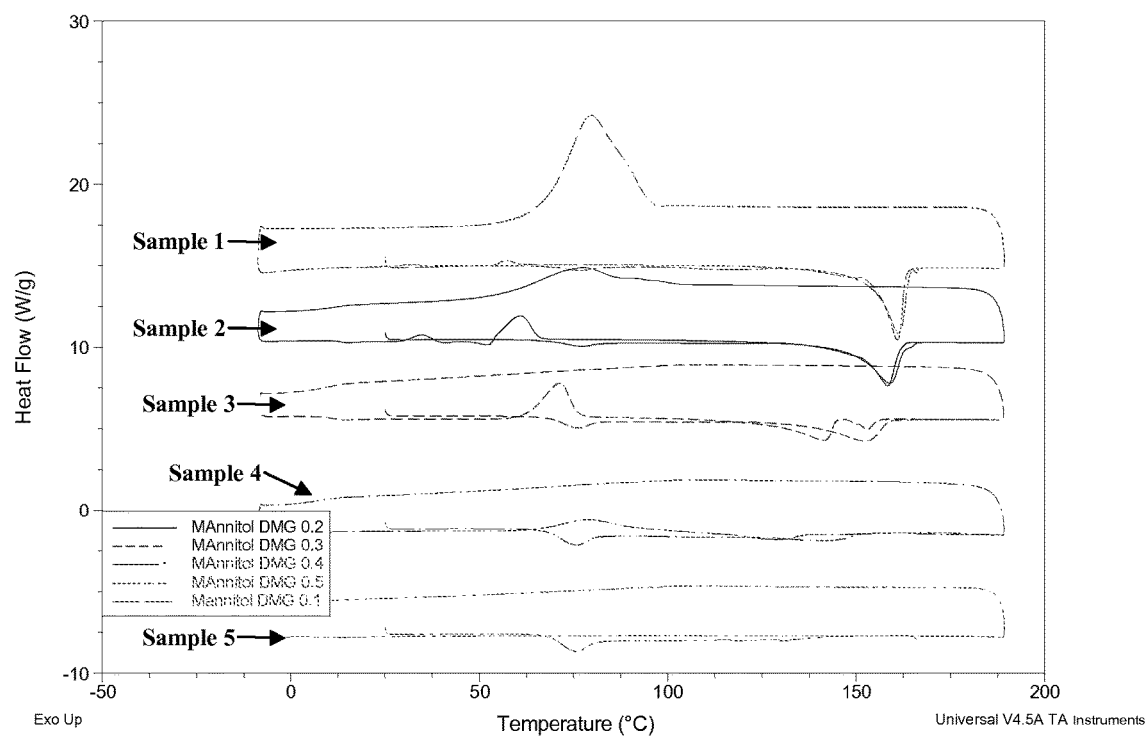
Figure 36:
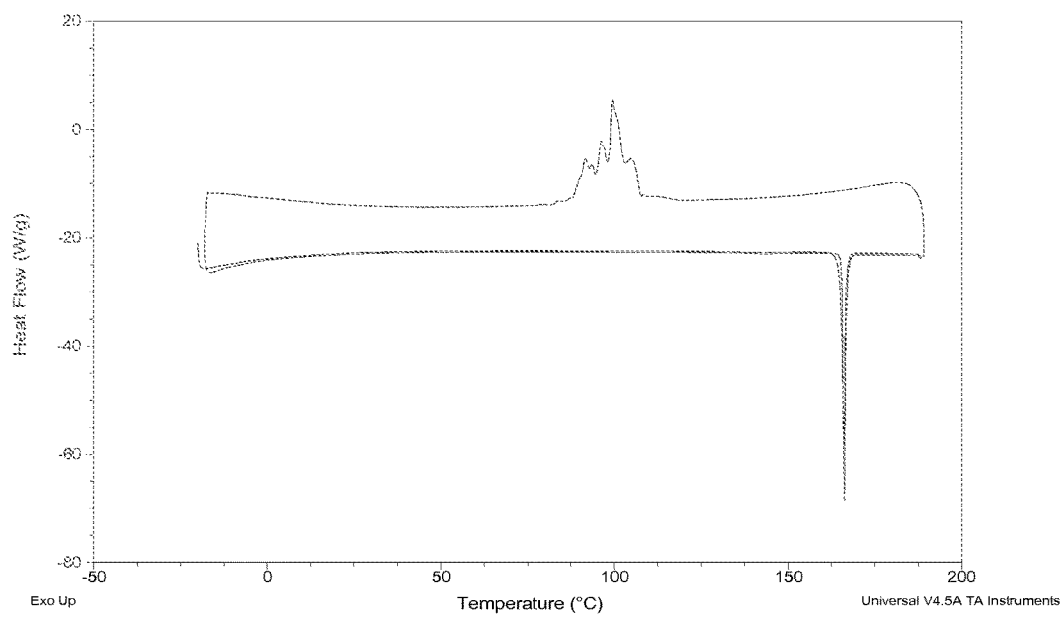

The DSC traces for Samples 1 to 5 are depicted in FIG. 35. For comparison, the DSC trace for mannitol alone is depicted in FIG. 36. The upper trace in FIG. 36 shows that mannitol readily recrystallizes (upper trace) on cooling after initial heating and does not change polymorphic form on reheating.

Figure 37:
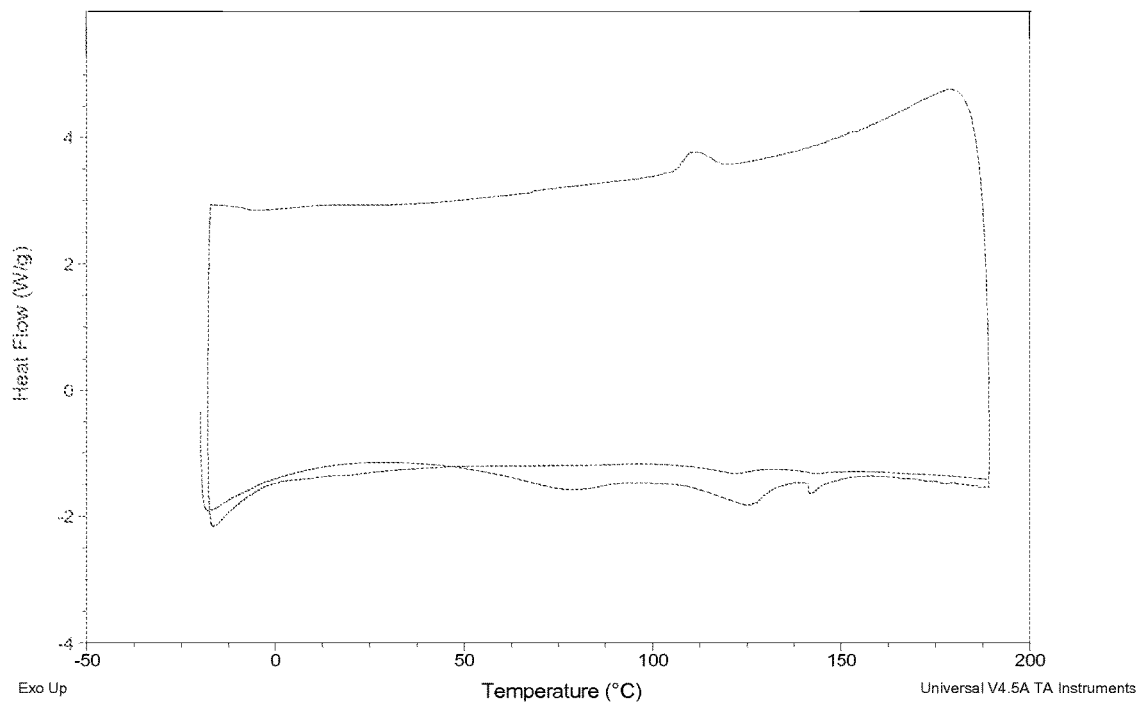

The DSC results in FIG. 35 show that as the DMG concentration is increased, the recrystallisation of mannitol decreases. The recrystallisation peak of mannitol in the cooling cycle is not detectable at concentrations of 0.3M DMG and above. FIG. 37 shows the trace for 0.5M mannitol/0.5M DMG (Sample 5) in more detail.

Figure 38:
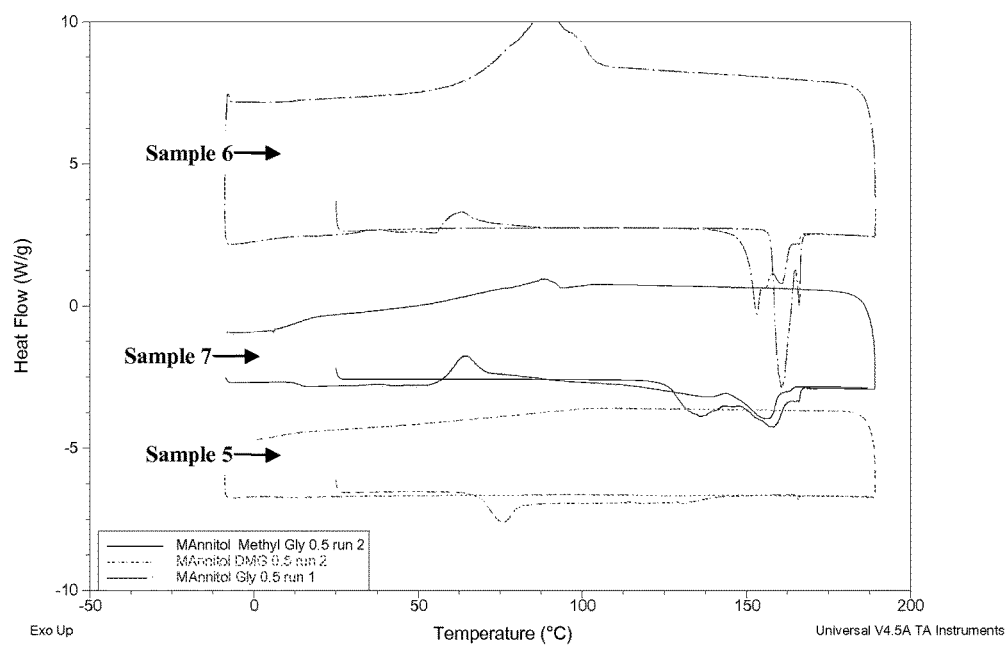

The DSC results in FIG. 38 compare Samples 5, 6 and 7. These results show that DMG is more effective than sarcosine or glycine at the concentrations tested at preventing recrystallisation of mannitol.

TABLE 20

| | Average glass transition temperature onset on second heating cycle (n = 3)/° C. | | |
|---|---|---|---|
| Concentration (M) | DMG | Sarcosine | Glycine |
| 0 | Crystalline | Crystalline | Crystalline |
| 0.1 | Crystalline | Crystalline | Crystalline |
| 0.2 | 11.99 | Crystalline | Crystalline |
| 0.3 | 12.24 | 11.56 | Crystalline |
| 0.4 | 13.14 | 12.46 | Crystalline |
| 0.5 | 13.81 | 12.65 | 11.51 |

These results show that in all cases the glass transition temperature of mannitol increases with increasing excipient concentration, and that DMG is more effective at these concentrations than sarcosine or glycine.

The invention claimed is:

1. A method for preserving a polypeptide during freeze-drying comprising:
   (a) providing a buffered aqueous solution comprising:
      (i) the polypeptide, and
      (ii) as the sole excipients:
         one or more sugars,
         a compound of formula (IA) or a physiologically acceptable salt or ester thereof,
         and
         optionally a compound of formula (II) or a physiologically acceptable salt or ester thereof,

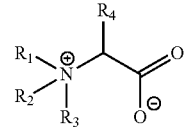

IA wherein:
   $R_1$ represents hydrogen;
   $R_2$ represents $C_{1-4}$ alkyl;
   $R_3$ represents $C_{1-4}$ alkyl; and
   $R_4$ represents hydrogen;

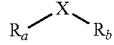

(II)

wherein:
   X represents —S(O)$_2$—;
   $R_a$ and $R_b$ independently represent $C_{1-4}$ alkyl; and
   (b) freeze-drying the solution to form a composition incorporating the polypeptide,
   wherein the polypeptide is an antibody or antigen-binding fragment of an antibody, and wherein the buffered aqueous solution does not comprise an aluminium salt adjuvant.

2. The method according to claim 1 wherein the aqueous solution comprises a compound of formula (I) or a physiologically acceptable salt or ester thereof and a compound of formula (II) or a physiologically acceptable salt or ester thereof.

3. The method according to claim 1, wherein the compound of formula IA is dimethylglycine or a physiologically acceptable salt or ester thereof.

4. The method according to claim 1, wherein (a) the concentration of the compound of formula IA or a physiologically acceptable salt or ester thereof is from 0.001M to 2.5M, and/or (b) the concentration of the optional compound of formula (II) or a physiologically acceptable salt or ester thereof is from 0.001 M to 2.5M, and/or (c) the sugar concentration, or total sugar concentration, is from 0.05M to 3M.

5. The method according to claim 1, wherein (a) the one or more sugars comprise a non-reducing sugar or sugar alcohol, and/or (b) two or more sugars are used and one of the sugars is sucrose, and/or (c) two or more sugars are used, one of the sugars is sucrose and the ratio of the concentration of sucrose relative to the other sugar(s) is from 1:1 to 20:1.

6. The method according to claim 5 wherein the other sugar is raffinose.

7. The method according to claim 1, wherein one sugar is present which is mannitol.

8. The method according to claim 1 in which the aqueous solution is freeze-dried in vials or ampoules which are then optionally sealed.

9. The method according to claim 1, wherein the polypeptide is (i) a monoclonal antibody or a fragment of a monoclonal antibody, or (ii) a chimeric, humanized or human antibody, or a fragment of a chimeric, humanized or human antibody.

10. The method according to claim 1, wherein the compound of formula (II) is dimethylsulfone.

11. The method according to claim 3, wherein the compound of formula (II) is dimethylsulfone.

* * * * *